United States Patent [19]

Taki et al.

[11] Patent Number: 5,451,607

[45] Date of Patent: Sep. 19, 1995

[54] HYDRAZONE DERIVATIVES, PROCESS FOR PRODUCING SAME, INSECTICIDES AND/OR ACARICIDES CONTAINING SAME AS ACTIVE INGREDIENT AND INTERMEDIATE COMPOUNDS THEREOF

[75] Inventors: Toshiaki Taki, Toyonaka; Hirosi Kisida, Takarazuka; Shigeru Saito, Takarazuka; Shinji Isayama, Takarazuka, all of Japan

[73] Assignee: Sumitomo Chemical Co., Ltd., Osaka, Japan

[21] Appl. No.: 47,490

[22] Filed: Apr. 19, 1993

[30] Foreign Application Priority Data

Apr. 23, 1992 [JP] Japan .................................. 4-131616

[51] Int. Cl.[6] ...................... A01N 37/52; C07C 257/22
[52] U.S. Cl. ..................................... 514/632; 514/523;
514/524; 514/530; 514/534; 514/540; 514/541;
514/599; 514/615; 558/408; 558/418; 558/426;
560/1; 560/21; 560/34; 564/74; 564/149;
564/150; 564/226
[58] Field of Search ................. 564/226, 74, 149, 150;
514/632, 523, 524, 530, 534, 540, 541, 599, 615,
632; 558/408, 418, 426; 560/10, 31, 34

[56] References Cited

U.S. PATENT DOCUMENTS

| 4,331,680 | 5/1982 | Giles et al. | 424/303 |
|---|---|---|---|
| 4,432,994 | 2/1984 | Giles et al. | 424/300 |
| 4,980,373 | 12/1990 | Kisida et al. | 514/517 |

FOREIGN PATENT DOCUMENTS

| 7573087 | 7/1987 | Australia . |
|---|---|---|
| 0355832 | 2/1990 | European Pat. Off. . |
| 0500111 | 2/1992 | European Pat. Off. . |
| 3294255 | 4/1990 | Japan . |
| 3074356 | 3/1991 | Japan . |
| 9007495 | 7/1990 | WIPO . |
| 9107382 | 5/1991 | WIPO . |
| 9111438 | 8/1991 | WIPO . |
| 9203421 | 3/1992 | WIPO . |

*Primary Examiner*—Peter O'Sullivan
*Attorney, Agent, or Firm*—Birch, Stewart, Kolasch & Birch

[57] ABSTRACT

There are disclosed hydrazone derivatives of the general formula [I]:

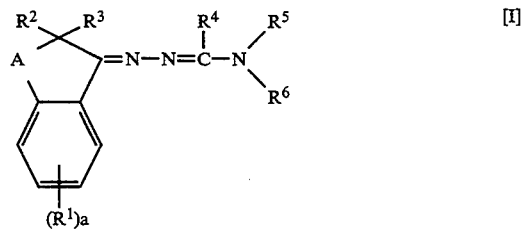

wherein $R^1$ is halogen, etc.; $R^2$ is hydrogen or $C_1$-$C_6$ alkyl, etc.; $R^3$ is hydrogen or $C_1$-$C_6$ alkyl, etc.; $R^4$ is hydrogen or $C_1$-$C_6$ alkyl, etc.; $R^5$ is $C_1$-$C_6$ alkyl, etc.; $R^6$ is hydrogen or $C_1$-$C_6$ alkyl, etc.; A is $(CH_2)_t$, O, $S(O)_n$, etc.; a is an integer of 1 to 4; n is an integer of 0 to 2; and t is an integer of 1 to 3; as well as production processes therefor, insecticides and/or acaricides containing the same as an active ingredient and intermediate compounds thereof.

20 Claims, No Drawings

HYDRAZONE DERIVATIVES, PROCESS FOR PRODUCING SAME, INSECTICIDES AND/OR ACARICIDES CONTAINING SAME AS ACTIVE INGREDIENT AND INTERMEDIATE COMPOUNDS THEREOF

The present invention relates to hydrazone derivatives, a process for producing the same, insecticides and/or acaricides containing the same as an active ingredient and intermediate compounds thereof.

The present inventors have intensively studied excellent insecticidal and acaricidal compounds. As the result, they have found that novel hydrazone derivatives of the general formula [I] depicted below have excellent insecticidal and acaricidal activity, as well as a broad insecticidal spectrum, and that these derivatives also have ovicidal and eclosion-inhibitory activities against certain insect pests, thus completing the present invention.

That is, the present invention provides hydrazone derivatives of the general formula [I]:

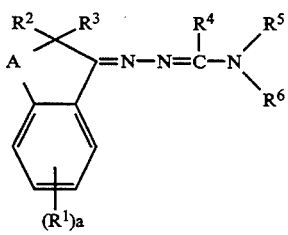

wherein $R^1$ is $R^7$ halogen, cyano, nitro, azide, $OR^7$, $S(O)_nR^7$, $NR^7R^8$, $C(O)R^7$, $CO_2R^7$, $C(O)NR^7R^8$, $OC(O)R^7$, $OCO_2R^7$, $OC(O)NR^7R^8$, $NR^8C(O)R^7$, $NR^8C(O)NR^7R^8$, $OSO_2R^7$ or $NR^8SO_2R^7$; or when a is equal to 2 the two $R^1$ groups are combined to form a 5- or 6-membered ring from $OCH_2O$, $OCH_2CH_2O$ or $CH_2CH_2O$, each of which may be optionally substituted with halogen or methyl;

$R^2$ is hydrogen, $C_1-C_6$ alkyl, $C_1-C_6$ haloalkyl, $C_3-C_6$ cycloalkyl, $C_3-C_6$ cycloalkyl($C_1-C_4$)alkyl, $C_2-C_6$ alkenyl, $C_2-C_6$ haloalkenyl, $C_2-C_6$ alkynyl, $C_2-C_6$ haloalkynyl, $C_1-C_6$ alkoxy($C_1-C_4$)alkyl, $C_1-C_6$ alkylthio($C_1-C_4$)alkyl, $C_2-C_6$ cyanoalkyl, $C_1-C_6$ alkoxycarbonyl($C_1-C_4$)alkyl, $OR^7$, $S(O)R^7$, $NR^7R^8$, cyano, $CO_2R^7$, $C(O)R^7$, $C(O)NR^7R^8$, $C(S)NR^7R^8$, $C(S)R^7$, $C(S)SR^7$,

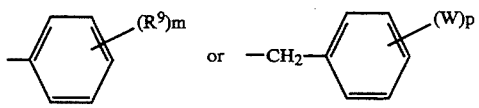

or $C_3-C_7$ cycloalkyl optionally substituted with halogen, methyl or trifluoromethyl;

$R^3$ is hydrogen, $C_1-C_6$ alkyl, $C_1-C_6$ haloalkyl, $C_2-C_6$ alkenyl, $C_2-C_6$ haloalkenyl, $C_2-C_6$ alkynyl, $C_2-C_6$ haloalkynyl, $C_1-C_6$ alkoxy($C_1-C_4$)alkyl, $C_1-C_6$ alkylthio($C_1-C_4$)alkyl, $C_2-C_6$ cyanoalkyl,

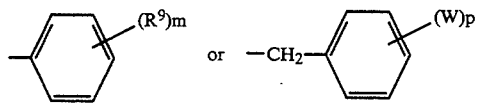

or $C_1-C_5$ alkylene optionally substituted with halogen or methyl, with the proviso that the $R^2$ and $R^3$ groups are combined at both ends to form a 3- to 6-membered ring containing 0 to 2 oxygen or sulfur atoms in the ring;

$R^4$ is hydrogen, $C_1-C_6$ alkyl or $C_1-C_6$ haloalkyl;

$R^5$ is $C_1-C_6$ alkyl, $C_1-C_6$ haloalkyl, $C_2-C_6$ alkenyl, $C_2-C_6$ haloalkenyl, $C_2-C_6$ alkynyl, $C_2-C_6$ haloalkynyl, $C_1-C_6$ alkoxy($C_1-C_4$)alkyl, $C_1-C_6$ alkylthio($C_1-C_4$)alkyl, $C_1-C_6$ haloalkoxy($C_1-C_4$)alkyl, $C_1-C_6$ haloalkylthio($C_1-C_4$)alkyl, $C_2-C_6$ cyanoalkyl, $C_2-C_6$ hydroxyalkyl, $C_1-C_4$ alkylamino-($C_1-C_4$)alkyl, di($C_1-C_4$)alkylamino($C_1-C_4$)alkyl, $C_1-C_6$ alkylcarbonyl, $C_1-C_6$ haloalkylcarbonyl or

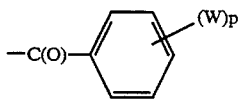

$R^6$ is hydrogen, $C_1-C_6$ alkyl, $C_2-C_6$ haloalkyl, $C_2-C_6$ alkenyl, $C_1-C_6$ alkoxy($C_1-C_4$)alkyl, $C_2-C_6$ cyanoalkyl or $C_2-C_6$ alkynyl; or $C_2-C_5$ alkylene optionally substituted with halogen or methyl, with the proviso that the $R^5$ and $R^6$ groups are combined at both ends to form a 3- to 6-membered ring containing 0 to 2 oxygen or sulfur atoms in the ring;

$R^7$ is hydrogen, $C_1-C_6$ alkyl, $C_1-C_6$ haloalkyl, $C_3-C_6$ cycloalkyl($C_1-c_4$)alkyl, $C_3-C_6$ halocycloalkyl($C_1-C_4$)alkyl, $C_2-C_6$ alkenyl, $C_2-C_6$ haloalkenyl, $C_2-C_6$ alkynyl, $C_2-C_6$ haloalkynyl, $C_1-C_6$ alkoxy($C_1-C_4$)alkyl, $C_1-C_6$ alkylthio-($C_1-C_4$)alkyl, $C_1-C_6$ nitroalkyl, $C_2-C_6$ cyanoalkyl, $C_1-C_6$ alkoxycarbonyl($C_1-C_4$)alkyl, $C_3-C_6$ cycloalkyl, $C_3-C_6$ halocycloalkyl,

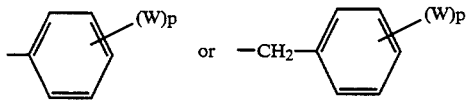

$R^8$ is hydrogen, $C_1-C_4$ alkyl, $C_2-C_6$ alkenyl or $C_2-C_6$ alkynyl; or $C_2-C_5$ alkylene optionally substituted with halogen or methyl, with the proviso that the $R^7$ and $R^8$ groups are combined at both ends to form a 3- to 6-membered ring containing 0 to 2 oxygen or sulfur atoms in the ring;

$R^9$ is $R^7$, halogen cyano nitro azide $OR^7$, $S(O)_nR^7$, $NR^7R^8$, $C(O)R^7$, $CO_2R^7$,$((O)NR^7R^8$, $SO_2NR^7R^8OC(O)R^7$, $OCO_2R^7$, $OC(O)NR^7R^8$, $NR^8C(O)R^7$, $NR^8C(O)NR^7R^8$, $OSO_2R^7$ or $NR^8SO_2R^7$; or when m is equal to 2 the two $R^9$ groups are combined to form a 5- or 6-membered ring from $OCH_2O$, $OCH_2CH_2O$ or $CH_2CH_2O$, each of which may be optionally substituted with halogen or methyl;

$R^{10}$ is hydrogen, $C_1-C_4$ alkyl,

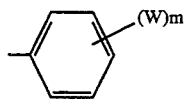

$S(O)_nR^7$, $C(O)R^7$, $CO_2R^7$, $C(O)NR^7R^8$, $C(S)NR^7R^8$, $C(S)R^7$, $P(O)(OR^7)_2$, $P(S)(OR^7)_2$ or $P(O)(R^7)(OR^7)$ with the proviso that when the $R^{10}$ group is any one other than $C(O)R^7$, $C(O)NR^7R^8$ and $C(S)NR^7R^8$ the $R^7$ group is not hydrogen;

A is $(CH_2O)_t$, oxygen, $S(O)_n$, $NR^{10}$, $OCH_2$ or $S(O)_nCH_2$, wherein a hydrogen atom(s) attached to each carbon atom may be optionally substituted with halogen, $C_1$–$C_6$ alkyl, $C_3$–$C_6$ cycloalkyl, $C_3$–$C_6$ halocycloalkyl, $C_3$–$C_6$ cycloalkyl($C_1$–$C_4$)alkyl, $C_2$–$C_4$ alkoxycarbonyl or

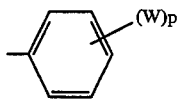

W is halogen, cyano, nitro, $C_1$–$C_2$ alkyl, $C_1$–$C_2$ haloalkyl, $C_1$–$C_2$ alkoxy, $C_1$–$C_2$ haloalkoxy, $C_1$–$C_2$ alkylthio, $C_1$–$C_2$ haloalkylthio, $C_1$–$C_2$ alkylsulfonyl or $C_1$–$C_2$ haloalkylsulfonyl;

a is an integer of 1 to 4; m is an integer of 0 to 3; t is an integer of 1 to 3; n is an integer of 0 to 2; and p is an integer of 0 to 5; as well as a process for producing the same, insecticides and/or acaricides containing the same as an active ingredient and intermediate compounds thereof.

It is preferred that A is $CH_2$, $CH_2CH_2$, oxygen, sulfur, $NR^{10}$, $OCH_2$ or $SCH_2$, wherein a hydrogen atom(s) attached to each carbon atom may be optionally substituted with $C_1$–$C_6$ alkyl or

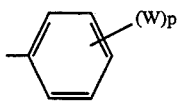

More preferably, A is $CH_2$, $CH_2CH_2$, oxygen, sulfur, $NR^{10}$ or $SCH_2$, wherein a hydrogen atom(s) attached to each carbon atom of $CH_2$ and $CH_2CH_2$ may be optionally substituted with methyl or

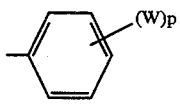

More preferably, A is $CH_2$ or $CH_2CH_2$, wherein a hydrogen atom(s) attached to each carbon atom may be optionally substituted with methyl or

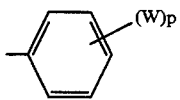

As used herein, the term "halogen" refers to fluorine, chlorine, bromine or iodine. Preferred halogen atoms are fluorine and chlorine.

Examples of the alkyl moiety of alkyl and haloalkyl groups of $R^2$, $R^3$, $R^4$, $R^5$, $R^6$ and 7, as well as of alkylcarbonyl and haloalkylcarbonyl groups of $R^5$, in the compounds of the present invention, are methyl, ethyl, propyl, 1-methylethyl, butyl, 2-methylpropyl, 1-methylpropyl, 1,1-dimethylethyl, pentyl, 3-methylbutyl, 1,1-dimethylpropyl, 2,2-dimethylpropyl and hexyl.

Preferred examples of the haloalkyl moiety of these haloalkyl and haloalkylcarbonyl groups are trifluoromethyl, difluoromethyl, 1-bromo-1,1-difluoromethyl, 2,2,2-trifluoroethyl, 1,1,2,2-tetrafluoroethyl, 2-chloro-1,1,2-trifluoroethyl, 2,2-dichloro-1,1-difluoroethyl, 1,1,2,2,2-pentafluoroethyl, 2-bromo-1,1,2,2-tetrafluoroethyl, 2-chloro-1,1,2,2-tetrafluoroethyl, 2,2,3,3,3-pentafluoropropyl, 1,1,2,2,3,3,3-heptafluoropropyl and 1,1,2,3,3,3-hexafluoropropyl.

Examples of the alkyl group of $R^8$ and $R^{10}$ in the compounds of the present invention are methyl, ethyl, 1-methylethyl, butyl, 2-methylpropyl, 1-methylpropyl and 1,1-dimethylethyl.

Examples of the alkenyl moiety of alkenyl and haloalkenyl groups of $R^2$, $R^3$, $R^5$ and $R^7$, as well as of alkenyl group of $R^6$ and $R^8$, in the compounds of the present invention, are vinyl, 2-propenyl, 1-propenyl, 2-butenyl, 3-butenyl, 2-methyl-2-propenyl, 1-methyl-2-propenyl, 2-methyl-2-butenyl, 3-methyl-2-butenyl and 2,3-dimethyl-2-butenyl.

Preferred examples of the haloalkenyl group are 2,2-dibromovinyl, 2,2-dichlorovinyl, 2,2-difluorovinyl, 3,3-dibromo-2-propenyl, 3,3-dichloro-2-propenyl, 3,3-difluoro-2-propenyl, 3-chloro-4,4,4-trifluoro-2-butenyl, 3-fluoro-4,4,4-trifluoro-2-butenyl, 3-fluoro-2-butenyl, 4,4,4-trifluoro-2-butenyl and 2-fluoro-2-propenyl.

Examples of the alkynyl moiety of the alkynyl and haloalkynyl groups of $R^2$, $R^3$, $R^5$, $R^6$ and $R^7$ are ethynyl 2-propynyl, 2-butynyl, 3-butynyl, 1-methyl-2-propynyl, 2-methyl-3-butynyl, 2-pentynyl, 4-methyl-2-pentynyl, 2-ethyl-3-butynyl and 2-methyl-3-pentynyl. Preferred examples of the haloalkynyl group are 3,3,3-trifluoropropynyl, 3-bromo-3,3-difluoropropynyl, 3,3-difluoropropynyl, 4,4,4-trifluoro-2-butynyl, 4,4-difluoro-2-butynyl, 4-bromo-4,4-difluoro-2-butynyl and 4,4,5,5-tetrafluoro-2-pentynyl.

Examples of the alkoxyalkyl moiety of alkoxyalkyl and alkylthioalkyl groups of $R^2$, $R^3$, $R^5$ and $R^7$, as well as of haloalkoxyalkyl and haloalkylthioalkyl groups of $R^5$, in the compounds of the present invention, are methoxymethyl, 2-methoxyethyl, 3-methoxypropyl, ethoxymethyl, 2-ethoxyethyl, n-propyloxymethyl, (1-methylethyloxy)methyl, 2-(n-propyloxy)ethyl, 2-(1-methylethyloxy)ethyl, n-butyloxymethyl, 2-(1-methylpropyloxy)ethyl, (2-methylpropyloxy)methyl. Preferred examples of the haloalkoxyalkyl group are difluoromethoxyethyl, 2-(bromodifluoromethoxy)ethyl, 2-(trifluoromethoxy)ethyl, 1', 1', 2', 2'-tetrafluoroethoxymethyl, 2', 2', 2'-trifluoroethoxymethyl, 2-(1', 1', 2', 2'-tetrafluoroethoxy)ethyl, 2-(2',2',2'-trifluoroethoxy)ethyl, 2-(1-trifluoromethylethyloxy)ethyl and 2-(2',2',3',3',3'-pentafluoropropyloxy)ethyl. Examples of the alkylthioalkyl moiety are 2-methylthioethyl, 2-ethylthioethyl, 2-propylthioethyl, 2-(1-methylethylthio)ethyl, 2-butylthioethyl, 2-(1-methylpropylthio)ethyl and 2-(2-methylpropylthio)ethyl. Preferred examples of the haloalkylthioalkyl group are difluoromethylthioethyl, 2-(1',1',2',2',-tetrafluoroethylthio)ethyl, 2-(2',2',2'-trifluoroethylthio)ethyl, 2-(2',2',3',3',3'-pentafluoropropylthio)ethyl and 2-(1-trifluoromethylethylthio)ethyl.

Examples of the cyanoalkyl group of $R^2$, $R^3$, $R^5$ and $R^7$ in the compounds of the present invention are 2-cyanoethyl, 3-cyanopropyl, 4-cyanobutyl and 5-cyanopentyl.

Examples of the hydroxyalkyl group of $R^5$ in the compounds of the present invention are hydroxymethyl, 2-hydroxyethyl, 3-hydroxypropyl and 4-hydroxybutyl.

Examples of the alkylaminoalkyl group of $R^5$ in the compounds of the present invention are 2-(N-methylamino)ethyl, 2-(N-ethylamino)ethyl, 2-(N-isopropylamino)ethyl, 3-methylaminopropyl, 2-(N-n-propylamino)ethyl, 2-(N-n-butylamino)ethyl, 2-(N-isobutylamino)ethyl, 2-(N-sec-butylamino)ethyl and 2-(N-t-butylamino)ethyl.

Examples of the dialkylaminoalkyl group of $R^5$ in the compounds of the present invention are 2-(N,N-dimethylamino)ethyl, 2-(N-methyl-N-ethylamino)ethyl, 2-(N,N-diethylamino)ethyl, 3-(N,N-dimethylamino)propyl and 3-(N,N-diethylamino)propyl.

Examples of the nitroalkyl group of $R^7$ in the compounds of the present invention are nitromethyl, 2-nitroethyl, 3-nitropropyl and 4-nitrobutyl.

Examples of the cycloalkyl moiety of cycloalkyl group of $R^2$ and $R^7$, as well as of the halocycloalkyl group of $R^7$, in the compounds of the present invention, are cyclopropyl, cyclobutyl, cyclopentyl, cyclohexyl, 2,2-dimethylcyclopropyl and 1-methylcyclopropyl. Preferred examples of the halocycloalkyl are 2,2-dichlorocyclopropyl, 2-chloro-2-fluorocyclopropyl, 3-chloropentyl, 4-(trifluoromethyl)cyclohexyl, 4-chlorocyclohexyl and 3,4-dichlorocyclohexyl.

Among the compounds of the present invention are preferred hydrazone derivatives of the general formula [I] wherein each of $R^1$ and $R^9$ is independently $R^7$, halogen cyano, nitro, $OR^7$, $SR^7$ or $NR^7R^8$; or when a or m is equal to 2 the two $R^1$ or $R^9$ groups are combined to form a 5- or 6-membered ring from $OCH_2O$, $OCH_2CH_2O$ or $CH_2CH_2O$, each of which may be optionally substituted with halogen or methyl;

$R^2$ is hydrogen, $C_1$–$C_6$ alkyl, $C_1$–$C_6$ haloalkyl, $C_3$–$C_6$ cycloalkyl, $C_3$–$C_6$ cycloalkyl($C_1$–$C_4$)alkyl, $C_3$–$C_6$ alkenyl, $C_3$–$C_6$ haloalkenyl, $C_3$–$C_6$ alkynyl, $C_3$–$C_6$ haloalkynyl, $C_1$–$C_6$ alkoxy($C_1$–$C_4$)alkyl, $C_1$–$C_6$ alkylthio($C_1$–$C_4$)alkyl, $C_2$–$C_6$ cyanoalkyl $CO_2R^7$, $C(O)NR^7R^8$,

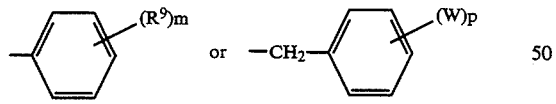

or $C_3$–$C_6$ cycloalkyl optionally substituted with halogen, methyl or trifluoromethyl;

$R^3$ is hydrogen, $C_1$–$C_6$ alkyl, $C_1$–$C_6$ haloalkyl, $C_3$–$C_6$ alkenyl, $C_3$–$C_6$ haloalkenyl, $C_3$–$C_6$ alkynyl, $C_3$–$C_6$ haloalkynyl, $C_1$–$C_6$ alkoxy($C_1$–$C_4$)alkyl, $C_1$–$C_6$ alkylthio-($C_1$–$C_4$)alkyl, $C_2$–$C_6$ cyanoalkyl

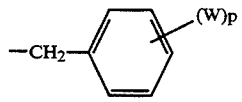

or $C_1$–$C_5$ alkylene optionally substituted with halogen or methyl, with the proviso that the $R^2$ and $R^3$ groups are combined at both ends to form a 3- to 6-membered ring containing 0 or 1 oxygen or sulfur atom in the ring;

$R^4$ is hydrogen, $C_1$–$C_6$ alkyl or $C_1$–$C_6$ haloalkyl;

$R^5$ is $C_1$–$C_6$ alkyl, $C_1$–$C_6$ haloalkyl, $C_3$–$C_6$ alkenyl, $C_3$–$C_6$ haloalkenyl, $C_3$–$C_6$ alkynyl, $C_3$–$C_6$ haloalkynyl, $C_1$–$C_6$ alkoxy($C_1$–$C_4$)alkyl, $C_1$–$C_6$ alkylthio($C_1$–$C_4$)alkyl, $C_1$–$C_6$ haloalkoxy($C_1$–$C_4$)alkyl, $C_1$–$C_6$ haloalkylthio($C_1$–$C_4$)alkyl, $C_2$–$C_6$ cyanoalkyl, $C_2$–$C_6$ hydroxyalkyl, $C_1$–$C_4$ alkylamino-($C_1$–$C_4$)alkyl or di($C_1$–$C_4$)alkylamino($C_1$–$C_4$)alkyl;

$R^6$ is hydrogen, $C_1$–$C_6$ alkyl, $C_2$–$C_6$ haloalkyl, $C_3$–$C_6$ alkenyl or $C_3$–$C_6$ alkynyl, $C_1$–$C_6$ alkoxy($C_1$–$C_4$)alkyl or $C_2$–$C_5$ alkylene optionally substituted with methyl, with the proviso that the $R^5$ and $R^6$ groups are combined at both ends to form a 3- to 6-membered ring containing 0 to 2 oxygen or sulfur atoms in the ring;

$R^7$ is hydrogen, $C_1$–$C_6$ alkyl, $C_1$–$C_6$ haloalkyl, $C_3$–$C_4$ alkenyl, $C_3$–$C_4$ alkynyl, $C_1$–$C_6$ alkoxy($C_1$–$C_4$)alkyl, $C_1$–$C_6$ alkylthio($C_1$–$C_4$)alkyl,

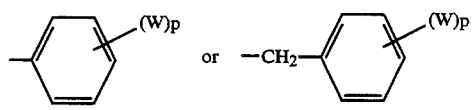

$R^8$ is hydrogen, $C_1$–$C_4$ alkyl, $C_3$–$C_4$ alkenyl or $C_3$–$C_4$ alkynyl; or $C_1$–$C_5$ alkylene optionally substituted with halogen or methyl, with the proviso that the $R^7$ and $R^8$ groups are combined at both ends to form a 3- to 6-membered ring containing 0 to 1 oxygen or sulfur atom in the ring;

$R^{10}$ is hydrogen, $C_1$–$C_4$ alkyl,

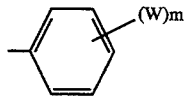

$C(O)R^7$, $CO_2R^7$ or $C(O)NR^7R^8$, with the proviso that when the $R^{10}$ group is $CO_2R^7$ the $R^7$ group is not hydrogen;

A is $CH_2$, $CH_2$, $CH_2$, oxygen, sulfur, oxygen sulfur, $NR^{10}$, $OCH_2$ or $SCH_2$, wherein a hydrogen atom(s) attached to each carbon atom may be optionally substituted with $C_1$–$C_6$ alkyl or

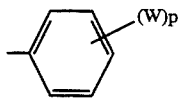

W is halogen, cyano, nitro, $C_1$–$C_2$ alkyl, $C_1$–$C_2$ haloalkyl, $C_1$–$C_2$ alkoxy, $C_1$–$C_2$ haloalkoxy or $C_1$–$C_2$ alkylthio;

a is an integer of 1 to 2; m is an integer of 0 to 2; n is an integer of 0 to 2; and p is an integer of 0 to 2.

Among these hydrazone derivatives, more preferred are those wherein each of $R^1$ and $R^9$ is independently $R^7$, halogen, cyano, nitro or $OR^7$; or when a or m is equal to 2 the two $R^1$ or $R^9$ groups are combined to form a 5-membered ring from $OCH_2O$ which may be optionally substituted with halogen or methyl;

$R^2$ is hydrogen, $C_1$–$C_6$ alkyl, $C_1$–$C_6$ haloalkyl, $C_3$–$C_4$ alkenyl, $C_3$–$C_4$ alkynyl, $C_2$–$C_6$ cyanoalkyl, $CO_2R^7$,

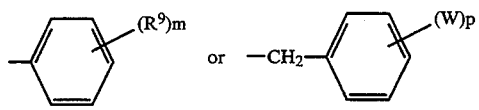

$R^3$ is hydrogen, $C_1$–$C_6$ alkyl, $C_1$–$C_6$ haloalkyl, $C_3$–$C_6$ alkenyl, $C_3$–$C_6$ alkynyl or $C_2$–$C_6$ cyanoalkyl; or $C_1$–$C_5$ alkylene optionally substituted with methyl, with the proviso that the $R^2$ and $R^3$ groups are combined at both ends to form a 3- to 6-membered ring containing 0 or 1 oxygen or sulfur atom in the ring;

$R^4$ is hydrogen or $C_1$–$C_6$ alkyl;

$R^5$ is $C_1$–$C_6$ alkyl, $C_1$–$C_6$ haloalkyl, $C_3$–$C_6$ alkenyl, $C_3$–$C_6$ alkynyl, $C_1$–$C_6$ alkoxy($C_1$–$C_4$)alkyl, $C_2$–$C_6$ cyanoalkyl, $C_2$–$C_6$ hydroxyalkyl, $C_1$–$C_4$ alkylamino($C_1$–$C_4$)alkyl or di($C_1$–$C_4$)alkylamino($C_1$–$C_4$)alkyl;

$R^6$ is hydrogen, $C_1$–$C_6$ alkyl, $C_2$–$C_6$ haloalkyl, $C_3$–$C_6$ alkenyl, $C_3$–$C_6$ alkynyl or $C_1$–$C_6$ alkoxy($C_1$–$C_4$)alkyl; or $C_2$–$C_5$ alkylene optionally substituted with methyl, with the proviso that the $R^5$ and $R^6$ groups are combined at both ends to form a 3- to 6-membered ring containing 0 to 1 oxygen or sulfur atom in the ring;

$R^7$ is hydrogen, $C_1$–$C_3$ alkyl or $C_1$–$C_3$ haloalkyl; and $R^{10}$ is hydrogen, $C_1$–$C_4$ alkyl or ($C_1$–$C_4$ alkoxy)-carbonyl.

Among these hydrazone derivatives, more preferred are those wherein each of $R^1$ and $R^9$ is independently hydrogen, methyl, trifluoromethyl, fluorine, chlorine, bromine, cyano, methoxy, trifluoromethoxy or difluoromethylenedioxy; or when a or m is equal to 2 the two $R^1$ or $R^9$ groups are methylenedioxy or difluoromethylenedioxy;

$R^2$ is hydrogen, $C_1$–$C_6$ alkyl, $C_1$–$C_6$ haloalkyl, $C_3$–$C_4$ alkenyl, $C_3$–$C_4$ alkynyl,

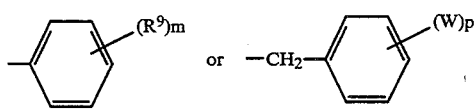

$R^3$ is hydrogen, $C_1$–$C_3$ alkyl, $C_3$–$C_4$ alkenyl or $C_3$–$C_4$ alkynyl; or $C_4$–$C_5$ alkylene, with the proviso that the $R^2$ and $R^3$ groups are combined at both ends to form a 5- to 6-membered ring;

$R^4$ is hydrogen or $C_1$–$C_6$ alkyl;

R is $C_1$–$C_6$ alkyl, $C_3$–$C_4$ alkenyl, $C_3$–$C_4$ alkynyl or $C_1$–$C_3$ alkoxy($C_1$–$C_3$)alkyl; and A is $CH_2$, $CH_2CH_2$, oxygen, sulfur, $NR^{10}$ or $SCH_2$, wherein a hydrogen atom(s) attached to each carbon atom of $CH_2$ and $CH_2CH_2$ may be optionally substituted with methyl or

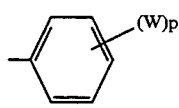

with particularly preferred being the case where when A is oxygen, sulfur or $NR^{10}$ each of $R^2$ and $R^3$ is any one other than

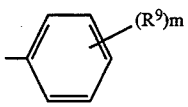

Among these hydrazone derivatives, particularly preferred are those wherein A is $CH_2$ or $CH_2CH_2$, wherein a hydrogen atom(s) attached to each carbon atom may be optionally substituted with methyl or

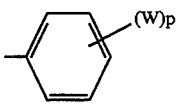

Among these hydrazone derivatives, more preferred are those wherein A is $CH_2$;

$R^2$ is $C_1$–$C_6$ alkyl, allyl, propargyl or

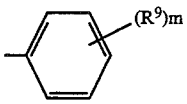

$R^3$ is hydrogen or $C_1$–$C_3$ alkyl; or $C_4$–$C_5$ alkylene, with the proviso that the $R^2$ and $R^3$ groups are combined at both ends to form a 5- or 6-membered ring;

$R^4$ is hydrogen or $C_1$–$C_4$ alkyl;

$R^5$ is $C_1$–$C_6$ alkyl, allyl or propargyl; and $R^6$ is $C_1$–$C_6$ alkyl.

Among these hydrazone derivatives, particularly preferred are those wherein each of $R^1$, $R^9$ and W is independently hydrogen, methyl, fluorine, chlorine, bromine, methoxy or difluoromethoxy.

Also preferred hydrazone derivatives are those wherein A is

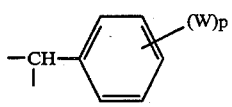

each of $R^2$ and $R^3$ is independently hydrogen or $C_1$–$C_3$ alkyl;

$R^4$ is hydrogen or $C_1$–$C_4$ alkyl;

$R^5$ is $C_1$–$C_6$ alkyl, allyl or propargyl; and $R^6$ is $C_1$–$C_6$ alkyl;

with particularly preferred being the case where each of $R^1$ and W is independently hydrogen, methyl, fluorine, chlorine, bromine, methoxy or difluoromethoxy.

The compounds of the present invention can be produced, for example, by any one of the following processes.

(Production Process A)

The compounds of the present invention are obtained by reacting a compound of the general formula [II]:

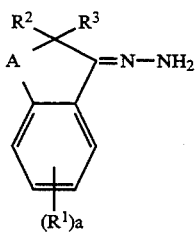 [II]

wherein $R^1$, $R^2$, $R^3$, A and a are each as defined above, with a compound of the general formula [III]:

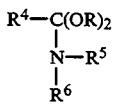 [III]

wherein $R^4$, $R^5$ and $R^6$ are each as defined above; and R is $C_1$–$C_4$ alkyl such as methyl or ethyl.

(Production Process B)

The compounds of the present invention are obtained by reacting a compound of the general formula [IV]:

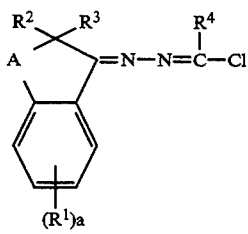 [IV]

wherein $R^1$, $R^2$, $R^3$, $R^4$, A and a are each as defined above, with an amine compound of the general formula [V]:

 [V]

wherein $R^5$ and $R^6$ are each as defined above.

(Production Process C)

The compounds of the present invention are obtained by reacting a compound of the general formula [VI]:

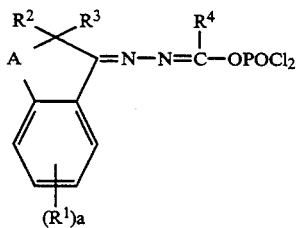 [VI]

wherein $R^1$, $R^2$, $R^3$, $R^4$, and a are each as defined above, with an amine compound of the general formula [V] depicted above.

(production Process D)

The compounds of the present invention are obtained by reacting a compound of the general formula [VII]:

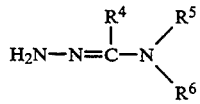 [VII]

wherein $R^4$, $R^5$ and $R^6$ are each as defined above, or a salt thereof (e.g., hydrochloride, hydrobromide or sulfate), with a compound of the general formula [VIII]:

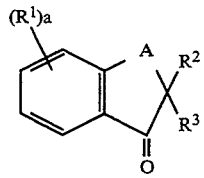 [VIII]

wherein $R^1$, $R^2$, $R^3$, A and a are each as defined above

In the production by process A, B, C or D, solvents are not necessarily used; if used, for example, there can be used aromatic hydrocarbons such as benzene, toluene, xylene, chlorobenzene and o-dichlorobenzene; pyridine compounds such as pyridine and picoline; halogenated hydrocarbons such as chloroform, carbon tetrachloride, 1,2-dichloroethane, 1,1,1-trichloroethane, tetrachloroethane and trichloroethylene; aliphatic hydrocarbons such as n-hexane and n-heptane; alicyclic hydrocarbons such as cyclohexane; water and mixtures thereof.

In the production by process B or C, agents for removing hydrogen halide are not necessarily used; if necessary, for example, an organic base such as triethylamine or N,N-diethylaniline, or an inorganic base such as sodium hydroxide, potassium hydroxide, sodium carbonate or potassium carbonate, is used in an amount of from 1 to 4 equivalents to one equivalent of the compound of the general formula [II], [IV] or [VI].

The reaction is usually carried out at a temperature of from −20° to 200° C., preferably from 0° to 150° C., for a period of from 5 minutes to 100 hours.

In process A or D, the compound of the general formula [III] or [VII] is used in an amount of from 1 to 10 equivalents to one equivalent of the compound of the general formula [II] or [VIII], respectively. In process B or C, the compound of the general formula [V] is used at an amount of from 1 to 100 equivalents to one equivalent of the compound of the general formula [IV] or [VI].

In process D, if necessary, an inorganic acid such as sulfuric acid or hydrochloric acid, or an organic acid such as benzenesulfonic acid or p-toluenesulfonic acid, may be used as a reaction catalyst. The catalyst is usually used at an amount of from 0.01 to 1 equivalent to one equivalent of the compound of the general formula [VIII].

After completion of the reaction, the reaction mixture is subjected to ordinary post-treatment such as concentration or extraction with an organic solvent, followed by concentration, if necessary, with an additional operation such as washing with water or pouring into ice-water thus obtaining the compounds of the present invention.

Further, if necessary, any purification technique such as chromatography or recrystallization may be employed.

The raw materials used for the production of the compounds of the present invention can be produced, for example, according to the process as described in the International Application, Publication No. WO91-07382 or by the following processes.

The compound of the general formula [II] can be produced by reacting a ketone compound of the general formula [VIII]:

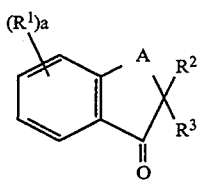  [VIII]

wherein $R^1$, $R^2$, $R^3$, A and a are each as defined above, with hydrazine.

The compound of the general formula [IV] or [VI] can be produced by reacting a compound of the general formula [IX]:

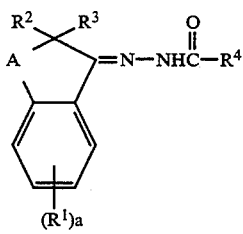  [IX]

wherein $R^1$, $R^2$, $R^3$, $R^4$, A and a are each as defined above, with phosphorous pentachloride or phosphorous oxychloride.

In these productions, solvents are not necessarily used; if used, for example, there can be used aromatic hydrocarbons such as benzene, toluene, xylene, chlorobenzene and dichlorobenzene; halogenated hydrocarbons such as chloroform, carbon tetrachloride, 1,2-dichloroethane, 1,1,1-trichloroethane, tetrachloroethane and trichloroethane; aliphatic hydrocarbons such as n-hexane and n-heptane; alicyclic hydrocarbons such as cyclohexane; and mixtures thereof.

In case where a compound of the general formula [IX] is reacted with phosphorous pentachloride or phosphorous oxychloride to form a compound of the general formula [IV], phosphorous pentachloride or phosphorous oxychloride is usually used in an amount of from 1 to 5 equivalents to one equivalent of the compound of the general formula [IX]. The reaction is usually carried out at a temperature of from room temperature (about 20° C.) to 250° C. for a period of from 5 minutes to 100 hours.

In case where a compound of the general formula [IX] is reacted with phosphorous oxychloride to form a compound of the general formula [VI], phosphorous oxychloride is usually used in an amount of from 1 to 5 equivalents to one equivalent of the compound of the general formula [IX]. The reaction is usually carried out at a temperature of from 0° to 250° C. for a period of from 5 minutes to 100 hours.

After completion of the reaction, the reaction mixture is subjected to ordinary post-treatment such as concentration or extraction with an organic solvent, followed by concentration, if necessary, with an additional operation such as washing with water or pouring into ice-water, thus obtaining the compound of the general formula [IV] or [VI].

Further, if necessary, any purification technique such as chromatography or recrystallization may be employed.

The compounds of the general formulae [IV] and [VI] obtained by these processes may also be used in the reaction of process B or C, without any isolation or purification.

The compound of the general formula [IX] can be produced by reacting the compound of the general formula [II] with an acid halide of the general formula [X]:

  [X]

wherein X is halogen such as chlorine or bromine; $R^4$ is as defined above, or with an acid anhydride of the general formula [XI]:

$(R^4CO)_2O$  [XI]

wherein $R^4$ is as defined above.

In this reaction, the acid halide of the general formula [X] or the acid anhydride of the general formula [XI] is usually used in an amount of from 1 to 100 equivalents to one equivalent of the compound of the general formula [II]. The reaction is usually conducted at a temperature of from −20° to 200° C. for a period of from 5 minutes to 100 hours.

After completion of the reaction, the reaction mixture is subjected to ordinary post-treatment such as extraction with an organic solvent, followed by concentration, if necessary, with an additional operation such as washing with water or pouring into ice-water, thus obtaining the compound of the general formula [IX]. If necessary, any purification technique such as chromatography or recrystallization may be employed.

The compound of the general formula [IX] can also be produced by reacting a compound of the general formula [XII]:

  [XII]

wherein $R^4$ is as defined above, with the compound of the general formula [VIII].

The compound of the general formula [IX] obtained by these processes may also be used in the production of the compound of the general formula [IV] or [VI], without any isolation or purification.

The ketone compound of the general formula [VIII] can be produced, for example, by any one of the following processes.

(Synthesis Process 1)

In case where A is $CH_2$, $R^2$ is

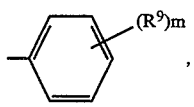

and $R^3$ is hydrogen:

Scheme 1

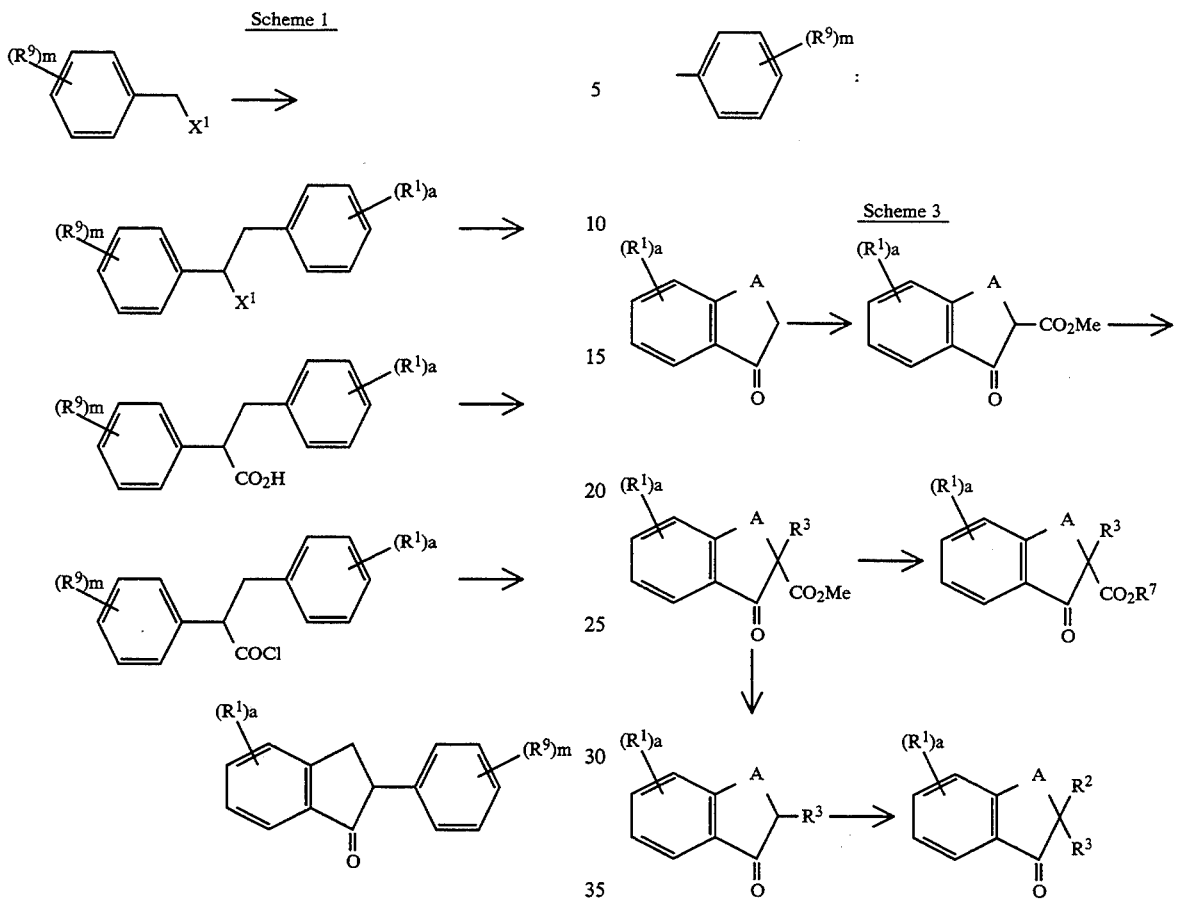

wherein $X^1$ is cyano or $CO_2R$ wherein R is hydrogen or $C_1$–$C_4$ alkyl such as methyl or ethyl.

(Synthesis Process 2)

In case where A is $CH_2$:

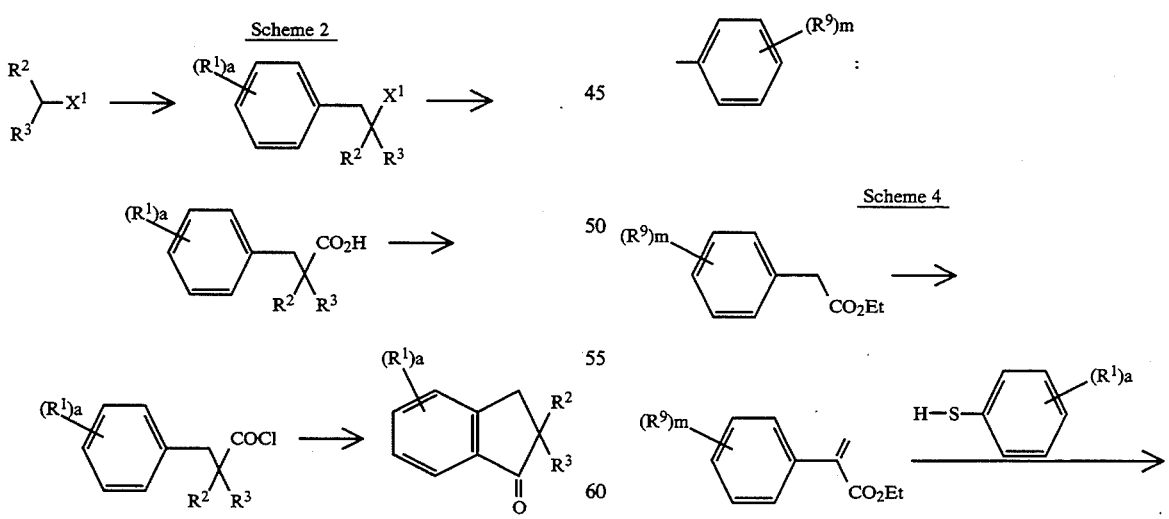

wherein $X^1$ is as defined above.

(Synthesis Process 3)

In case where A is $CH_2$ or $CH_2CH_2$ and each of $R^2$ and $R^3$ is independently a certain group as defined above, other than Scheme 3

(Synthesis Process 4)

In case wherein A is $SCH_2$ and $R^2$ is

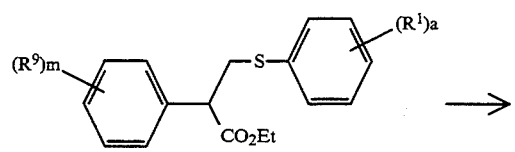

Scheme 4

-continued
Scheme 4
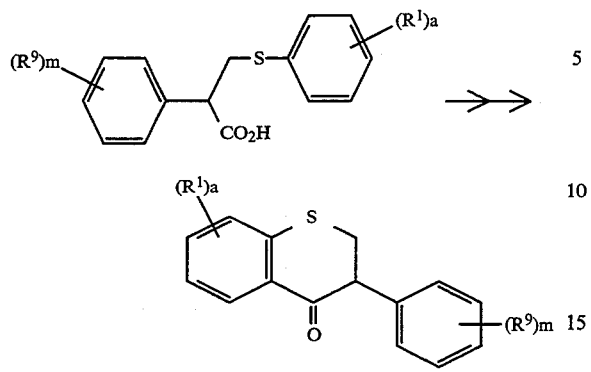
(Synthesis Process 5)
In case where A is oxygen and $R^3$ is a certain group as defined above, other than
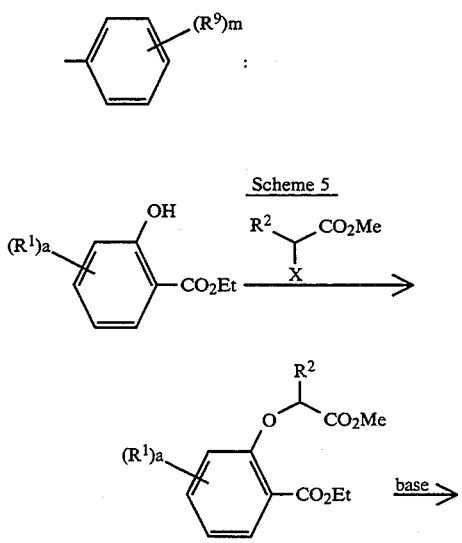
-continued
Scheme 5
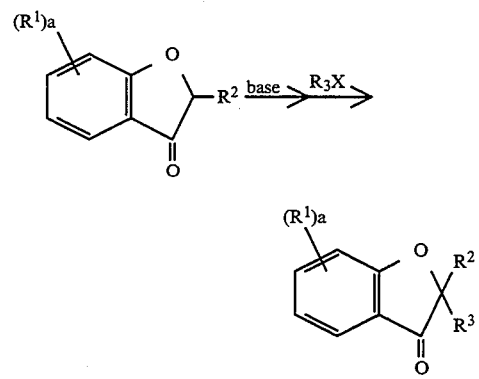
wherein X is as defined above.
(Synthesis Process 6)
In case where A is $CH_2$, $R^2$ is
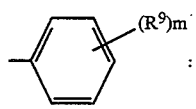
and $R^3$ is a certain group as defined above, other than hydrogen and
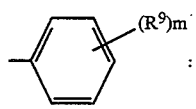
Scheme 6
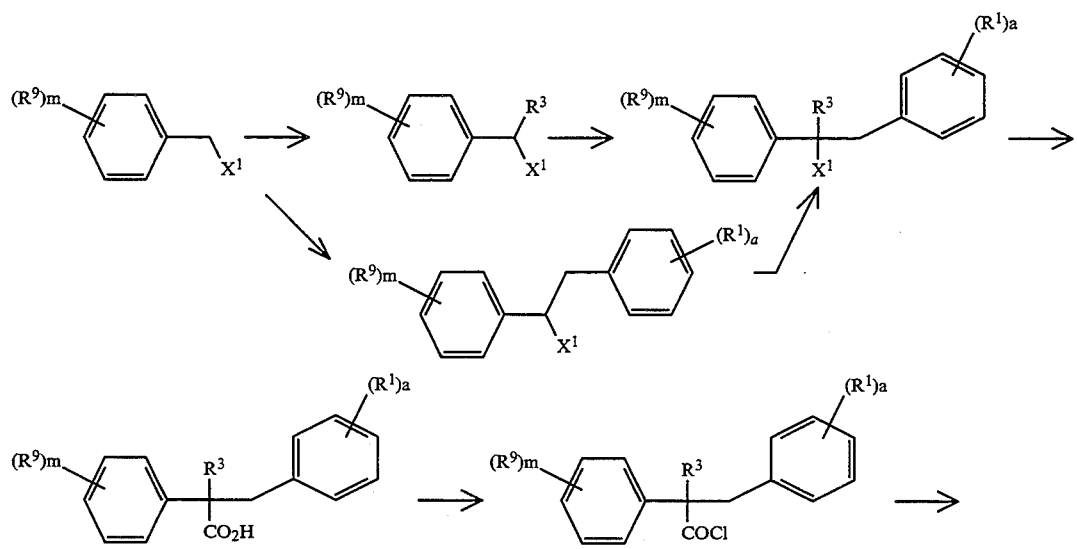

-continued
Scheme 6

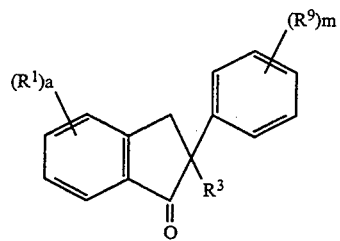

(Synthesis Process 7)

In case where A is $NR^{10}$ (when $R^{10}$ is hydrogen, both of $R^2$ and $R^3$ are not hydrogen):

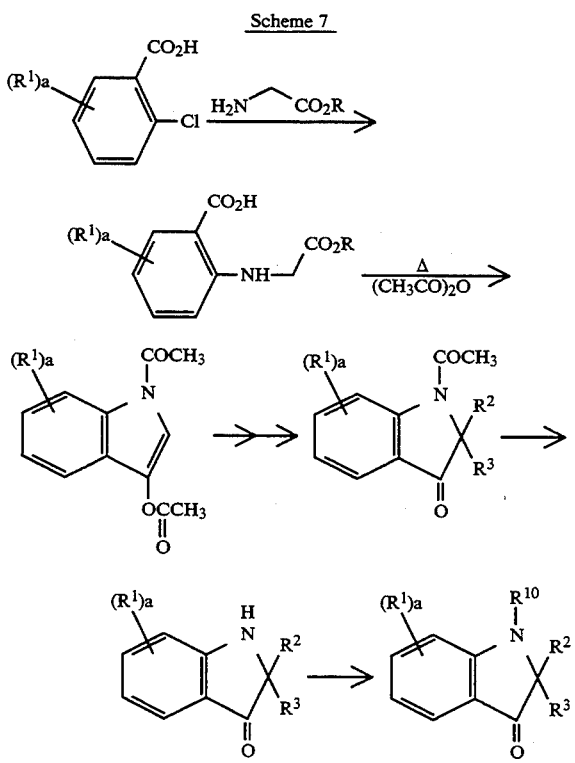

wherein R is as defined above.

(Synthesis Process 8)

In case where A is sulfur and each of $R^2$ and $R^3$ is independently a certain group as defined above, other than

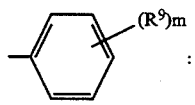

wherein $X^1$ is as defined above.

Scheme 8

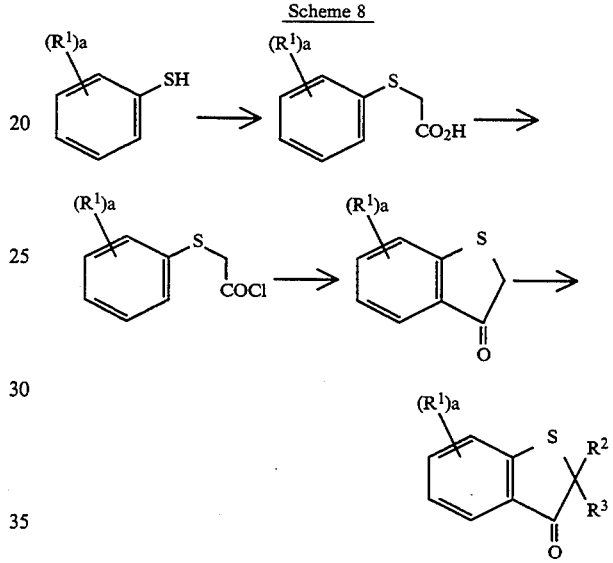

In some cases, the compounds of the present invention may exhibit geometrical isomerism based on C=N linkages or optical isomerism based on asymmetric carbon atoms. These isomers and mixtures thereof are within the scope of the present invention.

The geometrical isomers based on C=N linkages not having the $R^4$ group are distinguished as follows:

In the production of the compounds of the present invention, when a hydrazone compound of the general formula [II], which has been obtained by reacting a ketone compound of the general formula [VIII] with hydrazine, is subjected to chromatography on silica gel with ethyl acetate-hexane (1:3), former and latter eluates are referred to as geometrical isomers a and b. The compounds of the present invention derived from these isomers a and b by the aforedescribed process A, B or C are also designated compounds a and b, respectively.

The compounds of the present invention can exhibit controlling effects against the following insect pests and/or acarine insects:

Hemiptera:

Planthopper (Delphacidae) such as small brown planthopper (*Laodelphax striatellus*), brown rice planthopper (*Nilaparvata lugens*) and white-backed rice planthopper (*Sogatella furcifera*); leafhoppers (Deltocephalidae) such as green rice leafhopper (*Nephotettix cincticeps*) and green rice leafhopper (*Nephotettix virescense*); aphids (Aphididae); stink bugs (Pentatomidae); whiteflies (Aleyrodidae); scales (Coccidae); lace bugs (Tingidae); psyllids (Psyllidae), etc.

Lepidoptera:

Pyralidae such as rice stem borer (*Chilo suppressalis*), rice leafroller (*Cnaphalocrocis medinalis*), eropean corn borer (*Ostrinia nubilalis*), bluegrass webworm (*Parapediasia teterrella*), cotton leafroller (*Notarcha derogata*), indian meal moth (*Plodia interpunctella*), etc.; Noctuidae such as tobacco cutworm (*Spodoptera litura*), rice armyworm (*Pseudaletia separata*), cabbage armyworm (*Mamestra brassicae*), black cutworm (*Agrotis ipsilon*), cabbage looper (*Trichoplusia ni*), Heliothis spp., Helicoverpa spp., etc.; Pieridae such as common cabbage worm (*Pieris rapae crucivora*), etc.; Tortricidae such as Adoxophyes spp. oriental fruit moth (*Grapholita molesta*), codling moth (*Cydia pomonella*), etc.; Carposinidae such as peach fruit moth (*Carposina niponensis*), etc.; Lyonetiidae such as Lyonetia spp., etd.; Lymantriidae such as Lymantria spp., Euproctis spp., etc.; Yponomeutidae such as diamondback moth (*Plutella xylostella*), etc.; Gelechiidae such as pink bollworm (*Pectinophora gossypiella*), etc.; Arctiidae such as fall webworm (*Hyphantria cunea*), etc.; Tineidae such as casemaking clothes moth (*Tinea translucens*), webbing clothes moth (*Tineola bisselliella*), etc.; etc.

Diptera:

Mosquitos (Calicidae) such as common mosquito (*Culex pipiens pallens*) and *Culex tritaeniorhynchus*; Aedes spp. such as *Aedes aegypti* and *Aedes albopictus*; Anopheles spp. such as *Anopheles sinensis*; midges (Chironomidae); house flies (Muscidae) such as housefly (*musca domestica*) and false stablefly (*Muscina stabulans*); Calliphoridae; Sarcophagidae; anthomyiid flies (Anthomyiidae) such as lesser housefly (*Fannia canicularis*), seedcorn maggot (*Hylemya platura*) and onion maggot (*Delia antique*); fruit flies (Tephritidae); small fruit flies (Drosophilidae); moth flies (Psychodidae); blcak flies (Simuliidae); Tabanidae; stable flies (Stomoxyidae), etc.

Coleoptera:

Corn rootworm such as western corn rootworm (*Diabrotica virgifora*) and southern corn rootworm (*Diabrotica undecimpunctata*); scarabs (Scarabaeidae) such as cupreous chafer (*Anomala cuprea*) and soybean beetle (*Anomala rufocuprea*); weevils (Cureulionidae) such as maize weevil (*Sitophilus zeamais*), rice water weevil (*Lissorhoptrus oryzophilus*) and adzuki bean weevil (*Callosobruchys chineneis*); darkling beetles (Tenebrionidae) such as yellow mealworm (*Tenebrio moliter*) and red flour beetles (*Tribolium castaneum*); leaf beetles (Chrysomelidae) such as striped flea beetles (*Phyllotrata striolata*) and cucurbit leaf beetle (*Aulacophora femoralis*); drugstore beetles (Anobiidae); Epilachna spp. such as twenty-eight-spotted ladybirds (*Epilachna vigintioctopunctata*); powder post beetles (Lyctidae); false powder post beetles (Bostrychidae); Cerambycidae; robe beetle (*Paederus fuscipes*), etc.

Dictyoptera:

German cockroach (*Blattella germanica*), smokybrown cockroach (*Periplaneta fuliginosa*), American cockroach (*Periplaneta americana*), brown cockroach (*Periplaneta brunnea*), oriental cockroach (*Blatta orientalis*), etc.

Thysanoptera:

Thrips such as *Thrips palmi* and flower thrips (*Thrips hawaiiensis*), etc.

Hymenoptera:

Ants (Formicidae); hornets (Vespidae); bethylid wasps (Bethylidae); sawflies (Tenthredinidae) such as cabbage sawfly (*Athalia rosae japonensis*), etc.

Orthoptera:

Mole crickets (Gryllotalpidae); grasshoppers (Acrididae), etc.

Aphaniptera:

*Purex irritans*, etc.

Anoplura:

*Pediculus humanus capitis*, *Phthirus pubis*, etc.

Isoptera:

*Reticulitermes speratus*, Formosan subterrauean termite (*Coptotermes formosanus*), etc.

Acarina:

Spider mites (Tetranychidae) such as carmine spider mite (*Tetranychus cinnabarinus*), two-spotted spider mite (*Tetranychus urticae*), Kanzawa spider mite (*Tetranychus kanzawai*) and citrus red mite (*Panonychus citri*) and fruit tree red spider mite (*Panonychus ulmi*), etc.

Further, the compounds of the present invention can exhibit controlling effects against various insect pests and acarine pests having increased resistance to conventional insecticides or acaricides.

On the practical use of the compounds of the present invention as an active ingredient of insecticides or acaricides, they may be employed as such without any other ingredient, but are normally mixed with appropriate additives such as solid carriers, liquid carriers, gaseous carriers and feed to formulate their compositions. When desired or necessary, surfactants and other adjuvants may be further incorporated therein. The compositions may be prepared into any conventional forms such as oil sprays, emulsifiable concentrates, wettable powders, flowable concentrates, granules, dusts, aerosols, fumigants (e.g., fogging agents) and poison baits.

These compositions usually contain the compound(s) of the present invention as an active ingredient in an amount of from about 0.01% to 95% by weight based on the composition.

Examples of the solid carrier which can be used for formulation are fine powders or granules of clays such as kaolin clay, diatomaceous earth, synthetic hydrous silica, bentonite, Fubasami clay and terra alba; talc, ceramics and other inorganic minerals such as sericite, quartz, sulfur, activated carbon, calcium carbonate and hydrous silica; and chemical fertilizers such as ammonium sulfate, ammonium phosphate, ammonium nitrate, urea and ammonium chloride.

Examples of the liquid carrier are water, alcohols such as methanol and ethanol; ketones such as acetone and methyl ethyl ketone; aromatic hydrocarbons such as benzene, toluene, xylene, ethylbenzene and methylnaphthalene; aliphatic hydrocarbons such as hexane, cyclohexane, kerosene and gas oil; esters such as ethyl acetate and butyl acetate; nitriles such as acetonitrile and isobutyronitrile; ethers such as diisopropyl ether and dioxane; acid amides such as N,N-dimethylformamide and N,N-dimethylacetamide; halogenated hydrocarbons such as dichloromethane, trichloroethane and carbon tetrachloride; dimethylsulfoxide; and vegetable oils such as soybean oil and cotton seed oil.

Examples of the gas carrier, i.e., propellant, are freon gas, butane gas, LPG (liquefied petroleum gas), dimethyl ether and carbon dioxide.

Examples of the surfactant are alkylsulfates, alkylsulfonates, alkylarylsulfonates, alkyl aryl ethers and polyoxyethylene derivatives thereof, polyethylene glycol ethers, polyvalent alcohol esters, and sugar alcohol derivatives.

Examples of the adjuvant such as binders and dispersing agents are casein; gelatin; polysaccharides such as starch powders, gum arabic, cellulose derivatives and alginic acid; lignin derivatives; bentonite; sugars; synthetic water-soluble high molecular weight substances such as polyacrylic alcohol, polyvinylpyrrolidone and polyacrylic acid.

Examples of the stabilizer are PAP (acidic isopropyl phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils; surfactants, fatty acids and esters thereof.

The base material for poison baits may contain feed components such as crop powders, essential vegetable oil, sugars and crystalline cellulose; antioxidants such as dibutylhydroxytoluene and nordihydroguaiaretic acid; preservatives such as dehydroacetic acid; feeding error preventing agents such as red pepper powders; incentive flavors such as cheese flavor and onion flavor.

The composition thus obtained may be used as such or after dilution with water. It may also be used in admixture with or used separately but simultaneously with any other active ingredient or composition selected from insecticides, nematocides, acaricides, fungicides, bacteriocides, herbicides, plant growth regulators, synergistic agents, fertilizers, soil conditioners, animal feed and the like.

Examples of the other insecticides and/or acaricides include organophosphorus compounds (e.g., fenitrothion (O,O-dimethyl O-(3-methyl-4-nitrophenyl)phosphorothioate), fenthion (O-O-dimethyl O-[3-methyl-4-(methylthio)phenyl]phosphorothioate), diazinon (O,O-diethyl-O-( 2-isopropyl-6-methylpyrimidin-4-yl)phosphorothioate), chlorpyrifos (O,O-diethyl-O-(3,5,6-trichloro-2-pyridyl)phosphorothioate), acephate (O,S-dimethyl acetylphosphoramidothioate), methidathion (S-2,3-dihydro-5-methoxy-2-oxo-1,3,4-thiadiazol-3-ylmethyl O,O-dimethylphosphorodithioate), disulfoton (O,O-diethyl S-2-ethylthioethyl phosphorothioate), DDVP (2,2-dichlorovinyldimethylphosphate), sulprofos (O-ethyl O-4-(methylthio)phenyl S-propyl phosphorodithioate), cyanophos (O-4-cyanophenyl O,O-dimethyl phosphorothioate), dioxabezofos (2-methoxy-4H-1,3,2-benzodioxaphosphinine-2-sulphide), dimethoate (O,O-dimethyl-S-(N-methylcarbamoylmethyl)dithiophosphate), phenthoate (ethyl 2-dimethoxyphosphinothioylthio(phenyl) acetate), malathion (diethyl (dimethoxyphosphinothioylthio)succinate), trichlorfon (dimethyl 2,2,2-trichloro-1-hydroxyethylphosphonate), azinphos-methyl (S-3,4-dihydro-4-oxo-1,2,3-benzotriazin-3-ylmethyl O,O-dimethylphosphorodithioate), monocrotophos (dimethyl (E)-1-methyl-2-(methylcarbamoyl)vinyl phosphate), ethion (O,O,O',O'-tetraethyl S,S'-methylenebis (phosphorodithioate)), etc.; carbamate derivatives (e.g., BPMC (2-sec-butylphenyl methylcarbamate), benfuracarb (ethyl N-[2,3-dihydro-2,2-dimethylbenzofuran-7-yloxycarbonyl(methyl)aminothio]-N-isopropyl-$\beta$-alaninate), propoxur (2-isopropoxyphenyl N-methylcarbamate), carbosulfan (2,3-dihydro-2,2-dimethyl-7-benzofluranyl[(dibutylamino)thio]methyl carbamate), carbaryl (1-naphthyl-N-methylcarbamate), methomyl (S-methyl-N-[(methylcarbamoyl)oxy]thioacetimidate), ethiofencarb[2-methyl-2-(methylthio)propionaldehyde O-methylcarbamoyloximie], oxamyl (N,N-dimethyl-2-methylcarbamoyloxyimino-2-(methylthio)acetamide), fenothiocarb ((S-4-phenoxybutyl)-N,N-dimethylthiocarbamate), etc.); pyrethroides (e.g., ethofenprox [2-(4-ethoxyphenyl)-2-methylpropyl-3-phenoxybenzyl ether], fenvalerate ((RS)-$\alpha$-cyano-3-phenoxybenzyl (RS)-2-(4-chlorophenyl)-3-methylbutyrate), esfenvalerate [(S)-$\alpha$-cyano-3-phenoxybenzyl (S)-2-(4-chlorophenyl)-3-methylbutyrate], fenpropathrin [(RS)-$\alpha$-cyano-3-phenoxybenzyl 2,2,3,3-tetramethylcycloprppane-carboxylate], cypermethrin [(RS)-$\alpha$-cyano-3-phenoxybenzyl (1RS,3RS)-(1RS,3RS)-3-(2,2-dichlorovinyl)-2,2-dimethylcyclopropanecarboxylate], permethrin (3-phenoxybenzyl (1RS,3RS)-(1RS,3RSJ)-3-(2,2-dichlorovinyl)-2,2-dimethylcyclopropanecarboxylate), cyhalothrin [(R,S)-$\alpha$-cyano-3-phenoxybenzyl (Z)-(1RS,3RS)-3-(2-chloro-3,3,3-trifluoropropenyl)-2,2-dimethylcyclopropanecarboxylate), deltamethrin [(S)-$\alpha$-cyano-m-phenoxybenzyl (1R,3R)-3-(2,2-dibromovinyl)-2-dimethylcyclopropanecarboxylate], cycloprothrin [(RS)-$\alpha$-cyano-3-phenoxybenzyl (RS)-2,2-dichloro-1-(4-ethoxyphenyl)-cyclopropanecarboxylate], fluvalinate ($\alpha$-cyano-3-phenoxybenzyl N-(2-chloro-$\alpha,\alpha,\alpha$-trifluoro-p-tolyl)-D-valinate), bifenthrin (2-methylbiphenyl-3-ylmethyl(z)-(1RS)-cis-3-(2-chloro-3,3,3-trifluoroprop-1-enyl)-2,2-dimethylcyclopropane-carboxylate), acrinathrin ([1R-{(1$\alpha$(S*), 3$\alpha$(Z)}]-2,2-dimethyl-3-[3-oxo-3-(2,2,2-trifluoro-1-(trifluoromethyl)ethoxyl-1-propenyl]cyclopropanecarboxylic acid, cyano(3-phenoxypehnyl)methyl ester), 2-methyl-2-(4-bromodifluoromethoxyphenyl)propyl (3-phenoxybanzyl)ether, tralomethrin [(1R,3S)3[(1'RS)(1',2',2',2'-tetrabromoethyl)]-2,2-dimethylcyclopropane carboxylic acid (S)-$\alpha$-cyano-3-phenoxybenzyl ester), silafluofen (4-ethoxyphenyl [3-(4-fluoro-3-phenoxyphenyl)propyl]dimethylsilane, etc.; thiadiazine derivatives (e.g., buprofezin (2-tert-butylimino-3-isopropyl-5-phenyl-1,3,5-triadiazin-4-one), etc.); nitroimidazolidine derivatives (e.g., imidacloprid [1-(6-chloro-3-pyridylmethyl)-N-nitroimidazolidin-2-ylideneamine], etc.); N-cyanoamidine derivatives (e.g., N-cyano-N'-methyl-N'-(6-chloro-3-pyridylmethyl)acetoamidine, etc.); nereistoxin derivatives (e.g., cartap [S,S'-(2-dimethylaminotrimethylene)-bis(thiocarbamate), thiocyclam (N,N-dimethyl-1,2,3-trithian-5-ylamine), bensultap (S,S'-2-dimethylaminotrimethylene di(benzenethiosulphonate), etc.); halogenated hydrocarbons (e.g., endosulfan (6,7,8,9,10,10-hexachloro-1,5,5a,6,9,9a-hexahydro-6,9-methano-2,4,3-benzodioxathiepin-3-oxide), $\gamma$-BHC (1,2,3,4,5,6-hexachlorocyclohexane), 1,1-bis(chlorophenyl)-2,2,2-trichloroethanol, etc.); benzoylphenylurea derivatives (e.g., chlorfluazuron [1-(3,5-dichloro-4-(3-chloro-5-trifluoromethylpyridin-2-yloxy)phenyl]-3-(2,6-difluorobenzoyl)urea), teflubenzuron [1-(3,5-dichloro-2,4-difluorophenyl)-3-(2,6-difluorobenzoyl)urea], flufenoxuron [1-[4-(2-chloro-4-trifluoromethylphenoxy)-2-fluorophenyl]-3-(2,6-difluorobenzoyl]urea, etc.); formamidine derivatives (e.g., amitraz [N,N'-[(methylimino)-dimethylidyne]-di-2,4-xylidine], chlordimeform [N'-(4-chloro-2-methylphenyl)-N,N-dimethylmethanimidamide], etc.); thiourea derivatives (e.g., diafenthiuron [N-(2,6-diisopropyl-4-phenoxyphenyl)-N'-tert-butylcarbodiimide], etc.); bromopropylate [isopropyl 4,4'-dibromobenzilate], tetradifon [4-chlorophenyl 2,4,5-trichlorophenylsulfone], quinomethionate [S,S-6-methylquinoxalin-2,3-diyldithiocarbonate], propargite [2-[4-(1,1-dimethylethyl)phenoxy]cyclohexyl 2-propynyl sulfite], febutatin oxide [hexakis(2-methyl-2-phenylpropyl)distannoxane], hexythiazox[(4RS,5RS)-5-(4-chlorophenyl)-N-chlorohexyl-4-methyl-2-oxo-1,3-thiazolidine-3-carboxamide], clofentezine[3,6-bis(2-chlorophenyl)-1,2,4,5-tetrazine], pyridaben [2-tert-butyl-5-[4-tert-butylbenzylthio]-4-chloropyridazin-3(2H)-one], fenpyroximate [tert-butyl (E)-4-[(1,3)- dimethyl-5-phenoxypyrazole-4-yl)methylene aminooxymethyl]benzoate], tebufenpyrad [N-(4-tert-butylbenzyl)-4-chloro-3-ethyl-1-methyl-5-pyrazole carboxamide], polynactins [tetranactin, dinactin, trinactin], milbemectin, avermectin, ivermectin azadirachtin [AZAD], pyrimidifen [5-chloro-N-[2-{4-(2-ethoxyethyl)-2,3-dimethylphenoxy}ethyl]-6-ethylpyrimidin-4-amine, etc.

For the purpose of controlling insect pests and/or acarine pests in agricultural fields, the compounds of the present invention may be applied to the insect pests and/or acarine pests or the locus where the insect pests and/or acarine pests inhabit, generally in an amount of from about 0.1 to 100 g per 10 ares. When the compounds of the present invention is applied in the form of an emulsifiable concentrate, wettable powder, flowable concentrate or the like, after dilution with water, its concentration may be from about 0.1 to 500 ppm. Granules, dusts or the like may be used as such, i.e., without any dilution. For the purpose of preventing infectious diseases caused by insect pests and/or acarine pests, the compounds of the present invention may be used in the form of an emulsifiable concentrate, wettable powder, flowable concentrate or the like, after dilution with water in a concentration of from about 0.1 to 500 ppm, or may be used in the form of an oil, aerosol, fumigant, poison baits or the like, without any dilution.

The doses and concentrations may be increased or decreased, irrespective of the general ranges as set forth above, depending upon kinds of formulations, the season and method of application, place to be applied, kinds of insect pests and/or acarine pests to be controlled, conditions of damage and the like.

The present invention will be further illustrated by way of the following Production Examples, Formulation Examples and Test Examples, which are not to be construed to limit the scope thereof.

Production Example 1

A mixture of 5-chloro-2-(4-fluorophenyl)-2,3-dihydro-1H-inden-1-ylidene-hydrazone (0.3 g) and N,N-dimethylacetamide dimethylacetal (0.44 g) was heated under reflux in an atmosphere of nitrogen gas for 4 hours. After left to stand for cooling to room temperature, the reaction mixture was diluted with dichloromethane (5 ml), washed with water, dried over anhydrous magnesium sulfate and concentreated under reduced pressure. The resulting oil was subjected to chromatography on silica gel to give 5-chloro-2-(4-fluorophenyl)-2,3-dihydro-1-[1-(dimethylamino)ethylidenehydrazono]-1H-indene (Compound No. 60; yield, 0.27 g) as pale yellow crystals, m.p., 133.6° C.

Production Example 2

A mixture of 5-chloro-2-(4-fluorophenyl)-2,3-dihydro-1H-inden-1-ylidene-hydrazone (0.3 g) and N,N-dimethylformamide dimethylacetal (0.39 g) was heated under reflux in an atmosphere of nitrogen gas for 5 hours. The reaction mixture was subjected to the same post-treatment as described in Production Example 1 to give the desired compound, 5-chloro-2-(4-fluorophenyl)-2,3-dihydro-1-[1-(dimethylamino)methylidenehydrazono]-1H-indene (0.25 g; Compound No. 346) as white crystals, m.p., 134.4° C.

Production Example 3

A solution of 5-chloro-2-(4-chlorophenyl)-2-methyl-2,3-dihydro-1H-inden-1-one (2.0 g), hydrazine monohydrate (1.0 g) and acetic acid (catalytic amount) in ethanol (10 ml) was heated under reflux for 24 hours. After left to stand for cooling to room temperature, the reaction mixture was concentrated under reduced pressure until about 6 ml of ethanol was removed therefrom. The concentrate was diluted with dichloromethane (15 ml), washed with water, dried over anhydrous magnesium sulfate and concentrated under reduced pressure. The resulting oil was subjected to chromatography on silica gel to give the corresponding hydrazones a (1.2 g) and b (0.4 g). The hydrazones a and b thus obtained were separately mixed with 1 g and 0.5 g of N,N-dimethylacetamide dimethylacetal, respectively, and the resulting mixtures were treated by the same procedures as described in Production Example 1 to give 5-chloro-2-(4-chlorophenyl)-2-methyl-2,3-dihydro-1-[(dimethylamino)ethylidenehydrazono]-1H-indene (Compound Nos. 270a and 270b; yield, 1.0 g and 0.4 g, respectively) as pale yellow crystals.

Compound No. 270a: m.p., 134.8° C.,
$^1$H-NMR (CDCl$_3$, TMS) δ(ppm) 7.76 (d, 1H), 7.12–7.32 (m, 6H), 3.22 (d,1H), 3.09 (d,1H), 2.67 (s, 6H), 2.17 (s, 3H), 1.83(s, 3H).

Compound No. 270b: m.p., 110.9° C.,
$^1$H-NMR (CDCl$_3$, TMS) δ(ppm) 8.70 (d, 1H), 7.16–7.32 (m, 6H), 3.40 (d,1H), 3.21 (d,1H), 3.08 (s, 6H), 2.20 (s, 3H), 1.70 (s, 3H).

Production Example 4

To a solution of 5-chloro-2-(4-chlorophenyl)-2,3-dihydro-1H-inden-1ylidenehydrazone (2.0 g) and triethylamine (0.8 g) in dichloromethane (20 ml) was added dropwise acetic anhydrate (0.8 g) under ice-cooling, followed by stirring at room temperature for 5 hours. The reaction mixture was diluted with dichloromethane (20 ml), poured into ice-water and extracted with dichloromethane. The organic layer was dried over anhydrous magnesium sulfate and concentrated under reduced pressure. The resulting crystals were washed with hexane and dried to give the corresponding acethylhydrazone (yield, 2.2 g), m.p., 183.5° C.

A solution of the acethylhydrazone (2.2 g) and phosphorous oxychloride (1.1 g) in benzene was heated under reflux for 6 hours. After cooling to room temperature, the reaction mixture was poured into ice-water and extracted with ethyl acetate. The extract was washed with 10% aqueous sodium bicarbonate and then water, dried over anhydrous magnesium sulfate and concentrated under reduced pressure. The resulting residue was subjected to chromatography on silica gel to give 5-chloro-2-(4-chlorophenyl)-2,3-dihydro-1'-chloroethylidene-hydrazono)-1H-indene (yield, 1.2g), $n_d^{23.0}$, 1.6190.

$^1$H-NMR(CDCl$_3$, TMS) δ(ppm): 7.88 (d,1H), 7.38 (m, 2H), 7.23 (d, 2H), 7.02 (d, 2H), 4.35 (dd, 1H), 3.60 (dd, 1H), 2.97 (dd, 1H), 2.14 (s, 3H)

To a solution of 5-chloro-2-(4-chlorophenyl)-2,3-dihydro-1'-chloroethylidene-hydrazono)-1H-indene (1.2 g benzene (5 ml) under vigrous stirring was added dropwise 50% aqueous dimethylamine (5 ml) under ice-cooling, followed by stirring at room temperature overnight. The reaction mixture was diluted with benzene (20 ml), poured into ice-water and extracted with benzene. The extract was washed with water, dried over anhydrous magnesium sulfate and concentrated under reduced pressure. The resulting residue was crystallized with ethyl acetate to give 5-chloro-2-(4-chlorophenyl)-2,3-dihydro-1'-[(dimethylamino)ethylidenehydrono]-1H-indene (Compound No. 8; yield, 0.3 g), m.p., 138.8° C.

¹H-NMR (CDCl₃, TMS) δ(ppm): 7.76 (d, 1H), 7.28 (m, 2H), 7.15 (d, 2H), 7.06 (d, 2H), 4.57 (dd, 1h), 3.56 (dd, 1H), 2.88 (dd, 2H), 2.86 (s, 6H), 2.19 (s, 3H).

Production Example 5

To a solution of hydrazine monohydrate (0.2 ml) in methanol (7 ml) was added N,N-dimethylacetamidedimethylacetal (0.6 ml) at room temperature, and the reaction was allowed to proceed at room temperature for 30 minutes, followed by heating at reflux for 15 minutes, resulting in a solution of N,N-dimethylacetamidehydrazone in methanol. A portion of this solution was concentrated and subjected to the measurement of NMR spectra. ¹H-NMR (CDCl₃, TMS) δ(ppm): 1.88 (s, 6H), 2.37 (s, 3H).

To a solution of the N,N-dimethylacetamidehydrazone in methanol was added 5-chloro-2-(3-chlorophenyl)indanone (0.55 g) at room temperature, and the mixture was heated at reflux for 12 hours. The resulting reaction mixture was concentrated and subjected to chromatography on silica gel to give 5-chloro-2-(3-chlorophenyl)-2,3-dihydro-1-[1-(dimethylamino)ethylidenehydrazono]-1H-indene (Compound No. 441; yield, 0.26 g), m.p., 136.7° C.

Various compounds of the present invention which can be obtained in the same manner as described above are shown in Table 1 to 17.

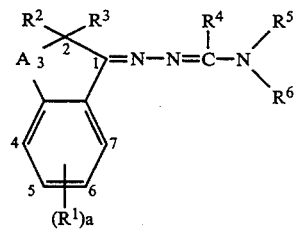

TABLE 1

(A=CH₂)

| Compound No. | R¹ | R² | R³ | R⁴ | R⁵ | R⁶ | Physical properties |
|---|---|---|---|---|---|---|---|
| 1 | 5-Cl | Ph | H | CH₃ | CH₃ | CH₃ | m.p., 137.7° C. |
| 2 | 5-Cl | Ph | H | CH₃ | C₂H₅ | CH₃ | |
| 3 | 5-Cl | Ph | H | CH₃ | C₂H₅ | C₂H₅ | |
| 4 | 5-Cl | Ph | H | CH₃ | i-C₃H₇ | H | oily solid |
| 5 | 5-Cl | Ph | H | CH₃ | t-C₄H₉ | H | |
| 6 | 5-Cl | Ph | H | CH₃ | CH₂CF₃ | H | oily solid |
| 7 | 5-Cl | 4-Cl—Ph | H | CH₃ | H | CH₃ | |
| 8 | 5-Cl | 4-Cl—Ph | H | CH₃ | CH₃ | CH₃ | m.p., 138.8° C. |
| 9 | 5-Cl | 4-Cl—Ph | H | CH₃ | C₂H₅ | CH₃ | m.p., 129.6° C. |
| 10 | 5-Cl | 4-Cl—Ph | H | CH₃ | n-C₃H₇ | CH₃ | m.p., 97.7° C. |
| 11 | 5-Cl | 4-Cl—Ph | H | CH₃ | i-C₃H₇ | CH₃ | |
| 12 | 5-Cl | 4-Cl—Ph | H | CH₃ | n-C₄H₉ | CH₃ | $n_D^{23.0}$ 1.6202 |
| 13 | 5-Cl | 4-Cl—Ph | H | CH₃ | t-C₄H₉ | CH₃ | |
| 14 | 5-Cl | 4-Cl—Ph | H | CH₃ | i-C₄H₉ | CH₃ | $n_D^{23.0}$ 1.6234 |
| 15 | 5-Cl | 4-Cl—Ph | H | CH₃ | sec-C₄H₉ | CH₃ | |
| 16 | 5-Cl | 4-Cl—Ph | H | CH₃ | n-C₅H₁₁ | CH₃ | |
| 17 | 5-Cl | 4-Cl—Ph | H | CH₃ | CF₃ | CH₃ | |
| 18 | 5-Cl | 4-Cl—Ph | H | CH₃ | CF₂Br | CH₃ | |
| 19 | 5-Cl | 4-Cl—Ph | H | CH₃ | CF₂H | CH₃ | |
| 20 | 5-Cl | 4-Cl—Ph | H | CH₃ | CF₂CF₂H | CH₃ | |
| 21 | 5-Cl | 4-Cl—Ph | H | CH₃ | CH₂CF₃ | CH₃ | |
| 22 | 5-Cl | 4-Cl—Ph | H | CH₃ | CH₂CHhd 2CF₃ | CH₃ | |
| 23 | 5-cl | 4-Cl—Ph | H | CH₃ | CH(CH₃)CF₃ | CH₃ | |
| 24 | 5-Cl | 4-Cl—Ph | H | CH₃ | CH₂CF₂CF₂CF₃ | CH₃ | |
| 25 | 5-Cl | 4-Cl—Ph | H | CH₃ | CH(CH₃)CF₂CF₂CF₃ | CH₃ | |
| 26 | 5-Cl | 4-Cl—Ph | H | CH₃ | CH₂CH=CH₂ | CH₃ | $n_D^{24.0}$ 1.6431 |
| 27 | 5-Cl | 4-Cl—Ph | H | CH₃ | CH₂CH=CHCH₃ | CH₃ | |
| 28 | 5-Cl | 4-Cl—Ph | H | CH₃ | CH₂CF=CHCH₃ | CH₃ | |
| 29 | 5-Cl | 4-Cl—Ph | H | CH₃ | CH₂CH=CHCH₂CH₃ | CH₃ | |
| 30 | 5-Cl | 4-Cl—Ph | H | CH₃ | CH₂C≡CH | CH₃ | m.p., 109.2° C. |
| 31 | 5-Cl | 4-Cl—Ph | B | CH₃ | CH₂C≡CCH₃ | CH₃ | |
| 32 | 5-Cl | 4-Cl—Ph | H | CH₃ | CH₂C≡CCF₂Br | CH₃ | |
| 33 | 5-Cl | 4-Cl—Ph | H | CH₃ | CH₂C≡CCH₂CF₃ | CH₃ | |
| 34 | 5-Cl | 4-Cl—Ph | H | CH₃ | C₂H₅ | H | |
| 35 | 5-Cl | 4-Cl—Ph | H | CH₃ | n-C₃H₇ | H | |
| 36 | 5-Cl | 4-Cl—Ph | H | CH₃ | i-C₃H₇ | H | |
| 37 | 5-Cl | 4-Cl—Ph | H | CH₃ | n-C₄H₉ | H | |
| 38 | 5-Cl | 4-Cl—Ph | H | CH₃ | t-C₄H₉ | H | |
| 39 | 5-Cl | 4-Cl—Ph | H | CH₃ | sec-C₄H₉ | H | |
| 40 | 5-Cl | 4-Cl—Ph | H | CH₃ | CH₂CF₃ | H | |
| 41 | 5-Cl | 4-Cl—Ph | H | CH₃ | CH₂CF₂CF₃ | H | |
| 42 | 5-Cl | 4-Cl—Ph | H | CH₃ | CH(CH₃)CF₂CF₃ | H | |
| 43 | 5-Cl | 4-Cl—Ph | H | CH₃ | CH₂CH=CH₂ | H | |
| 44 | 5-Cl | 4-Cl—Ph | H | CH₃ | CH₂C≡CH | H | |
| 45 | 5-Cl | 4-Cl—Ph | H | CH₃ | C₂H₅ | C₂H₅ | m.p., 121.9° C. |
| 46 | 5-Cl | 4-Cl—Ph | H | CH₃ | n-C₃H₇ | C₂H₅ | $n_D^{23.2}$ 1.6290 |
| 47 | 5-Cl | 4-Cl—Ph | H | CH₃ | i-C₃H₇ | C₂H₅ | |
| 48 | 5-Cl | 4-Cl—Ph | H | CH₃ | CF₂H | C₂H₅ | |
| 49 | 5-Cl | 4-Cl—Ph | H | CH₃ | CH₂CF₃ | C₂H₅ | |
| 50 | 5-Cl | 4-Cl—Ph | H | CH₃ | CH₂CH=CH₂ | C₂H₅ | |
| 51 | 5-Cl | 4-Cl—Ph | H | CH₃ | CH₂C≡CH₃ | C₂H₅ | |
| 52 | 5-Cl | 4-Cl—Ph | H | CH₃ | n-C₃H₇ | n-C₃H₇ | |
| 53 | 5-Cl | 4-Cl—Ph | H | CH₃ | i-C₃H₇ | n-C₃H₇ | |
| 54 | 5-Cl | 4-Cl—Ph | H | CH₃ | CH₂CF₃ | n-C₃H₇ | |

TABLE 1-continued (A=CH₂)

| Compound No. | R¹ | R² | R³ | R⁴ | R⁵ | R⁶ | Physical properties |
|---|---|---|---|---|---|---|---|
| 55 | 5-Cl | 4-Cl—Ph | H | CH₃ | i-C₃H₇ | i-C₃H₇ | |
| 56 | 5-Cl | 4-Cl—Ph | H | CH₃ | CH₂CF₃ | i-C₃H₇ | |
| 57 | 5-Cl | 4-F—Ph | H | CH₃ | CH₂CF₃ | H | |
| 58 | 5-Cl | 4-F—Ph | H | CH₃ | i-C₃H₇ | H | |
| 59 | 5-Cl | 4-F—Ph | H | CH₃ | t-C₄H₉ | H | |
| 60 | 5-Cl | 4-F—Ph | H | CH₃ | CH₃ | CH₃ | m.p., 133.6° C. |
| 61 | 5-Cl | 4-F—Ph | H | CH₃ | C₂H₅ | CH₃ | |
| 62 | 5-Cl | 4-F—Ph | H | CH₃ | i-C₃H₇ | CH₃ | |
| 63 | 5-Cl | 4-F—Ph | H | CH₃ | C₂H₅ | C₂H₅ | |
| 64 | 5-Cl | 4-Br—Ph | H | CH₃ | CH₃ | CH₃ | m.p., 154.1° C. |
| 65 | 5-Cl | 4-Br—Ph | H | CH₃ | C₂H₅ | C₂H₅ | |
| 66 | 5-Cl | 4-Br—Ph | H | CH₃ | t-C₄H₉ | H | |
| 67 | 5-Cl | 4-OCF₂H—Ph | H | CH₃ | CH₃ | CH₃ | |
| 68 | 5-Cl | 4-OCF₂H—Ph | H | CH₃ | C₂H₅ | CH₃ | |
| 69 | 5-Cl | 4-OCF₂H—Ph | H | CH₃ | C₂H₅ | C₂H₅ | |
| 70 | 5-Cl | 4-OCF₂H—Ph | H | CH₃ | i-C₃H₇ | H | |
| 71 | 5-Cl | 4-OCF₂H—Ph | H | CH₃ | t-C₄H₉ | H | |
| 72 | 5-Cl | 4-OCF₂CF₂H—Ph | H | CH₃ | CH₃ | CH₃ | |
| 73 | 5-Cl | 4-OCF₂CF₂H—Ph | H | CH₃ | CH₃ | CH₃ | |
| 74 | 5-Cl | 4-OCF₃—Ph | H | CH₃ | CH₃ | CH₃ | |
| 75 | 5-Cl | 4-OCF₃—Ph | H | CH₃ | C₂H₅ | CH₃ | |
| 76 | 5-Cl | 4-OCF₃—Ph | H | CH₃ | C₂H₅ | C₂H₅ | |
| 77 | 5-Cl | 4-OCF₃—Ph | H | CH₃ | t-C₄H₉ | H | |
| 78 | 5-Cl | 4-OCH₃—Ph | H | CH₃ | CH₃ | CH₃ | |
| 79 | 5-Cl | 4-SCH₃—Ph | H | CH₃ | CH₃ | CH₃ | |
| 80 | 5-Cl | 4-NO₂—Ph | H | CH₃ | CH₃ | CH₃ | |
| 81 | 5-Cl | 4-CN—Ph | H | CH₃ | CH₃ | CH₃ | |
| 82 | 5-F | Ph | H | CH₃ | CH₃ | CH₃ | |
| 83 | 5-F | Ph | H | CH₃ | C₂H₅ | CH₃ | |
| 84 | 5-F | Ph | H | CH₃ | C₂H₅ | C₂H₅ | |
| 85 | 5-F | Ph | H | CH₃ | i-C₃H₇ | CH₃ | |
| 86 | 5-F | Ph | H | CH₃ | i-C₃H₇ | H | |
| 87 | 5-F | Ph | H | CH₃ | t-C₄H₉ | H | |
| 88 | 5-F | Ph | H | CH₃ | CH₂CF₃ | H | |
| 89 | 5-F | 4-Cl—Ph | H | CH₃ | CH₃ | CH₃ | m.p., 114.2° C. |
| 90 | 5-F | 4-Cl—Ph | H | CH₃ | C₂H₅ | CH₃ | |
| 91 | 5-F | 4-Cl—Ph | H | CH₃ | C₂H₅ | C₂H₅ | viscous liquid |
| 92 | 5-F | 4-Cl—Ph | H | CH₃ | i-C₃H₇ | H | oily solid |
| 93 | 5-F | 4-Cl—Ph | H | CH₃ | t-C₄H₉ | H | |
| 94 | 5-F | 4-Cl—Ph | H | CH₃ | CH₂CF₃ | H | |
| 95 | 5-F | 4-F—Ph | H | CH₃ | CH₃ | CH₃ | m.p., 128.4° C. |
| 96 | 5-F | 4-F—Ph | H | CH₃ | CH₃ | C₂H₅ | |
| 97 | 5-F | 4-F—Ph | H | CH₃ | C₂H₅ | C₂H₅ | |
| 98 | 5-F | 4-F—Ph | H | CH₃ | i-C₃H₇ | H | |
| 99 | 5-F | 4-F—Ph | H | CH₃ | t-C₄H₉ | H | |
| 100 | 5-F | 4-Br—Ph | H | CH₃ | CH₃ | CH₃ | |
| 101 | 5-F | 4-Br—Ph | H | CH₃ | t-C₄H₉ | H | |
| 102 | 5-F | 4-CF₃—Ph | H | CH₃ | CH₃ | CH₃ | |
| 103 | 5-F | 4-CF₃—Ph | H | CH₃ | CH₃ | CH₃ | |
| 104 | 5-F | 4-CF₃—Ph | H | CH₃ | C₂H₅ | C₂H₅ | |
| 105 | 5-F | 4-CF₃—Ph | H | CH₃ | t-C₄H₉ | H | |
| 106 | 5-F | 4-CH₃—Ph | H | CH₃ | CH₃ | CH₃ | |
| 107 | 5-F | 4-CH₃—Ph | H | CH₃ | CH₃ | C₂H₅ | |
| 108 | 5-F | 4-CH₃—Ph | H | CH₃ | C₂H₅ | C₂H₅ | |
| 109 | 5-F | 4-CH₃—Ph | H | CH₃ | t-C₄H₉ | H | |
| 110 | 5-F | 4-OCF₃—Ph | H | CH₃ | CH₃ | CH₃ | |
| 111 | 5-F | 4-OCF₃—Ph | H | CH₃ | C₂H₅ | CH₃ | |
| 112 | 5-F | 4-OCF₃—Ph | H | CH₃ | C₂H₅ | C₂H₅ | |
| 113 | 5-F | 4-OCF₃—Ph | H | CH₃ | i-C₃H₇ | H | |
| 114 | 5-F | 4-OCF₃—Ph | H | CH₃ | t-C₄H₉ | H | |
| 115 | 5-F | 4-OCF₂H—Ph | H | CH₃ | CH₃ | CH₃ | |
| 116 | 5-F | 4-OCF₂H—Ph | H | CH₃ | C₂H₅ | CH₃ | |
| 117 | 5-F | 4-OCF₂H—Ph | H | CH₃ | C₂H₅ | C₂H₅ | |
| 118 | 5-F | 4-OCF₂H—Ph | H | CH₃ | i-C₃H₇ | H | |
| 119 | 5-F | 4-OCF₂H—Ph | H | CH₃ | t-C₄H₉ | H | |
| 120 | 5-F | 4-OCF₂CF₂H—Ph | I | CH₃ | CH₃ | CH₃ | |
| 121 | 5-F | 4-OCF₂CF₂H—Ph | H | CH₃ | t-C₄H₉ | H | |
| 122 | 5-F | 4-OCH₂CF₃—Ph | H | CH₃ | CH₃ | CH₃ | |
| 123 | 5-F | 4-OCH₂CF₃—Ph | H | CH₃ | t-C₄H₉ | H | |
| 124 | 5-F | 4-OCH₃—Ph | H | CH₃ | CH₃ | CH₃ | |
| 125 | 5-F | 4-SCH₃—Ph | H | CH₃ | CH₃ | CH₃ | |
| 126 | 5-F | 4-CN—Ph | H | CH₃ | CH₃ | CH₃ | |
| 127 | 5-F | 4-NO₂—Ph | H | CH₃ | CH₃ | CH₃ | |
| 128 | 5-Br | Ph | H | CH₃ | CH₃ | CH₃ | |
| 129 | 5-Br | Ph | H | CH₃ | C₂H₅ | CH₃ | |
| 130 | 5-Br | Ph | H | CH₃ | C₂H₅ | C₂H₅ | |
| 131 | 5-Br | Ph | H | CH₃ | t-C₄H₉ | H | |
| 132 | 5-Br | 4-Cl—Ph | H | CH₃ | CH₃ | CH₃ | m.p., 133.9° C. |
| 133 | 5-Br | 4-Cl—Ph | H | CH₃ | t-C₄H₉ | H | |

TABLE 1-continued (A=CH$_2$)

| Compound No. | R$^1$ | R$^2$ | R$^3$ | R$^4$ | R$^5$ | R$^6$ | Physical properties |
|---|---|---|---|---|---|---|---|
| 134 | 5-Br | 4-F—Ph | H | CH$_3$ | CH$_3$ | CH$_3$ | |
| 135 | 5-Br | 4-Br—Ph | H | CH$_3$ | CH$_3$ | CH$_3$ | |
| 136 | 5-Br | 4-OCF$_2$—Ph | I | CH$_3$ | CH$_3$ | CH$_3$ | |
| 137 | 5-Br | 4-OCF$_2$H—Ph | H | CH$_3$ | CH$_3$ | CH$_3$ | |
| 138 | 5-Br | 4-OCF$_2$CF$_2$H—Ph | H | CH$_3$ | CH$_3$ | CH$_3$ | |
| 139 | 5-Br | 4-OCF$_2$CF$_3$—Ph | H | CH$_3$ | CH$_3$ | CH$_3$ | |
| 140 | 5-Br | 4-OCH$_3$—Ph | H | CH$_3$ | CH$_3$ | CH$_3$ | |
| 141 | 5-Br | 4-SCH$_3$—Ph | H | CH$_3$ | CH$_3$ | CH$_3$ | |
| 142 | 5-Br | 4-CN—Ph | H | CH$_3$ | CH$_3$ | CH$_3$ | |
| 143 | 5-Br | 4-NO$_2$—Ph | H | CH$_3$ | CH$_3$ | CH$_3$ | |
| 144 | 5-OCH$_3$ | Ph | H | CH$_3$ | CH$_3$ | CH$_3$ | |
| 145 | 5-OCH$_3$ | 4-Cl—Ph | H | CH$_3$ | CH$_3$ | CH$_3$ | m.p., 138.2° C. |
| 146 | 5-OCH$_3$ | 4-F—Ph | H | CH$_3$ | CH$_3$ | CH$_3$ | m.p., 141.3° C. |
| 147 | 5-SCH$_3$ | Ph | H | CH$_3$ | CH$_3$ | CH$_3$ | |
| 148 | 5-SCH$_3$ | 4-Cl—Ph | H | CH$_3$ | CH$_3$ | CH$_3$ | |
| 149 | 5-SCH$_3$ | 4-F—Ph | H | CH$_3$ | CH$_3$ | CH$_3$ | |
| 150 | 5-CF$_3$ | Ph | H | CH$_3$ | CH$_3$ | CH$_3$ | |
| 151 | 5-CF$_3$ | Ph | H | CH$_3$ | C$_2$H$_5$ | CH$_3$ | |
| 152 | 5-CF$_3$ | Ph | H | CH$_3$ | C$_2$H$_5$ | C$_2$H$_5$ | |
| 153 | 5-CF$_3$ | Ph | H | CH$_3$ | i-C$_3$H$_7$ | H | |
| 154 | 5-CF$_3$ | Ph | H | CH$_3$ | t-C$_4$H$_9$ | H | |
| 155 | 5-CF$_3$ | 4-Cl—Ph | H | CH$_3$ | CH$_3$ | CH$_3$ | |
| 156 | 5-CF$_3$ | 4-Cl—Ph | H | CH$_3$ | C$_2$H$_5$ | CH$_3$ | |
| 157 | 5-CF$_3$ | 4-Cl—Ph | H | CH$_3$ | C$_2$H$_5$ | C$_2$H$_5$ | |
| 158 | 5-CF$_3$ | 4-Cl—Ph | H | CH$_3$ | i-C$_3$H$_7$ | H | |
| 159 | 5-CF$_3$ | 4-Cl—Ph | H | CH$_3$ | t-C$_4$H$_9$ | H | |
| 160 | 5-CF$_3$ | 4-F—Ph | H | CH$_3$ | CH$_3$ | CH$_3$ | |
| 161 | 5-CF$_3$ | 4-F—Ph | H | CH$_3$ | CH$_3$ | C$_2$H$_5$ | |
| 162 | 5-CF$_3$ | 4-F—Ph | H | CH$_3$ | C$_2$H$_5$ | C$_2$H$_5$ | |
| 163 | 5-CF$_3$ | 4-F—Ph | H | CH$_3$ | i-C$_3$H$_7$ | H | |
| 164 | 5-CF$_3$ | 4-F—Ph | H | CH$_3$ | t-C$_4$H$_9$ | H | |
| 165 | 5-CF$_3$ | 4-Br—Ph | H | Cli3 | CH$_3$ | CH$_3$ | |
| 166 | 5-CF$_3$ | 4-CH$_3$—Ph | H | CH$_3$ | CH$_3$ | CH$_3$ | |
| 167 | 5-CF$_3$ | 4-CF$_3$—Ph | H | CH$_3$ | CH$_3$ | CH$_3$ | |
| 168 | 5-CF$_3$ | 4-OCF$_2$H—Ph | H | CH$_3$ | CH$_3$ | CH$_3$ | |
| 169 | 5-CF$_3$ | 4-OCF$_2$H—Ph | H | CH$_3$ | C$_2$H$_5$ | CH$_3$ | |
| 170 | 5-CF$_3$ | 4-OCF$_2$H—Ph | H | CH$_3$ | C$_2$H$_5$ | C$_2$H$_5$ | |
| 171 | 5-CF$_3$ | 4-OCF$_2$H—Ph | H | CH$_3$ | t-C$_4$H$_9$ | H | |
| 172 | 5-CF$_3$ | 4-OCF$_3$—PH | H | CH$_3$ | CH$_3$ | CH$_3$ | |
| 173 | 5-CF$_3$ | 4-OCF$_3$—Ph | H | CH$_3$ | CH$_3$ | C$_2$H$_5$ | |
| 174 | 5-CF$_3$ | 4-OCF$_2$—Ph | H | CH$_3$ | C$_2$H$_5$ | C$_2$H$_5$ | |
| 175 | 5-CF$_3$ | 4-OCF$_3$—Ph | H | CH$_3$ | t-C$_4$H$_9$ | H | |
| 176 | 5-CF$_3$ | 4-OCF$_2$CF$_2$H—Ph | H | CH$_3$ | CH$_3$ | CH$_3$ | |
| 177 | 5-CF$_3$ | 4-OCH$_2$CF$_3$—Ph | H | CH$_3$ | CH$_3$ | CH$_3$ | |
| 178 | 5-CF$_3$ | 4-OCH$_3$—Ph | H | CH$_3$ | CH$_3$ | CH$_3$ | |
| 179 | 5-CF$_3$ | 4-SCH$_3$—Ph | H | CH$_3$ | CH$_3$ | CH$_3$ | |
| 180 | 5-CF$_3$ | 4-CN—Ph | H | CH$_3$ | CH$_3$ | CH$_3$ | |
| 181 | 5-CF$_3$ | 4-NO$_2$—Ph | H | CH$_3$ | CH$_3$ | CH$_3$ | |
| 182 | 5-OCF$_3$ | Ph | H | CH$_3$ | CH$_3$ | CH$_3$ | |
| 183 | 5-OCF$_3$ | Ph | H | CH$_3$ | C$_2$H$_5$ | CH$_3$ | |
| 184 | 5-OCF$_3$ | Ph | H | CH$_3$ | t-C$_4$H$_9$ | H | |
| 185 | 5-OCF$_3$ | 4-Cl—Ph | H | CH$_3$ | CH$_3$ | CH$_3$ | |
| 186 | 5-OCF$_3$ | 4-Cl—Ph | H | CH$_3$ | C$_2$H$_5$ | CH$_3$ | |
| 187 | 5-OCF$_3$ | 4-Cl—Ph | H | CH$_3$ | C$_2$H$_5$ | C$_2$H$_5$ | |
| 188 | 5-OCF$_3$ | 4-Cl—Ph | H | CH$_3$ | t-C$_4$H$_9$ | H | |
| 189 | 5-OCF$_3$ | 4-F—Ph | H | CH$_3$ | CH$_3$ | CH$_3$ | |
| 190 | 5-OCF$_3$ | 4-F—Ph | H | CH$_3$ | C$_2$H$_5$ | CH$_3$ | |
| 191 | 5-OCF$_3$ | 4-F—Ph | H | CH$_3$ | t-C$_4$H$_9$ | H | |
| 192 | 5-OCF$_3$ | 4-Br—Ph | H | CH$_3$ | CH$_3$ | CH$_3$ | |
| 193 | 5-OCF$_3$ | 4-Br—Ph | H | CH$_3$ | t-C$_4$H$_9$ | H | |
| 194 | 5-OCF$_3$ | 4-CH$_3$—Ph | H | CH$_3$ | CH$_3$ | CH$_3$ | |
| 195 | 5-OCF$_3$ | 4-CF$_3$—Ph | H | CH$_3$ | CH$_3$ | CH$_3$ | |
| 196 | 5-OCF$_3$ | 4-CF$_3$—Ph | H | CH$_3$ | C$_2$H$_5$ | CH$_3$ | |
| 197 | 5-OCF$_3$ | 4-CF$_2$—Ph | H | CH$_3$ | C$_2$H$_5$ | C$_2$H$_5$ | |
| 198 | 5-OCF$_3$ | 4-C$_3$—Ph | H | CH$_3$ | t-C$_4$H$_9$ | H | |
| 199 | 5-OCF$_3$ | 4-OCF$_3$—Ph | H | CH$_3$ | CH$_3$ | CH$_3$ | |
| 200 | 5-OCF$_3$ | 4-OCF$_3$—Ph | H | CH$_3$ | C$_2$H$_5$ | CH$_3$ | |
| 201 | 5-OCF$_3$ | 4-OCF$_3$—Ph | H | CH$_3$ | t-C$_4$H$_9$ | H | |
| 202 | 5-OCF$_3$ | 4-OCF$_2$H—Ph | H | CH$_3$ | CH$_3$ | CH$_3$ | |
| 203 | 5-OCF$_3$ | 4-OCF$_2$H—Ph | H | CH$_3$ | C$_2$H$_5$ | CH$_3$ | |
| 204 | 5-OCF$_3$ | 4-OCF$_2$H—Ph | H | CH$_3$ | t-C$_4$H$_9$ | H | |
| 205 | 5-OCF$_2$ | 4-OCF$_2$CF$_2$H—Ph | H | CH$_3$ | CH$_3$ | CH$_3$ | |
| 206 | 5-OCF$_3$ | 4-OCH$_2$CF$_3$H—Ph | H | CH$_3$ | CH$_3$ | CH$_3$ | |
| 207 | 5-OCF$_3$ | 4-OCH$_3$—Ph | H | CH$_3$ | CH$_3$ | CH$_3$ | |
| 208 | 5-OCF$_3$ | 4-SCH$_3$—Ph | H | CH$_3$ | CH$_3$ | CH$_3$ | |
| 209 | 5-OCF$_3$ | 4-NO$_2$—Ph | H | CH$_3$ | CH$_3$ | CH$_3$ | |
| 210 | 5-OCF$_3$ | 4-CN—Ph | H | CH$_3$ | CH$_3$ | CH$_3$ | |
| 211 | 5-OCF$_2$H | Ph | H | CH$_3$ | CH$_3$ | CH$_3$ | |
| 212 | 5-OCF$_2$H | Ph | H | CH$_3$ | C$_2$H$_5$ | CH$_3$ | |

TABLE 1-continued (A=CH$_2$)

| Compound No. | R$^1$ | R$^2$ | R$^3$ | R$^4$ | R$^5$ | R$^6$ | Physical properties |
|---|---|---|---|---|---|---|---|
| 213 | 5-OCF$_2$H | Ph | H | CH$_3$ | C$_2$H$_5$ | C$_2$H$_5$ | |
| 214 | 5-OCF$_2$H | Ph | H | CH$_3$ | t-C$_4$H$_9$ | H | |
| 215 | 5-OCF$_2$H | 4-Cl—Ph | H | CH$_3$ | CH$_3$ | CH$_3$ | |
| 216 | 5-OCF$_2$H | 4-Cl—Ph | H | CH$_3$ | C$_2$H$_5$ | CH$_3$ | |
| 217 | 5-OCF$_2$H | 4-Cl—Ph | H | CH$_3$ | C$_2$H$_5$ | C$_2$H$_5$ | |
| 218 | 5-OCF$_2$H | 4-Cl—Ph | H | CH$_3$ | i-C$_3$H$_7$ | H | |
| 219 | 5-OCF$_2$H | 4-Cl—Ph | H | CH$_3$ | t-C$_4$H$_9$ | H | |
| 220 | 5-OCF$_2$H | 4-F—Ph | H | CH$_3$ | CH$_3$ | CH$_3$ | |
| 221 | 5-OCF$_2$H | 4-F—Ph | H | CH$_3$ | C$_2$H$_5$ | CH$_3$ | |
| 222 | 5-OCF$_2$H | 4-F—Ph | H | CH$_3$ | C$_2$H$_5$ | C$_2$H$_5$ | |
| 223 | 5-OCF$_2$H | 4-F—Ph | H | CH$_3$ | i-C$_3$H$_7$ | H | |
| 224 | 5-OCF$_2$H | 4-F—Ph | H | CH$_3$ | t-C$_4$H$_9$ | H | |
| 225 | 5-OCF$_2$H | 4-Br—Ph | H | CH$_3$ | CH$_3$ | CH$_3$ | |
| 226 | 5-OCF$_2$H | 4-Br—Ph | H | CH$_3$ | t-C$_4$H$_9$ | H | |
| 227 | 5-OCF$_2$H | 4-CH$_3$—Ph | H | CH$_3$ | CH$_3$ | CH$_3$ | |
| 228 | 5-OCF$_2$H | 4-CF$_3$—Ph | H | CH$_3$ | CH$_3$ | CH$_3$ | |
| 229 | 5-OCF$_2$H | 4-CF$_3$—Ph | H | CH$_3$ | C$_2$H$_5$ | CH$_3$ | |
| 230 | 5-OCF$_2$H | 4-CF$_3$—Ph | H | CH$_3$ | C$_2$H$_5$ | C$_2$H$_5$ | |
| 231 | 5-OCF$_2$H | 4-CF$_3$—Ph | H | CH$_3$ | i-C$_3$H$_7$ | H | |
| 232 | 5-OCF$_2$H | 4-CF$_3$—Ph | H | CH$_3$ | t-C$_4$H$_9$ | H | |
| 233 | 5-OCF$_2$H | 4-OCF$_2$—Ph | H | CH$_3$ | CH$_3$ | CH$_3$ | |
| 234 | 5-OCF$_2$H | 4-OCF$_2$—Ph | H | CH$_3$ | t-C$_4$H$_9$ | H | |
| 235 | 5-OCF$_2$H | 4-OCF$_2$H—Ph | H | CH$_3$ | CH$_3$ | CH$_3$ | |
| 236 | 5-OCF$_2$H | 4-OCF$_2$H—Ph | H | CH$_3$ | CH$_3$ | CH$_3$ | |
| 237 | 5-OCF$_2$H | 4-OCF$_2$H—Ph | H | CH$_3$ | t-C$_4$H$_9$ | H | |
| 238 | 5-OCF$_2$H | 4-OCF$_2$CF$_2$H—Ph | H | CH$_3$ | CH$_3$ | CH$_3$ | |
| 239 | 5-OCF$_2$H | 4-OCH$_2$CF$_2$H—Ph | H | CH$_3$ | CH$_3$ | CH$_3$ | |
| 240 | 5-OCF$_2$H | 4-OCH$_3$—Ph | H | CH$_3$ | CH$_3$ | CH$_3$ | |
| 241 | 5-OCF$_2$H | 4-SCH$_3$—Ph | H | CH$_3$ | CH$_3$ | CH$_3$ | |
| 242 | 5-OCF$_2$H | 4-CN—Ph | H | CH$_3$ | CH$_3$ | CH$_3$ | |
| 243 | 5-OCF$_2$H | 4-NO$_2$—Ph | H | CH$_3$ | CH$_3$ | CH$_3$ | |
| 244 | 5-OCF$_2$CF$_2$H | Ph | H | CH$_3$ | CH$_3$ | CH$_3$ | |
| 245 | 5-OCF$_2$CF$_2$H | 4-Cl—Ph | H | CH$_3$ | CH$_3$ | CH$_3$ | |
| 246 | 5-OCF$_2$CF$_2$H | 4-F—Ph | H | CH$_3$ | CH$_3$ | CH$_3$ | |
| 247 | 5-OCF$_2$CF$_2$H | 4-CF$_3$—Ph | H | CH$_3$ | CH$_3$ | CH$_3$ | |
| 248 | 5-OCF$_2$CF$_2$H | 4-OCF$_3$—Ph | H | CH$_3$ | CH$_3$ | CH$_3$ | |
| 249 | 5-OCF$_2$CF$_2$H | 4-OCF$_2$H—Ph | n | CH$_3$ | CH$_3$ | CH$_3$ | |
| 250 | 5-OCH$_2$CF$_3$ | Ph | H | CH$_3$ | CH$_3$ | CH$_3$ | |
| 251 | 5-OCH$_2$CF$_3$ | 4-Cl—Ph | H | CH$_3$ | CH$_3$ | CH$_3$ | |
| 252 | 5-OCH$_2$CF$_3$ | 4-F—Ph | H | CH$_3$ | CH$_3$ | CH$_3$ | |
| 253 | 5-OCH$_2$CF$_3$ | 4-CF$_3$—Ph | H | CH$_3$ | CH$_3$ | CH$_3$ | |
| 254 | 5-OCH$_2$CF$_3$ | 4-OCF$_3$—Ph | H | CH$_3$ | CH$_3$ | CH$_3$ | |
| 255 | 5-OCH$_2$CF$_3$ | 4-OCF$_2$H—Ph | H | CH$_3$ | CH$_3$ | CH$_3$ | |
| 256 | 5-NO$_2$ | Ph | H | CH$_3$ | CH$_3$ | CH$_3$ | |
| 257 | 5-NO$_2$ | 4-Cl—Ph | H | CH$_3$ | CH$_3$ | CH$_3$ | |
| 258 | 5-NO$_2$ | 4-F—Ph | H | CH$_3$ | CH$_3$ | CH$_3$ | |
| 259 | 5-CN | Ph | H | CH$_3$ | CH$_3$ | CH$_3$ | |
| 260 | 5-CN | 4-Cl—Ph | H | CH$_3$ | CH$_3$ | CH$_3$ | |
| 261 | 5-CN | 4-F—Ph | H | CH$_3$ | CH$_3$ | CH$_3$ | |
| 262 | 5-CH$_3$ | Ph | H | CH$_3$ | CH$_3$ | CH$_3$ | |
| 263 | 5-CH$_3$ | 4-Cl—Ph | H | CH$_3$ | CH$_3$ | CH$_3$ | $n_D^{24.5}$ 1.6237 |
| 264 | 5-CH$_3$ | 4-F—Ph | H | CH$_3$ | CH$_3$ | CH$_3$ | |
| 265 | H | 4-Cl—Ph | H | CH$_3$ | CH$_3$ | CH$_3$ | m.p., 132.4° C. |
| 266 | H | 4-F—Ph | H | CH$_3$ | CH$_3$ | CH$_3$ | |
| 267 | H | 4-CF$_3$—Ph | H | CH$_3$ | CH$_3$ | CH$_3$ | |
| 268 | H | 4-OCF$_2$H—Ph | H | CH$_3$ | CH$_3$ | CH$_3$ | |
| 269 | 5-Cl | Ph | CH$_3$ | CH$_3$ | CH$_3$ | CH$_3$ | |
| 270a | 5-Cl | 4-Cl—Ph | CH$_3$ | CH$_3$ | CH$_3$ | CH$_3$ | m.p., 134.8° C. |
| 270b | 5-Cl | 4-Cl—Ph | CH$_3$ | CH$_3$ | CH$_3$ | CH$_3$ | m.p., 110.9° C. |
| 271a | 5-Cl | 4-F—Ph | CH$_3$ | CH$_3$ | CH$_3$ | CH$_3$ | m.p., 118.4° C. |
| 271b | 5-Cl | 4-F—Ph | CH$_3$ | CH$_3$ | CH$_3$ | CH$_3$ | $n_D^{23.0}$ 1.6213 |
| 272 | 5-Cl | 4-Br—Ph | CH$_3$ | CH$_3$ | CH$_3$ | CH$_3$ | |
| 273 | 5-Cl | 4-CF$_3$—Ph | CH$_3$ | CH$_3$ | CH$_3$ | CH$_3$ | |
| 274 | 5-Cl | 4-OCF$_3$—Ph | CH$_3$ | CH$_3$ | CH$_3$ | CH$_3$ | |
| 275 | 5-Cl | 4-OCF$_2$H—Ph | CH$_3$ | CH$_3$ | CH$_3$ | CH$_3$ | |
| 276 | 5-Cl | 4-NO$_2$—Ph | CH$_3$ | CH$_3$ | CH$_3$ | CH$_3$ | |
| 277 | 5-Cl | 4-CH$_3$—Ph | CH$_3$ | CH$_3$ | CH$_3$ | CH$_3$ | |
| 278 | 5-Cl | 4-CN—Ph | CH$_3$ | CH$_3$ | CH$_3$ | CH$_3$ | |
| 279 | 5-F | Ph | CH$_3$ | CH$_3$ | CH$_3$ | CH$_3$ | |
| 280 | 5-F | 4-Cl—Ph | CH$_3$ | CH$_3$ | CH$_3$ | CH$_3$ | |
| 281 | 5-F | 4-F—Ph | CH$_3$ | CH$_3$ | CH$_3$ | CH$_3$ | |
| 282 | 5-F | 4-CF$_3$—Ph | CH$_3$ | CH$_3$ | CH$_3$ | CH$_3$ | |
| 283 | 5-F | 4-OCF$_3$—Ph | CH$_3$ | CH$_3$ | CH$_3$ | CH$_3$ | |
| 284 | 5-F | 4-OCF$_2$H—Ph | CH$_3$ | CH$_3$ | CH$_3$ | CH$_3$ | |
| 285 | 5-CF$_3$ | Ph | CH$_3$ | CH$_3$ | CH$_3$ | CH$_3$ | |
| 286 | 5-CF$_3$ | 4-Cl—Ph | CH$_3$ | CH$_3$ | CH$_3$ | CH$_3$ | |
| 287 | 5-CF$_3$ | 4-F—Ph | CH$_3$ | CH$_3$ | CH$_3$ | CH$_3$ | |
| 288 | 5-CF | 4-OCF$_3$—Ph | CH$_3$ | CH$_3$ | CH$_3$ | CH$_3$ | |
| 289 | 5-CF$_3$ | 4-OCF$_2$H—Ph | CH$_3$ | CH$_3$ | CH$_3$ | CH$_3$ | |

TABLE 1-continued (A=CH$_2$)

| Compound No. | R$^1$ | R$^2$ | R$^3$ | R$^4$ | R$^5$ | R$^6$ | Physical properties |
|---|---|---|---|---|---|---|---|
| 290 | 5-OCF$_3$ | Ph | CH$_3$ | CH$_3$ | CH$_3$ | CH$_3$ | |
| 291 | 5-OCF$_3$ | 4-Cl—Ph | CH$_3$ | CH$_3$ | CH$_3$ | CH$_3$ | |
| 292 | 5-OCF$_3$ | 4-F—Ph | CH$_3$ | CH$_3$ | CH$_3$ | CH$_3$ | |
| 293 | 5-OCF$_3$ | 4-CF$_3$—Ph | CH$_3$ | CH$_3$ | CH$_3$ | CH$_3$ | |
| 294 | 5-OCF$_3$ | 4-OCF$_3$—Ph | CH$_3$ | CH$_3$ | CH$_3$ | CH$_3$ | |
| 295 | 5-OCF$_3$ | 4-OCF$_2$H—Ph | CH$_3$ | CH$_3$ | CH$_3$ | CH$_3$ | |
| 296 | 5-OCF$_3$H | Ph | CH$_3$ | CH$_3$ | CH$_3$ | CH$_3$ | |
| 297 | 5-OCH$_2$H | 4-Cl—Ph | CH$_3$ | CH$_3$ | CH$_3$ | CH$_3$ | |
| 298 | 5-OCF$_2$H | 4-F—Ph | CH$_3$ | CH$_3$ | CH$_3$ | CH$_3$ | |
| 299 | 5-OCF$_2$H | 4-CF$_3$—Ph | CH$_3$ | CH$_3$ | CH$_3$ | CH$_3$ | |
| 300 | 5-OCF$_2$H | 4-OCF$_3$—Ph | CH$_3$ | CH$_3$ | CH$_3$ | CH$_3$ | |
| 301 | 5-OCF$_2$H | 4-OCF$_2$H—Ph | CH$_3$ | CH$_3$ | CH$_3$ | CH$_3$ | |
| 302 | 5-OCH$_2$CF$_2$H | 4-Cl—Ph | CH$_3$ | CH$_3$ | CH$_3$ | CH$_3$ | |
| 303 | 5-OCH$_2$CF$_2$H | 4-F—Ph | CH$_3$ | CH$_3$ | CH$_3$ | CH$_3$ | |
| 304 | 5-OCH$_2$CF$_2$H | 4-Cl—Ph | CH$_3$ | CH$_3$ | CH$_3$ | CH$_3$ | |
| 305 | 5-OCH$_2$CF$_2$H | 4-F—Ph | CH$_3$ | CH$_3$ | CH$_3$ | CH$_3$ | |
| 306 | 5-OCH$_3$ | 4-Cl—Ph | CH$_3$ | CH$_3$ | CH$_3$ | CH$_3$ | |
| 307 | 5-OCH$_3$ | 4-F—Ph | CH$_3$ | CH$_3$ | CH$_3$ | CH$_3$ | |
| 308 | 5-SCH$_3$ | 4-Cl—Ph | CH$_3$ | CH$_3$ | CH$_3$ | CH$_3$ | |
| 309 | 5-SCH$_3$ | 4-F—Ph | CH$_3$ | CH$_3$ | CH$_3$ | CH$_3$ | |
| 310 | 5-NO$_2$ | 4-Cl—Ph | CH$_3$ | CH$_3$ | CH$_3$ | CH$_3$ | |
| 311 | 5-NO$_2$ | 4-F—Ph | CH$_3$ | CH$_3$ | CH$_3$ | CH$_3$ | |
| 312 | 5-CN | 4-Cl—Ph | CH$_3$ | CH$_3$ | CH$_3$ | CH$_3$ | |
| 313 | 5-CN | 4-F—Ph | CH$_3$ | CH$_3$ | CH$_3$ | CH$_3$ | |
| 314 | 5-Cl | Ph | H | H | CH$_3$ | CH$_3$ | |
| 315 | 5-Cl | Ph | H | C$_2$H$_5$ | CH$_3$ | CH$_3$ | |
| 316 | 5-Cl | Ph | H | i-C$_3$H$_7$ | CH$_3$ | CH$_3$ | |
| 317 | 5-Cl | Ph | H | CF$_3$ | CH$_3$ | CH$_3$ | |
| 318 | 5-Cl | 4-Cl—Ph | H | H | CH$_3$ | CH$_3$ | m.p., 123.2° C. |
| 319 | 5-Cl | 4-Cl—Ph | H | H | C$_2$H$_5$ | CH$_3$ | |
| 320 | 5-Cl | 4-Cl—Ph | H | H | C$_2$H$_5$ | C$_2$H$_5$ | |
| 321 | 5-Cl | 4-Cl—Ph | H | H | t-C$_4$H$_9$ | H | |
| 322 | 5-Cl | 4-Cl—Ph | H | C$_2$H$_5$ | CH$_3$ | CH$_3$ | m.p., 100.7° C. |
| 323 | 5-Cl | 4-Cl—Ph | H | C$_2$H$_5$ | C$_2$H$_5$ | CH$_3$ | |
| 324 | 5-Cl | 4-Cl—Ph | H | C$_2$H$_5$ | C$_2$H$_5$ | C$_2$H$_5$ | |
| 325 | 5-Cl | 4-Cl—Ph | H | C$_2$H$_5$ | t-C$_4$H$_9$ | H | |
| 326 | 5-Cl | 4-Cl—Ph | H | n-C$_3$H$_7$ | CH$_3$ | CH$_3$ | n$_D^{22.0}$ 1.4705 |
| 327 | 5-Cl | 4-Cl—Ph | H | n-C$_3$H$_7$ | C$_2$H$_5$ | CH$_3$ | |
| 328 | 5-Cl | 4-Cl—Ph | H | n-C$_3$H$_7$ | C$_2$H$_5$ | C$_2$H$_5$ | |
| 329 | 5-Cl | 4-Cl—Ph | H | n-C$_3$H$_7$ | t-C$_4$H$_9$ | H | |
| 330 | 5-Cl | 4-Cl—Ph | H | i-C$_3$H$_7$ | CH$_3$ | CH$_3$ | n$_D^{22.5}$ 1.6133 |
| 331 | 5-Cl | 4-Cl—Ph | H | i-C$_3$H$_7$ | C$_2$H$_5$ | CH$_3$ | |
| 332 | 5-Cl | 4-Cl—Ph | H | i-C$_3$H$_7$ | C$_2$H$_5$ | C$_2$H$_5$ | |
| 333 | 5-Cl | 4-Cl—Ph | H | i-C$_3$H$_7$ | t-C$_4$H$_9$ | H | |
| 334 | 5-Cl | 4-Cl—Ph | H | t-C$_4$H$_9$ | CH$_3$ | CH$_3$ | n$_D^{23.0}$ 1.6155 |
| 335 | 5-Cl | 4-Cl—Ph | H | t-C$_4$H$_9$ | C$_2$H$_5$ | CH$_3$ | |
| 336 | 5-Cl | 4-Cl—Ph | H | t-C$_4$H$_9$ | C$_2$H$_5$ | C$_2$H$_5$ | |
| 337 | 5-Cl | 4-Cl—Ph | H | t-C$_4$H$_9$ | t-C$_4$H$_9$ | H | |
| 338 | 5-Cl | 4-Cl—Ph | H | t-C$_4$H$_9$ | CH$_2$CF$_3$ | H | |
| 339 | 5-Cl | 4-Cl—Ph | H | n-C$_5$H$_{11}$ | CH$_3$ | CH$_3$ | |
| 340 | 5-Cl | 4-Cl—Ph | H | CF$_3$ | CH$_3$ | CH$_3$ | n$_D^{23.0}$ 1.5958 |
| 341 | 5-Cl | 4-Cl—Ph | H | CF$_3$ | C$_2$H$_5$ | CH$_3$ | |
| 342 | 5-Cl | 4-Cl—Ph | H | CF$_3$ | C$_2$H$_5$ | C$_2$H$_5$ | |
| 343 | 5-Cl | 4-Cl—Ph | H | CF$_3$ | t-C$_4$H$_9$ | H | |
| 344 | 5-Cl | 4-Cl—Ph | H | CF$_2$CF$_3$ | CH$_3$ | CH$_3$ | |
| 345 | 5-Cl | 4-Cl—Ph | H | CH$_2$CH$_2$CF$_2$CF$_3$ | CH$_3$ | CH$_3$ | |
| 346 | 5-Cl | 4-F—Ph | H | H | CH$_3$ | CH$_3$ | m.p., 134.4° C. |
| 347 | 5-Cl | 4-F—Ph | H | C$_2$H$_5$ | CH$_3$ | CH$_3$ | n$_D^{23.3}$ 1.5820 |
| 348 | 5-Cl | 4-F—Ph | H | i-C$_3$H$_7$ | CH$_3$ | CH$_3$ | n$_D^{20.0}$ 1.6208 |
| 349 | 5-Cl | 4-F—Ph | H | t-C$_4$H$_9$ | CH$_3$ | CH$_3$ | |
| 350 | 5-Cl | 4-F—Ph | H | CF$_3$ | CH$_3$ | CH$_3$ | |
| 351 | 5-Cl | 4-CF$_3$—Ph | H | H | CH$_3$ | CH$_3$ | |
| 352 | 5-Cl | 4-CF$_3$—Ph | H | C$_2$H$_5$ | CH$_3$ | CH$_3$ | |
| 353 | 5-Cl | 4-CF$_3$—Ph | H | i-C$_3$H$_7$ | CH$_3$ | CH$_3$ | |
| 354 | 5-Cl | 4-CF$_3$—Ph | H | t-C$_4$H$_9$ | CH$_3$ | CH$_3$ | |
| 355 | 5-Cl | 4-CF$_3$—Ph | H | CF$_3$ | CH$_3$ | CH$_3$ | |
| 356 | 5-Cl | 4-OCF$_3$—Ph | H | H | CH$_3$ | CH$_3$ | |
| 357 | 5-Cl | 4-OCF$_3$—Ph | H | C$_2$H$_5$ | CH$_3$ | CH$_3$ | |
| 358 | 5-Cl | 4-OCF$_3$—Ph | H | i-C$_3$H$_7$ | CH$_3$ | CH$_3$ | |
| 359 | 5-Cl | 4-OCF$_3$—Ph | H | CF$_3$ | CH$_3$ | CH$_3$ | |
| 360 | 5-Cl | 4-OCF$_2$H—Ph | H | H | CH$_3$ | CH$_3$ | |
| 361 | 5-Cl | 4-OCF$_2$H—Ph | H | C$_2$H$_5$ | CH$_3$ | CH$_3$ | |
| 362 | 5-Cl | 4-OCF$_2$H—Ph | H | i-C$_3$H$_7$ | CH$_3$ | CH$_3$ | |
| 363 | 5-Cl | 4-OCF$_2$H—Ph | H | CF$_3$ | CH$_3$ | CH$_3$ | |
| 364 | 5-F | Ph | H | H | CH$_3$ | CH$_3$ | |
| 365 | 5-F | Ph | H | C$_2$H$_5$ | CH$_3$ | CH$_3$ | |
| 366 | 5-F | Ph | H | i-C$_3$H$_7$ | CH$_3$ | CH$_3$ | |
| 367 | 5-F | Ph | H | CF$_3$ | CH$_3$ | CH$_3$ | |

TABLE 1-continued (A=CH$_2$)

| Compound No. | R$^1$ | R$^2$ | R$^3$ | R$^4$ | R$^5$ | R$^6$ | Physical properties |
|---|---|---|---|---|---|---|---|
| 368 | 5-F | 4-Cl—Ph | H | H | CH$_3$ | CH$_3$ | |
| 369 | 5-F | 4-Cl—Ph | H | C$_2$H$_5$ | CH$_3$ | CH$_3$ | |
| 370 | 5-F | 4-Cl—Ph | H | i-C$_3$H$_7$ | CH$_3$ | CH$_3$ | |
| 371 | 5-F | 4-Cl—Ph | H | CF$_3$ | CH$_3$ | CH$_3$ | |
| 372 | 5-F | 4-F—Ph | H | H | CH$_3$ | CH$_3$ | m.p., 88.2° C. |
| 373 | 5-F | 4-F—Ph | H | C$_2$H$_5$ | CH$_3$ | CH$_3$ | |
| 374 | 5-F | 4-F—Ph | H | i-C$_3$H$_7$ | CH$_3$ | CH$_3$ | |
| 375 | 5-F | 4-F—Ph | H | CF$_3$ | CH$_3$ | CH$_3$ | |
| 376 | 5-F | 4-CF$_3$Ph | H | H | CH$_3$ | CH$_3$ | |
| 377 | 5-F | 4-CF$_3$Ph | H | C$_2$H$_5$ | CH$_3$ | CH$_3$ | |
| 378 | 5-F | 4-CF$_3$Ph | H | i-C$_3$H$_7$ | CH$_3$ | CH$_3$ | |
| 379 | 5-F | 4-CF$_3$Ph | H | CF$_3$ | CH$_3$ | CH$_3$ | |
| 380 | 5-F | 4-OCF$_3$—Ph | H | H | CH$_3$ | CH$_3$ | |
| 381 | 5-F | 4-OCF$_3$—Ph | H | C$_2$H$_5$ | CH$_3$ | CH$_3$ | |
| 382 | 5-F | 4-OCF$_3$—Ph | H | i-C$_3$H$_7$ | CH$_3$ | CH$_3$ | |
| 383 | 5-F | 4-OCF$_3$—Ph | H | CF$_3$ | CH$_{33}$ | CH$_3$ | |
| 384 | 5-F | 4-OCF$_2$H—Ph | H | H | CH$_3$ | CH$_3$ | |
| 385 | 5-F | 4-OCF$_2$H—Ph | H | C$_2$H$_5$ | CH$_3$ | CH$_3$ | |
| 386 | 5-F | 4-OCF$_2$H—Ph | H | i-C$_3$H$_7$ | CH$_3$ | CH$_3$ | |
| 387 | 5-OCF$_3$ | Ph | H | H | CH$_3$ | CH$_3$ | |
| 388 | 5-OCF$_3$ | Ph | H | C$_2$H$_5$ | CH$_3$ | CH$_3$ | |
| 389 | 5-OCF$_3$ | Ph | H | i-C$_3$H$_7$ | CH$_3$ | CH$_3$ | |
| 390 | 5-OCF$_3$ | Ph | H | CF$_3$ | CH$_3$ | CH$_3$ | |
| 391 | 5-OCF$_3$ | 4-Cl—Ph | H | H | CH$_3$ | CH$_3$ | |
| 392 | 5-OCF$_3$ | 4-Cl—Ph | H | C$_2$H$_5$ | CH$_3$ | CH$_3$ | |
| 393 | 5-OCF$_3$ | 4-Cl—Ph | H | i-C$_3$H$_7$ | CH$_3$ | CH$_3$ | |
| 394 | 5-OCF$_3$ | 4-Cl—Ph | H | CF$_3$ | CH$_3$ | CH$_3$ | |
| 395 | 5-OCF$_3$ | 4-F—Ph | H | H | CH$_3$ | CH$_3$ | |
| 396 | 5-OCF$_3$ | 4-F—Ph | H | C$_2$H$_5$ | CH$_3$ | CH$_3$ | |
| 397 | 5-OCF$_3$ | 4-F—Ph | H | i-C$_3$H$_7$ | CH$_3$ | CH$_3$ | |
| 398 | 5-OCF$_3$ | 4-F—Ph | H | CF$_3$ | CH$_3$ | CH$_3$ | |
| 399 | 5-OCF$_2$H | Ph | H | H | CH$_3$ | CH$_3$ | |
| 400 | 5-OCF$_2$H | Ph | H | C$_2$H$_5$ | CH$_3$ | CH$_3$ | |
| 401 | 5-OCF$_2$H | Ph | H | i-C$_3$H$_7$ | CH$_3$ | CH$_3$ | |
| 402 | 5-OCF$_2$H | Ph | H | CF$_3$ | CH$_3$ | CH$_3$ | |
| 403 | 5-OCF$_2$H | 4-Cl—Ph | H | H | CH$_3$ | CH$_3$ | |
| 404 | 5-OCF$_2$H | 4-Cl—Ph | H | C$_2$H$_5$ | CH$_3$ | CH$_3$ | |
| 405 | 5-OCF$_2$H | 4-Cl—Ph | H | i-C$_3$H$_7$ | CH$_3$ | CH$_3$ | |
| 406 | 5-OCF$_2$H | 4-Cl—Ph | H | CF$_3$ | CH$_3$ | CH$_3$ | |
| 407 | 5-OCF$_2$H | 4-F—Ph | H | H | CH$_3$ | CH$_3$ | |
| 408 | 5-OCF$_2$H | 4-F—Ph | H | C$_2$H$_5$ | CH$_3$ | CH$_3$ | |
| 409 | 5-OCF$_2$H | 4-F—Ph | H | i-C$_3$H$_7$ | CH$_3$ | CH$_3$ | |
| 410 | 5-OCF$_2$H | 4-F—Ph | H | CF$_3$ | CH$_3$ | CH$_3$ | |
| 411 | 5-OCF$_2$H | 4-CF$_3$—Ph | H | H | CH$_3$ | CH$_3$ | |
| 412 | 5-OCH$_2$H | 4-CF$_3$—Ph | H | C$_2$H$_5$ | CH$_3$ | CH$_3$ | |
| 413 | 5-OCF$_2$H | 4-CF$_3$—Ph | H | i-C$_3$H$_7$ | CH$_3$ | CH$_3$ | |
| 414 | 5-OCF$_2$H | 4-CF$_2$—Ph | H | CF$_3$ | CH$_3$ | CH$_3$ | |
| 415 | 5-OCF$_2$H | 4-OCF$_3$—Ph | H | H | CH$_3$ | CH$_3$ | |
| 416 | 5-OCF$_2$H | 4-OCF$_3$—Ph | H | C$_2$H$_5$ | CH$_3$ | CH$_3$ | |
| 417 | 5-OCF$_2$H | 4-OCF$_3$—Ph | H | i-C$_3$H$_7$ | CH$_3$ | CH$_3$ | |
| 418 | 5-OCF$_2$H | 4-OCF$_2$—Ph | H | CF$_3$ | CH$_3$ | CH$_3$ | |
| 419 | 5-OCF$_2$H | 4-OCF$_2$H—Ph | H | H | CH$_3$ | CH$_3$ | |
| 420 | 5-OCF$_2$H | 4-OCF$_2$H—Ph | H | C$_2$H$_5$ | CH$_3$ | CH$_3$ | |
| 421 | 5-OCF$_2$H | 4-OCF$_2$H—Ph | H | i-C$_3$H$_7$ | CH$_3$ | CH$_3$ | |
| 422 | 5-OCF$_2$H | 4-OCF$_2$H—Ph | H | CF$_3$ | CH$_3$ | CH$_3$ | |
| 423 | 5-Cl | 4-Cl—Ph | H | CH$_3$ | CH$_2$OCH$_3$ | CH$_3$ | |
| 424 | 5-Cl | 4-Cl—Ph | H | CH$_3$ | CH$_2$CH$_2$OCH$_3$ | CH$_3$ | |
| 425 | 5-Cl | 4-Cl—Ph | H | CH$_3$ | CH$_2$CH$_2$OCF$_2$H | CH$_3$ | |
| 426 | 5-Cl | 4-Cl—Ph | H | CH$_3$ | CH$_2$CH$_2$OCF$_2$CF$_2$H | CH$_3$ | |
| 427 | 5-Cl | 4-Cl—Ph | H | CH$_3$ | CH$_2$CH$_2$OCH$_2$CF$_2$CF$_3$ | CH$_3$ | |
| 428 | 5-Cl | 4-Cl—Ph | H | CH$_3$ | CH$_2$CH$_2$SCH$_3$ | CH$_3$ | |
| 429 | 5-Cl | 4-Cl—Ph | H | CH$_3$ | CH$_2$CH$_2$O(CH$_2$)$_3$CH$_3$ | CH$_3$ | |
| 430 | 5-Cl | 4-Cl—Ph | H | CH$_3$ | CH$_2$CH$_2$SCH$_3$CH$_3$ | CH$_3$ | |
| 431 | 5-Cl | 4-Cl—Ph | H | CH$_3$ | CH$_2$CH$_2$SCF$_2$H | CH$_3$ | |
| 432 | 5-Cl | 4-Cl—Ph | H | CH$_3$ | CH$_2$CH$_2$SCH$_2$CF$_3$ | CH$_3$ | |
| 433 | 5-Cl | 4-Cl—Ph | H | CH$_3$ | CH$_2$CH$_2$N(CH$_3$)$_2$ | CH$_3$ | |
| 434 | 5-Cl | 4-Cl—Ph | H | CH$_3$ | CH$_2$CH$_2$N(CH$_2$CH$_3$)2 | CH$_3$ | |
| 435 | 5-Cl | 4-Cl—Ph | H | CH$_3$ | CH$_2$CH$_2$NHCH$_2$CH$_3$ | CH$_3$ | |
| 436 | 5-Cl | 4-Cl—Ph | H | CH$_3$ | CH$_2$CH$_2$OCH$_2$CH$_2$ | | m.p., 126.7° C. |
| 437 | 5-Cl | 4-Cl—Ph | H | CH$_3$ | CH$_2$CH$_2$SCH$_2$CH$_2$ | | viscous liquid |
| 438 | 5-Cl | 4-Cl—Ph | H | CH$_3$ | CH$_2$(CH$_2$)$_2$CH$_2$ | | m.p., 134.8° C. |
| 439 | 5-Cl | 4-Cl—Ph | H | CH$_3$ | CH$_2$(CH$_2$) CH$_2$ | | m.p., 122,3° C. |
| 440 | 5-Cl | 4-Cl—Ph | H | CH$_3$ | CH$_2$CH(CH$_3$)OCH$_2$CH$_2$ | | |
| 441 | 5-Cl | 3-Cl—Ph | H | CH$_3$ | CH$_3$ | CH$_3$ | m.p., 136.7° C. |
| 442 | 5-Cl | 3-F—Ph | H | CH$_3$ | CH$_3$ | CH$_3$ | |
| 443 | 5-Cl | 3-Br—Ph | H | CH$_3$ | CH$_3$ | CH$_3$ | |
| 444 | 5-Cl | 3-CF$_3$—Ph | H | CH$_3$ | CH$_3$ | CH$_3$ | |
| 445 | 5-Cl | 3-OCF$_2$H—Ph | H | CH$_3$ | CH$_3$ | CH$_3$ | |
| 446 | 5-Cl | 3-NO$_2$—Ph | H | CH$_3$ | CH$_3$ | CH$_3$ | |

TABLE 1-continued (A=CH$_2$)

| Compound No. | R$^1$ | R$^2$ | R$^3$ | R$^4$ | R$^5$ | R$^6$ | Physical properties |
|---|---|---|---|---|---|---|---|
| 447 | 5-Cl | 2,4-Cl$_2$—Ph | H | CH$_3$ | CH$_3$ | CH$_3$ | m.p., 138.2° C. |
| 448 | 5-Cl | 2,4-F$_2$—Ph | H | CH$_3$ | CH$_3$ | CH$_3$ | m.p., 153.3° C. |
| 449 | 5-Cl | 3,4-Cl$_2$—Ph | H | CH$_3$ | CH$_3$ | CH$_3$ | m.p., 123,8° C. |
| 450 | 4-Cl | 4-Cl—Ph | H | CH$_3$ | CH$_3$ | CH$_3$ | n$_D^{23.2}$ 1.6529 |
| 451 | 4-Cl | 4-F—Ph | H | CH$_3$ | CH$_3$ | CH$_3$ | n$_D^{23.2}$ 1.6522 |
| 452 | 6-Cl | 4-Cl—Ph | H | CH$_3$ | CH$_3$ | CH$_3$ | |
| 453 | 6-Cl | 4-F—Ph | H | CH$_3$ | CH$_3$ | CH$_3$ | |
| 454 | 4,6-Cl$_2$ | 4-F—Ph | H | CH$_3$ | CH$_3$ | CH$_3$ | |
| 455 | 5-F | 2-Cl—Ph | H | CH$_3$ | CH$_3$ | CH$_3$ | |
| 456 | 5-F | 2-F—Ph | H | CH$_3$ | CH$_3$ | CH$_3$ | |
| 457 | 5-F | 2-Br—Ph | H | CH$_3$ | CH$_3$ | CH$_3$ | |
| 458 | 5-F | 2-CF$_3$—Ph | H | CH$_3$ | CH$_3$ | CH$_3$ | |
| 459 | 5-F | 2-NO$_2$—Ph | H | CH$_3$ | CH$_3$ | CH$_3$ | |
| 460 | 5-F | 3-Cl—Ph | H | CH$_3$ | CH$_3$ | CH$_3$ | |
| 461 | 5-F | 3-F—Ph | H | CH$_3$ | CH$_3$ | CH$_3$ | |
| 462 | 5-F | 3-Br—Ph | H | CH$_3$ | CH$_3$ | CH$_3$ | |
| 463 | 5-F | 3-CH$_3$—Ph | H | CH$_3$ | CH$_3$ | CH$_3$ | |
| 464 | 5-F | 3-OCH$_3$—Ph | H | CH$_3$ | CH$_3$ | CH$_3$ | |
| 465 | 5-F | 3-SCH$_3$—Ph | H | CH$_3$ | CH$_3$ | CH$_3$ | |
| 466 | 5-F | 3-CF$_3$—Ph | H | CH$_3$ | CH$_3$ | CH$_3$ | |
| 467 | 5-F | 3-OCF$_2$H—Ph | H | CH$_3$ | CH$_3$ | CH$_3$ | |
| 468 | 5-F | 3-OCF$_2$CF$_2$H—Ph | H | CH$_3$ | CH$_3$ | CH$_3$ | |
| 469 | 5-F | 3-OCH$_2$CF$_3$—Ph | H | CH$_3$ | CH$_3$ | CH$_3$ | |
| 470 | 5-F | 3-NO$_2$—Ph | H | CH$_3$ | CH$_3$ | CH$_3$ | |
| 471 | 5-F | 4-OH—Ph | H | CH$_3$ | CH$_3$ | CH$_3$ | |
| 472 | 5-F | 4-OC$_2$H$_5$—Ph | H | CH$_3$ | CH$_3$ | CH$_3$ | |
| 473 | 5-F | 4-NHCH$_3$—Ph | H | CH$_3$ | CH$_3$ | CH$_3$ | |
| 474 | 5-F | 4-N(CH$_3$)$_2$—Ph | H | CH$_3$ | CH$_3$ | CH$_3$ | |
| 475 | 5-F | 2,4-Cl$_2$—Ph | H | CH$_3$ | CH$_3$ | CH$_3$ | |
| 476 | 5-F | 2,4-F$_2$—Ph | H | CH$_3$ | CH$_3$ | CH$_3$ | |
| 477 | 5-F | 3,4-Cl$_2$—Ph | H | CH$_3$ | CH$_3$ | CH$_3$ | |
| 478 | 5-F | 2,6-Cl$_2$—Ph | H | CH$_3$ | CH$_3$ | CH$_3$ | |
| 479 | 4-F | 4-Cl—Ph | H | CH$_3$ | CH$_3$ | CH$_3$ | n$_D^{24.5}$ 1.6279 |
| 480 | 4-F | 4-F—Ph | H | CH$_3$ | CH$_3$ | CH$_3$ | n$_D^{23.5}$ 1.6343 |
| 481 | 6-F | 4-Cl—Ph | H | CH$_3$ | CH$_3$ | CH$_3$ | m.p., 122.9° C. |
| 482 | 6-F | 4-F—Ph | H | CH$_3$ | CH$_3$ | CH$_3$ | m.p., 116.6° C. |
| 483 | 5-OPh | 4-Cl—Ph | H | CH$_3$ | CH$_3$ | CH$_3$ | m.p., 109.1° C. |
| 484 | 5-OPh | 4-F—Ph | H | CH$_3$ | CH$_3$ | CH$_3$ | |
| 485 | 5-Cl | H | H | CH$_3$ | CH$_3$ | CH$_3$ | |
| 486 | 5-Cl | CH$_3$ | H | CH$_3$ | CH$_3$ | CH$_3$ | n$_D^{24.5}$ 1.6352 |
| 487 | 5-Cl | C$_2$H$_5$ | H | CH$_3$ | CH$_3$ | CH$_3$ | n$_D^{23.0}$ 1.6326 |
| 488 | 5-Cl | n-C$_3$H$_7$ | H | CH$_3$ | CH$_3$ | CH$_3$ | |
| 489 | 5-Cl | i-C$_3$H$_7$ | H | CH$_3$ | CH$_3$ | CH$_3$ | |
| 490 | 5-Cl | n-C$_4$H$_9$ | H | CH$_3$ | CH$_3$ | CH$_3$ | |
| 491 | 5-Cl | OCH$_3$ | H | CH$_3$ | CH$_3$ | CH$_3$ | |
| 492 | 5-Cl | SCH$_3$ | H | CH$_3$ | CH$_3$ | CH$_3$ | |
| 493 | 5-Cl | CN | H | CH$_3$ | CH$_3$ | CH$_3$ | |
| 494 | 5-Cl | CO$_2$CH$_3$ | H | CH$_3$ | CH$_3$ | CH$_3$ | |
| 495 | 5-Cl | CO$_2$C$_2$H$_5$ | H | CH$_3$ | CH$_3$ | CH$_3$ | |
| 496 | 5-Cl | CO$_2$CH$_2$CF$_3$ | H | CH$_3$ | CH$_3$ | CH$_3$ | |
| 497 | 5-Cl | CO$_2$Ph | H | CH$_3$ | CH$_3$ | CH$_3$ | |
| 498 | 5-Cl | SO$_2$CH$_3$ | H | CH$_3$ | CH$_3$ | CH$_3$ | |
| 499 | 5-Cl | CONHCH$_3$ | H | CH$_3$ | CH$_3$ | CH$_3$ | |
| 500 | 5-Cl | CONHPh | H | CH$_3$ | CH$_3$ | CH$_3$ | |
| 501 | 5-Cl | C(S)N(CH$_3$)$_2$ | H | CH$_3$ | CH$_3$ | CH$_3$ | |
| 502 | 5-Cl | COCH$_3$ | H | CH$_3$ | CH$_3$ | CH$_3$ | |
| 503 | 5-Cl | COC$_2$H$_5$ | H | CH$_3$ | CH$_3$ | CH$_3$ | |
| 504 | 5-Cl | CH$_2$Ph | H | CH$_3$ | CH$_3$ | CH$_3$ | |
| 505 | 5-Cl | Cl$_2$Ph-4-Cl | H | CH$_3$ | CH$_3$ | CH$_3$ | n$_D^{24.0}$ 1.6359 |
| 506 | 5-Cl | CH$_2$Ph-4-F | H | CH$_3$ | CH$_3$ | CH$_3$ | n$_D^{23.8}$ 1.6322 |
| 507 | 5-Cl | CH$_2$CO$_2$C$_2$H$_5$ | H | CH$_3$ | CH$_3$ | CH$_3$ | |
| 508 | 5-Cl | CH$_2$OCH$_3$ | H | CH$_3$ | CH$_3$ | CH$_3$ | |
| 509 | 5-Cl | CH 2CH$_2$CN | H | CH$_3$ | CH$_3$ | CH$_3$ | |
| 510 | 5-F | CH$_3$ | H | CH$_3$ | CH$_3$ | CH$_3$ | |
| 511 | 5-F | C$_2$H$_5$ | H | CH$_3$ | CH$_3$ | CH$_3$ | |
| 512 | 5-F | i-C$_3$H$_7$ | H | CH$_3$ | CH$_3$ | CH$_3$ | |
| 513 | 5-F | CH$_2$Ph | H | CH$_3$ | CH$_3$ | CH$_3$ | |
| 514 | 5-F | CH$_2$Ph-4-Cl | H | CH$_3$ | CH$_3$ | CH$_3$ | |
| 515 | 5-F | CH$_2$Ph-4-F | H | CH$_3$ | CH$_3$ | CH$_3$ | |
| 516 | 5-Br | i-C$_3$H$_7$ | H | CH$_3$ | CH$_3$ | CH$_3$ | |
| 517 | 5-Br | CH$_2$Ph-4-Cl | H | CH$_3$ | CH$_3$ | CH$_3$ | |
| 518 | 5-Br | CH$_2$Ph-4-F | H | CH$_3$ | CH$_3$ | CH$_3$ | |
| 519 | 5-CF$_3$ | i-C$_3$H$_7$ | H | CH$_3$ | CH$_3$ | CH$_3$ | |
| 520 | 5-CF$_3$ | CH$_2$Ph-4-Cl | H | CH$_3$ | CH$_3$ | CH$_3$ | |
| 521 | 5-CF$_3$ | CH$_2$Ph-4-F | H | CH$_3$ | CH$_3$ | CH$_3$ | |
| 522 | 5-OCF$_3$ | i-C$_3$H$_7$ | H | CH$_3$ | CH$_3$ | CH$_3$ | |
| 523 | 5-OCF$_3$ | CH$_2$Ph-4-Cl | H | CH$_3$ | CH$_3$ | CH$_3$ | |
| 524 | 5-OCF$_2$ | CH$_2$Ph-4-F | H | CH$_3$ | CH$_3$ | CH$_3$ | |
| 525 | 5-OCF$_2$H | i-C$_3$H$_7$ | H | CH$_3$ | CH$_3$ | CH$_3$ | |

TABLE 1-continued (A=$CH_2$)

| Compound No. | $R^1$ | $R^2$ | $R^3$ | $R^4$ | $R^5$ | $R^6$ | Physical properties |
|---|---|---|---|---|---|---|---|
| 526 | 5-$OCF_2H$ | $CH_2Ph$-4-Cl | H | $CH_3$ | $CH_3$ | $CH_3$ | |
| 527 | 5-$OCF_2H$ | $CH_2Ph$-4-F | H | $CH_3$ | $CH_3$ | $CH_3$ | |
| 528 | 5-Cl | i-$C_3H_7$ | H | $CH_3$ | $C_2H_5$ | $CH_3$ | |
| 529 | 5-Cl | i-$C_3H_7$ | H | $CH_3$ | $C_2H_5$ | $CH_3$ | |
| 530 | 5-Cl | i-$C_3H_7$ | H | $CH_3$ | i-$C_3H_7$ | H | |
| 531 | 5-Cl | i-$C_3H_7$ | H | $CH_3$ | i-$C_3H_7$ | $CH_3$ | |
| 532 | 5-Cl | i-$C_3H_7$ | H | $CH_3$ | t-$C_4H_9$ | H | |
| 533 | 5-Cl | i-$C_3H_7$ | H | $CH_3$ | $CH_2CF_3$ | $CH_3$ | |
| 534 | 5-F | i-$C_3H_7$ | H | $CH_3$ | $C_2H_5$ | $CH_3$ | |
| 535 | 5-F | i-$C_3H_7$ | H | $CH_3$ | $C_2H_5$ | $C_2H_5$ | |
| 536 | 5-F | i-$C_3H_7$ | H | $CH_3$ | t-$C_4H_9$ | H | |
| 537 | 5-$CF_3$ | i-$C_3H_7$ | H | $CH_3$ | $C_2H_5$ | $CH_3$ | |
| 538 | 5-$CF_3$ | i-$C_3H_7$ | H | $CH_3$ | $C_2H_5$ | $C_2H_5$ | |
| 539 | 5-$CF_3$ | i-$C_3H_7$ | H | $CH_3$ | t-$C_4H_9$ | H | |
| 540 | 5-$OCH_2H$ | i-$C_3H_7$ | H | $CH_3$ | $C_2H_5$ | $CH_3$ | |
| 541 | 5-$OCF_2H$ | i-$C_3H_7$ | H | $CH_3$ | $C_2H_5$ | $C_2H_5$ | |
| 542 | 5-$OCF_2H$ | i-$C_3H_7$ | H | $CH_3$ | t-$C_4H_9$ | H | |
| 543 | 5-$OCF_3$ | i-$C_3H_7$ | H | $CH_3$ | $C_2H_5$ | $CH_3$ | |
| 545 | 5-$OCF_3$ | i-$C_3H_7$ | H | $CH_3$ | $C_2H_5$ | $C_2H_5$ | |
| 545 | 5-$OCF_3$ | i-$C_3H_7$ | H | $CH_3$ | t-$C_4H_9$ | H | |
| 546 | 5-Cl | i-$C_3H_7$ | H | $C_2H_5$ | $CH_3$ | $CH_3$ | |
| 547 | 5-Cl | i-$C_3H_7$ | H | i-$C_3H_7$ | $CH_3$ | $CH_3$ | |
| 548 | 5-Cl | i-$C_3H_7$ | H | n-$C_3H_7$ | $CH_3$ | $CH_3$ | |
| 549 | 5-Cl | i-$C_3H_7$ | H | t-$C_4H_9$ | $CH_3$ | $CH_3$ | |
| 550 | 5-Cl | i-$C_3H_7$ | H | $CF_3$ | $CH_3$ | $CH_3$ | |
| 551mix | 5-Cl | $CH_3$ | $CH_3$ | $CH_3$ | $CH_3$ | $CH_3$ | m.p., 78.2° C. |
| 552 | 5-Cl | $C_2H_5$ | $CH_3$ | $CH_3$ | $CH_3$ | $CH_3$ | $n_D^{23.0}$ 1.6050 |
| 553 | 5-Cl | n$C_3H_7$ | $CH_3$ | $CH_3$ | $CH_3$ | $CH_3$ | $n_D^{24.0}$ 1.5931 |
| 554 | 5-Cl | i-$C_3H_7$ | $CH_3$ | $CH_3$ | $CH_3$ | $CH_3$ | |
| 555 | 5-Cl | n$C_4H_9$ | $CH_3$ | $CH_3$ | $CH_3$ | $CH_3$ | $n_D^{24.0}$ 1. 5931 |
| 556 | 5-Cl | CN | $CH_3$ | $CH_3$ | $CH_3$ | $CH_3$ | |
| 557a | 5-Cl | $CO_2CH_3$ | $CH_3$ | $CH_3$ | $CH_3$ | $CH_3$ | m.p., 127.0° C. |
| 557b | | | | | | | viscous liquid |
| 558 | 5-Cl | $CO_2CH_3$ | $C_2H_5$ | $CH_3$ | $CH_3$ | $CH_3$ | |
| 559 | 5-Cl | $CO_2CH_3$ | n-$C_3H_5$ | $CH_3$ | $CH_3$ | $CH_3$ | |
| 560mix | 5-F | $CH_3$ | $CH_3$ | $CH_3$ | $CH_3$ | $CH_3$ | m.p., 122.3° C. |
| 561 | 5-F | $C_2H_5$ | $CH_3$ | $CH_3$ | $CH_3$ | $CH_3$ | |
| 562 | 5-F | i-$C_3H_7$ | $CH_3$ | $CH_3$ | $CH_3$ | $CH_3$ | |
| 563 | 5-F | n-$C_4H_9$ | $CH_3$ | $CH_3$ | $CH_3$ | $CH_3$ | |
| 564 | 5-F | $CH_2CH=CH_2$ | $CH_3$ | $CH_3$ | $CH_3$ | $CH_3$ | |
| 565 | 5-F | CN | $C_2H_5$ | $CH_3$ | $CH_3$ | $CH_3$ | |
| 566 | 5-$CF_2$ | $CH_3$ | $CH_3$ | $CH_3$ | $CH_3$ | $CH_3$ | |
| 567 | 5-$CF_2$ | $C_2H_5$ | $CH_3$ | $CH_3$ | $CH_3$ | $CH_3$ | |
| 568 | 5-$CF_3$ | i-$C_3H_7$ | $CH_3$ | $CH_3$ | $CH_3$ | $CH_3$ | |
| 569 | 5-$CF_3$ | n-$C_4H_9$ | $CH_3$ | $CH_3$ | $CH_3$ | $CH_3$ | |
| 570 | 5-$CF_3$ | CN | $CH_3$ | $CH_3$ | $CH_3$ | $CH_3$ | |
| 571 | 5-$CF_3$ | $CO_2CH_3$ | $CH_3$ | $CH_3$ | $CH_3$ | $CH_3$ | |
| 572 | 5-$OCF_3$ | $CH_3$ | $CH_3$ | $CH_3$ | $CH_3$ | $CH_3$ | |
| 573 | 5-$OCF_3$ | $C_2H_5$ | $CH_3$ | $CH_3$ | $CH_3$ | $CH_3$ | |
| 574 | 5-$OCF_3$ | i-$C_3H_7$ | $CH_3$ | $CH_3$ | $CH_3$ | $CH_3$ | |
| 575 | 5-$OCF_3$ | $CO_2CH_3$ | $CH_3$ | $CH_3$ | $CH_3$ | $CH_3$ | |
| 576 | 5-$OCF_3$ | CN | $CH_2Ph$ | $CH_3$ | $CH_3$ | $CH_3$ | |
| 577 | 5-$OCF_2H$ | $CH_3$ | $CH_3$ | $CH_3$ | $CH_3$ | $CH_3$ | |
| 578 | 5-$OCF_2H$ | $C_2H_5$ | $CH_3$ | $CH_3$ | $CH_3$ | $CH_3$ | |
| 579 | 5-$OCF_2H$ | i-$C_3H_7$ | $CH_3$ | $CH_3$ | $CH_3$ | $CH_3$ | |
| 580 | 5-$OCH_2H$ | $CO_2CH_3$ | $CH_3$ | $CH_3$ | $CH_3$ | $CH_3$ | |
| 581 | 5-$OCF_2H$ | CN | $CH_3$ | $CH_3$ | $CH_3$ | $CH_3$ | |
| 582 | 5-Cl | $CH_3$ | $CH_3$ | $CH_3$ | $C_2H_5$ | $CH_3$ | |
| 583 | 5-Cl | $CH_3$ | $CH_3$ | $CH_3$ | $C_2H_5$ | $C_2H_5$ | |
| 584 | 5-Cl | $CH_3$ | $CH_3$ | $CH_3$ | t-$C_4H_9$ | H | |
| 585 | 5-Cl | $C_2H_5$ | $CH_3$ | $CH_3$ | $C_2H_5$ | $CH_3$ | |
| 586 | 5-Cl | $C_2H_5$ | $CH_3$ | $CH_3$ | $C_2H_5$ | $C_2H_5$ | |
| 587 | 5-Cl | $C_2H_5$ | $CH_3$ | $CH_3$ | t-$C_4H_9$ | H | |
| 588 | 5-Cl | n-$C_3H_7$ | $CH_3$ | $CH_3$ | $C_2H_5$ | $CH_3$ | |
| 589 | 5-Cl | n-$C_3H_7$ | $CH_3$ | $CH_3$ | $C_2H_5$ | $C_2H_5$ | |
| 590 | 5-Cl | n-$C_3H_7$ | $CH_3$ | $CH_3$ | t-$C_4H_9$ | H | |
| 591 | 5-Cl | $CO_2CH_3$ | $CH_3$ | $CH_3$ | $C_2H_5$ | $CH_3$ | |
| 592 | 5-Cl | $CO_2CH_3$ | $CH_3$ | $CH_3$ | $C_2H_5$ | $C_2H_5$ | |
| 593 | 5-Cl | $CO_2CH_3$ | $CH_3$ | $CH_3$ | t-$C_4H_9$ | H | |
| 594 | 5-F | $CH_3$ | $CH_3$ | $CH_3$ | $C_2H_5$ | $CH_3$ | |
| 595 | 5-F | $CH_3$ | $CH_3$ | $CH_3$ | $C_2H_5$ | $C_2H_5$ | |
| 596 | 5-F | $CH_3$ | $CH_3$ | $CH_3$ | t-$C_4H_9$ | H | |
| 597 | 5-$OCF_3$ | $CH_3$ | $CH_3$ | $CH_3$ | $C_2H_5$ | $CH_3$ | |
| 598 | 5-$OCF_3$ | $CH_3$ | $CH_3$ | $CH_3$ | $C_2H_5$ | $C_2H_5$ | |
| 599 | 5-$OCF_2$ | $CH_3$ | $CH_3$ | $CH_3$ | t-$C_4H_9$ | H | |
| 600 | 5-$OCF_2H$ | $CH_3$ | $CH_3$ | $CH_3$ | $C_2H_5$ | $CH_3$ | |
| 601 | 5-$OCF_2H$ | $CH_3$ | $CH_3$ | $CH_3$ | $C_2H_5$ | $C_2H_5$ | |
| 602 | 5-$OCF_2H$ | $CH_3$ | $CH_3$ | $CH_3$ | t-$C_4H_9$ | H | |
| 603 | 5-Cl | $CO_2CH_3$ | $CH_2Ph$ | $CH_3$ | $CH_3$ | $CH_3$ | |

TABLE 1-continued (A=CH₂)

| Compound No. | $R^1$ | $R^2$ | $R^3$ | $R^4$ | $R^5$ | $R^6$ | Physical properties |
|---|---|---|---|---|---|---|---|
| 604 | 5-Cl | CO₂CH₃ | CH₂CH=CH₂ | CH₃ | CH₃ | CH₃ | |
| 605 | 5-Cl | CN | CH₂Ph | CH₃ | CH₃ | CH₃ | |
| 606 | 5-Cl | CN | C₂H₅ | CH₃ | CH₃ | CH₃ | |
| 607 | 5-Cl | 4-CH₃—Ph | H | CH₃ | CH₃ | CH₃ | m.p., 128.7° C. |
| 608 | 5,6-Cl₂ | 4-F—Ph | H | CH₃ | CH₃ | CH₃ | m.p., 139.8° C. |
| 609 | 5-F | H | H | CH₃ | CH₃ | CH₃ | m.p., 122.3° C. |
| 610 | 5-OCH₃ | H | H | CH₃ | CH₃ | CH₃ | m.p., 102.5° C. |

TABLE 2

(A=OCH₃)

| Compound No. | $R^1$ | $R^2$ | $R^3$ | $R^4$ | $R^5$ | $R^6$ | Physical properties |
|---|---|---|---|---|---|---|---|
| 611 | 5-Cl | Ph | H | CH₃ | CH₃ | CH₃ | |
| 612 | 5-Cl | 4-Cl—Ph | H | CH₃ | CH₃ | CH₃ | |
| 613 | 5-Cl | 4-F—Ph | H | CH₃ | CH₃ | CH₃ | |
| 614 | 5-Cl | 4-Br—Ph | H | CH₃ | CH₃ | CH₃ | |
| 615 | 5-Cl | 4-CH₃—Ph | H | CH₃ | CH₃ | CH₃ | |
| 616 | 5-Cl | 4-OH₃—Ph | H | CH₃ | CH₃ | CH₃ | |
| 617 | 5-Cl | 4-SCH₃—Ph | H | CH₃ | CH₃ | CH₃ | |
| 618 | 5-Cl | 4-CF₃—Ph | H | CH₃ | CH₃ | CH₃ | |
| 619 | 5-Cl | 4-OCFhd 3—Ph | H | CH₃ | CH₃ | CH₃ | |
| 620 | 5-Cl | 4-OCF₂H—Ph | H | CH₃ | CH₃ | CH₃ | |
| 621 | 5-Cl | 4-OCF₂CF₂H—Ph | H | CH₃ | CH₃ | CH₃ | |
| 622 | 5-Cl | 4-OCH₂CF₃—Ph | H | CH₃ | CH₃ | CH₃ | |
| 623 | 5-Cl | 4-NO₂—Ph | H | CH₃ | CH₃ | CH₃ | |
| 624 | 5-Cl | 4-CN—Ph | H | CH₃ | CH₃ | CH₃ | |
| 625 | 5-Cl | 3-Cl—Ph | H | CH₃ | CH₃ | CH₃ | |
| 626 | 5-Cl | 3-F—Ph | H | CH₃ | CH₃ | CH₃ | |
| 627 | 5-Cl | 3-CF₃—Ph | H | CH₃ | CH₃ | CH₃ | |
| 628 | 5-Cl | 3-OCF₂H—Ph | H | CH₃ | CH₃ | CH₃ | |
| 629 | 5-Cl | 4-Cl—Ph | H | CH₃ | C₂H₅ | CH₃ | |
| 630 | 5-Cl | 4-Cl—Ph | H | CH₃ | C₂H₅ | C₂H₅ | |
| 631 | 5-Cl | 4-Cl—Ph | H | CH₃ | t-C₄H₉ | H | |
| 632 | 5-Cl | 4-Cl—Ph | CH₃ | CH₃ | CH₃ | CH₃ | |
| 633 | 5-Cl | 4-F—Ph | H | CH₃ | CH₃ | CH₃ | |
| 634 | 5-Cl | 4-F—Ph | H | CH₃ | C₂H₅ | CH₃ | |
| 635 | 5-Cl | 4-F—Ph | H | CH₃ | C₂H₅ | C₂H₅ | |
| 636 | 5-Cl | 4-F—Ph | H | CH₃ | t-C₄H₉ | H | |
| 637 | 5-Cl | 4-F—Ph | H | H | CH₃ | CH₃ | |
| 638 | 5-Cl | 4-F—Ph | H | C₂H₅ | CH₃ | CH₃ | |
| 639 | 5-Cl | 4-F—Ph | H | i-C₃H₇ | CH₃ | CH₃ | |
| 640 | 5-Cl | 4-F—Ph | CH₃ | CH₃ | CH₃ | CH₃ | |
| 641 | 5-F | 4-Cl—Ph | H | CH₃ | CH₃ | CH₃ | |
| 642 | 5-F | 4-Cl—Ph | H | CH₃ | C₂H₅ | CH₃ | |
| 643 | 5-F | 4-Cl—Ph | H | CH₃ | C₂H₅ | C₂H₅ | |
| 644 | 5-F | 4-Cl—Ph | H | CH₃ | t-C₄H₉ | H | |
| 645 | 5-F | 4-Cl—Ph | CH₃ | CH₃ | CH₃ | CH₃ | |
| 646 | 5-F | 4-F—Ph | H | CH₃ | CH₃ | CH₃ | |
| 647 | 5-F | 4-F—Ph | H | CH₃ | C₂H₅ | CH₃ | |
| 648 | 5-F | 4-F—Ph | H | CH₃ | C₂H₅ | C₂H₅ | |
| 649 | 5-F | 4-F—Ph | H | CH₃ | t-C₄H₉ | H | |
| 650 | 5-F | 4-F—Ph | CH₃ | CH₃ | CH₃ | CH₃ | |
| 651 | 5-OCF₂H | 4-Cl—Ph | H | CH₃ | CH₃ | CH₃ | |
| 652 | 5-OCF₂H | 4-F—Ph | H | CH₃ | CH₃ | CH₃ | |
| 653 | 5-OCF₂H | 4-OCF₂H—Ph | H | CH₃ | CH₃ | CH₃ | |
| 654 | 5-OCF₃ | 4-Cl—Ph | H | CH₃ | CH₃ | CH₃ | |
| 655 | 5-OCF₂CF₂H | 4-Cl—Ph | H | CH₃ | CH₃ | CH₃ | |
| 656 | 5-OCH₂CF₃ | 4-Cl—Ph | H | CH₃ | CH₃ | CH₃ | |
| 657 | 5-OCH₃ | 4-Cl—Ph | H | CH₃ | CH₃ | CH₃ | |
| 658 | 5-SCH₃ | 4-Cl—Ph | H | CH₃ | CH₃ | CH₃ | |
| 659 | 5-NO₂ | 4-Cl—Ph | H | CH₃ | CH₃ | CH₃ | |
| 660 | 5-CN | 4-Cl—Ph | H | CH₃ | CH₃ | CH₃ | |
| 661 | 4-CN | 4-Cl—Ph | H | CH₃ | CH₃ | CH₃ | |
| 662 | 4-Cl | 4-F—Ph | H | CH₃ | CH₃ | CH₃ | |
| 663 | 4-F | 4-Cl—Ph | H | CH₃ | CH₃ | CH₃ | |
| 664 | 4-F | 4-F—Ph | H | CH₃ | CH₃ | CH₃ | |
| 665 | 6-Cl | 4-Cl—Ph | H | CH₃ | CH₃ | CH₃ | |
| 666 | 6-Cl | 4-F—Ph | H | CH₃ | CH₃ | CH₃ | |
| 667 | 6-F | 4-Cl—Ph | H | CH₃ | CH₃ | CH₃ | |
| 668 | 6-F | 4-F—Ph | H | CH₃ | CH₃ | CH₃ | |
| 669 | 5-Cl | H | H | CH₃ | CH₃ | CH₃ | m.p., 75.2° C. |
| 670 | 5-Cl | CH₃ | H | CH₃ | CH₃ | CH₃ | |
| 671 | 5-Cl | C₂H₅ | H | CH₃ | CH₃ | CH₃ | |
| 672 | 5-Cl | n-C₃H₇ | H | CH₃ | CH₃ | CH₃ | |
| 673 | 5-Cl | i-C₃H₇ | H | CH₃ | CH₃ | CH₃ | |
| 674 | 5-Cl | n-C₄H₉ | H | CH₃ | CH₃ | CH₃ | |

TABLE 2-continued (A=OCH₃)

| Compound No. | $R^1$ | $R^2$ | $R^3$ | $R^4$ | $R^5$ | $R^6$ | Physical properties |
|---|---|---|---|---|---|---|---|
| 675 | 5-Cl | CH₂CH(CH₃)₂ | H | CH₃ | CH₃ | CH₃ | |
| 676 | 5-Cl | CH₂CH=CH₂ | H | CH₃ | CH₃ | CH₃ | |
| 677 | 5-Cl | CH₂C≡CH | H | CH₃ | CH₃ | CH₃ | |
| 678 | 5-Cl | CH₂Ph | H | CH₃ | CH₃ | CH₃ | |
| 679 | 5-Cl | CH₂Ph-4-Cl | H | CH₃ | CH₃ | CH₃ | |
| 680 | 5-Cl | CH₂Ph-4-F | H | CH₃ | CH₃ | CH₃ | |
| 681 | 5-Cl | CH₂CF₃ | H | CH₃ | CH₃ | CH₃ | |
| 682 | 5-Cl | CH₂OCH₃ | H | CH₃ | CH₃ | CH₃ | |
| 683 | 5-Cl | CO₂CH₃ | H | CH₃ | CH₃ | CH₃ | |
| 684 | 5-Cl | CO₂C₂H₅ | H | CH₃ | CH₃ | CH₃ | |
| 685 | 5-Cl | CO₂CH₂CF₃ | H | CH₃ | CH₃ | CH₃ | |
| 686 | 5-Cl | CO₂Ph | H | CH₃ | CH₃ | CH₃ | |
| 687 | 5-Cl | SO₂CH₃ | H | CH₃ | CH₃ | CH₃ | |
| 688 | 5-Cl | CON(CH₃)₂ | H | CH₃ | CH₃ | CH₃ | |
| 689 | 5-Cl | CONHCH₃ | H | CH₃ | CH₃ | CH₃ | |
| 690 | 5-Cl | CONHPh | H | CH₃ | CH₃ | CH₃ | |
| 691 | 5-F | CH₃ | H | CH₃ | CH₃ | CH₃ | |
| 692 | 5-F | C₂H₅ | H | CH₃ | CH₃ | CH₃ | |
| 693 | 5-F | n-C₃H₇ | H | CH₃ | CH₃ | CH₃ | |
| 694 | 5-F | i-C₃H₇ | H | CH₃ | CH₃ | CH₃ | |
| 695 | 5-F | n-C₄H₉ | H | CH₃ | CH₃ | CH₃ | |
| 696 | 5-F | CH₂CH=CH₂ | H | CH₃ | CH₃ | CH₃ | |
| 697 | 5-F | CH₂C≡CH | H | CH₃ | CH₃ | CH₃ | |
| 698 | 5-F | CH₂Ph | H | CH₃ | CH₃ | CH₃ | |
| 699 | 5-F | CH₂Ph-4-Cl | H | CH₃ | CH₃ | CH₃ | |
| 700 | 5-F | CH₂Ph-4-F | H | CH₃ | CH₃ | CH₃ | |
| 701 | 5-F | CO₂CH₃ | H | CH₃ | CH₃ | CH₃ | |
| 702 | 5-Br | C₂H₅ | H | CH₃ | CH₃ | CH₃ | |
| 703 | 5-Br | n-C₃H₇ | H | CH₃ | CH₃ | CH₃ | |
| 704 | 5-Br | i-C₃H₇ | H | CH₃ | CH₃ | CH₃ | |
| 705 | 5-OCF₂H | CH₃ | H | CH₃ | CH₃ | CH₃ | |
| 706 | 5-OCF₂H | C₂H₅ | H | CH₃ | CH₃ | CH₃ | |
| 707 | 5-OCF₂H | n-C₃H₇ | H | CH₃ | CH₃ | CH₃ | |
| 708 | 5-OCF₂H | i-C₃H₇ | H | CH₃ | CH₃ | CH₃ | |
| 709 | 5-OCF₂H | n-C₄H₉ | H | CH₃ | CH₃ | CH₃ | |
| 710 | 5-OCF₂H | CH₂Ph-4-Cl | H | CH₃ | CH₃ | CH₃ | |
| 711 | 5-OCF₂H | CH₂Ph-4-F | H | CH₃ | CH₃ | CH₃ | |
| 712 | 5-OCF₂H | CO₂CH₃ | H | CH₃ | CH₃ | CH₃ | |
| 713 | 5-Cl | i-C₃H₇ | H | CH₃ | C₂H₅ | CH₃ | |
| 714 | 5-Cl | i-C₃H₇ | H | CH₃ | C₂H₅ | C₂H₅ | |
| 715 | 5-Cl | i-C₃H₇ | H | CH₃ | t-C₄H₉ | H | |
| 716 | 5-F | i-C₃H₇ | H | CH₃ | C₂H₅ | CH₃ | |
| 717 | 5-F | i-C₃H₇ | H | CH₃ | C₂H₅ | C₂H₅ | |
| 718 | 5-F | i-C₃H₇ | H | CH₃ | t-C₄H₉ | H | |
| 719 | 5-F | i-C₃H₇ | H | H | CH₃ | CH₃ | |
| 720 | 5-F | i-C₃H₇ | H | C₂H₅ | CH₃ | CH₃ | |
| 721 | 5-F | i-C₃H₇ | H | n-C₃H₇ | CH₃ | CH₃ | |
| 722 | 5-F | i-C₃H₇ | H | i-C₃H₇ | CH₃ | CH₃ | |
| 723 | 5-F | i-C₃H₇ | H | CF₃ | CH₃ | CH₃ | |
| 724 | 5-F | CH₃ | CH₃ | CH₃ | CH₃ | CH₃ | |
| 725 | 5-F | C₂H₅ | CH₃ | CH₃ | CH₃ | CH₃ | |
| 726 | 5-F | n-C₃H₇ | CH₃ | CH₃ | CH₃ | CH₃ | |
| 727 | 5-F | i-C₃H₇ | CH₃ | CH₃ | CH₃ | CH₃ | |
| 728 | 5-F | n-C₄H₉ | CH₃ | CH₃ | CH₃ | CH₃ | |
| 729 | 5-F | CH₂CH=CH₂ | CH₃ | CH₃ | CH₃ | CH₃ | |
| 730 | 5-F | CH₂C≡CH | CH₃ | CH₃ | CH₃ | CH₃ | |
| 731 | 5-F | CO₂CH₃ | CH₃ | CH₃ | CH₃ | CH₃ | |
| 732 | 5-CF₃ | i-C₃H₇ | H | CH₃ | CH₃ | CH₃ | |
| 733 | 5-OCF₃ | i-C₃H₇ | H | CH₃ | CH₃ | CH₃ | |

TABLE 3

(A=O)

| Compound No. | $R^1$ | $R^2$ | $R^3$ | $R^4$ | $R^5$ | $R^6$ | Physical properties |
|---|---|---|---|---|---|---|---|
| 734 | 5-Cl | 4-Cl—Ph | H | CH₃ | CH₃ | CH₃ | |
| 735 | 5-Cl | 4-Cl—Ph | H | CH₃ | C₂H₅ | CH₃ | |
| 736 | 5-Cl | 4-Cl—Ph | H | CH₃ | C₂H₅ | C₂H₅ | |
| 737 | 5-Cl | 4-Cl—Ph | H | CH₃ | t-C₄H₉ | H | |
| 738 | 5-Cl | 4-Cl—Ph | H | C₂H₅ | CH₃ | CH₃ | |
| 739 | 5-Cl | 4-Cl—Ph | H | n-C₃H₇ | CH₃ | CH₃ | |
| 740 | 5-Cl | 4-Cl—Ph | H | i-C₃H₇ | CH₃ | CH₃ | |
| 741 | 5-Cl | 4-Cl—Ph | H | CF₃ | CH₃ | CH₃ | |
| 742 | 5-Cl | 4-F—Ph | H | CF₃ | CH₃ | CH₃ | |
| 743 | 5-F | 4-F—Ph | H | CF₃ | CH₃ | CH₃ | |
| 744 | 5-Br | 4-F—Ph | H | CF₃ | CH₃ | CH₃ | |
| 745 | 5-CF₃ | 4-F—Ph | H | CF₃ | CH₃ | CH₃ | |

TABLE 3-continued

| | | (A=O) | | | | |
|---|---|---|---|---|---|---|
| Compound No. | R¹ | R² | R³ | R⁴ | R⁵ | R⁶ | Physical properties |
| 746 | 5-OCF₃ | 4-F—Ph | H | CF₃ | CH₃ | CH₃ | |

TABLE 4

| | | (A=S) | | | | |
|---|---|---|---|---|---|---|
| Compound No. | R¹ | R² | R³ | R⁴ | R⁵ | R⁶ | properties |
| 747 | 5-Cl | Ph | H | CH₃ | CH₃ | CH₃ | |
| 748 | 5-Cl | 4-Cl—Ph | H | CH₃ | CH₃ | CH₃ | |
| 749 | 5-Cl | 4-F—Ph | H | CH₃ | CH₃ | CH₃ | |
| 750 | 5-Cl | 4-Br—Ph | H | CH₃ | CH₃ | CH₃ | |
| 751 | 5-Cl | 4-CF₃—Ph | H | CH₃ | CH₃ | CH₃ | |
| 752 | 5-Cl | 4-OCF₃—Ph | H | CH₃ | CH₃ | CH₃ | |
| 753 | 5-Cl | 4-OCF₂H—Ph | H | CH₃ | CH₃ | CH₃ | |
| 754 | 5-F | Ph | H | CH₃ | CH₃ | CH₃ | |
| 755 | 5-F | 4-Cl—Ph | H | CH₃ | CH₃ | CH₃ | |
| 756 | 5-F | 4-F—Ph | H | CH₃ | CH₃ | CH₃ | |
| 757 | 5-F | 4-CF₃—Ph | H | CH₃ | CH₃ | CH₃ | |
| 758 | 5-F | 4-OCF₃—Ph | H | CH₃ | CH₃ | CH₃ | |
| 759 | 5-F | 4-OCF₂H—Ph | H | CH₃ | CH₃ | CH₃ | |
| 760 | 5-CF₃ | Ph | H | CH₃ | CH₃ | CH₃ | |
| 761 | 5-CF₃ | 4-Cl—Ph | H | CH₃ | CH₃ | CH₃ | |
| 762 | 5-CF₃ | 4-F—Ph | H | CH₃ | CH₃ | CH₃ | |
| 763 | 5-CF₃ | 4-CF₃—Ph | H | CH₃ | CH₃ | CH₃ | |
| 764 | 5-CF₃ | 4-OCF₃—Ph | H | CH₃ | CH₃ | CH₃ | |
| 765 | 5-CF₃ | 4-OCF₂H—Ph | H | CH₃ | CH₃ | CH₃ | |
| 766 | 5-OCF₂H | 4-Cl—Ph | H | CH₃ | CH₃ | CH₃ | |
| 767 | 5-OCF₂H | 4-F—Ph | H | CH₃ | CH₃ | CH₃ | |
| 768 | 5-OCF₂H | 4-OCF₂H—Ph | H | CH₃ | CH₃ | CH₃ | |
| 769 | 5-Cl | 4-Cl—Ph | H | CH₃ | C₂H₅ | CH₃ | |
| 770 | 5-Cl | 4-Cl—Ph | H | CH₃ | C₂H₅ | C₂H₅ | |
| 771 | 5-Cl | 4-Cl—Ph | H | CH₃ | t-C₄H₉ | H | |
| 772 | 5-Cl | 4-Cl—Ph | H | H | CH₃ | CH₃ | |
| 773 | 5-Cl | 4-Cl—Ph | H | C₂H₅ | CH₃ | CH₃ | |
| 774 | 5-Cl | 4-Cl—Ph | H | n-C₃H₇ | CH₃ | CH₃ | |
| 775 | 5-Cl | 4-Cl—Ph | H | i-C₃H₇ | CH₃ | CH₃ | |
| 776 | 5-Cl | 4-Cl—Ph | H | CF₃ | CH₃ | CH₃ | |
| 777 | 5-Cl | 5-F—Ph | H | CH₃ | C₂H₅ | CH₃ | |
| 778 | 5-Cl | 5-F—Ph | H | CH₃ | C₂H₅ | C₂H₅ | |
| 779 | 5-Cl | 5-F—Ph | H | CH₃ | t-C₄H₉ | H | |

TABLE 5

| | | (A=CH₂CH₂) | | | | |
|---|---|---|---|---|---|---|
| Compound No. | R¹ | R² | R³ | R⁴ | R⁵ | R⁶ | properties |
| 780 | 5-Cl | 4-Cl—Ph | H | CH₃ | CH₃ | CH₃ | m.p., 170.4° C. |
| 781 | 5-Cl | 4-F—Ph | H | CH₃ | CH₃ | CH₃ | |
| 782 | 5-Cl | 4-OCF₂H—Ph | H | CH₃ | CH₃ | CH₃ | |
| 783 | 4-Cl | 4-Cl—Ph | H | CH₃ | CH₃ | CH₃ | resinous solid |
| 784 | 4-Cl | 4-F—Ph | H | CH₃ | CH₃ | CH₃ | |
| 785 | 6-Cl | 4-Cl—Ph | H | CH₃ | CH₃ | CH₃ | m.p., 124.4° C. |
| 786 | 6-Cl | 4-Cl—Ph | H | CH₃ | CH₃ | CH₃ | |
| 787 | 5-F | 4-Cl—Ph | H | CH₃ | CH₃ | CH₃ | |
| 788 | 5-F | 4-Cl—Ph | H | CH₃ | C₂H₅ | CH₃ | |
| 789 | 5-F | 4-Cl—Ph | H | CH₃ | t-C₄H₉ | H | |
| 790 | 5-F | 4-Cl—Ph | H | CH₃ | CH₂CF₃ | H | |
| 791 | 5-F | 4-Cl—Ph | H | H | CH₃ | CH₃ | |
| 792 | 5-F | 4-Cl—Ph | H | C₂H₅ | CH₃ | CH₃ | |
| 793 | 5-F | 4-Cl—Ph | H | n-C₃H₃ | CH₃ | CH₃ | |
| 794 | 5-F | 4-Cl—Ph | H | i-C₃H₇ | CH₃ | CH₃ | |
| 795 | 5-F | 4-Cl—Ph | H | CF₃ | CH₃ | CH₃ | |
| 796 | 5-F | 4-Cl—Ph | CH₃ | CH₃ | CH₃ | CH₃ | |
| 797 | 5-F | 4-F—Ph | H | CH₃ | CH₃ | CH₃ | |
| 798 | 5-F | 4-Br—Ph | H | CH₃ | CH₃ | CH₃ | |
| 799 | 5-F | 4-SCH₃—Ph | H | CH₃ | CH₃ | CH₃ | |
| 800 | 5-F | 4-CF₃—Ph | H | CH₃ | CH₃ | CH₃ | |
| 801 | 5-F | 4-OCF₃—Ph | H | CH₃ | CH₃ | CH₃ | |
| 802 | 5-F | 4-OCF₂H—Ph | H | CH₃ | CH₃ | CH₃ | |
| 803 | 5-F | 4-OCF₂CF₂H—Ph | H | CH₃ | CH₃ | CH₃ | |
| 804 | 5-F | 4-OCH₂CF₃—Ph | H | CH₃ | CH₃ | CH₃ | |
| 805 | 5-F | 4-NO₂—Ph | H | CH₃ | CH₃ | CH₃ | |
| 806 | 5-F | 4-CN—Ph | H | CH₃ | CH₃ | CH₃ | |
| 807 | 5-F | H | H | CH₃ | CH₃ | CH₃ | |
| 808 | 5-F | CH₃ | H | CH₃ | CH₃ | CH₃ | |

TABLE 5-continued (A=CH₂CH₂)

| Compound No. | R¹ | R² | R³ | R⁴ | R⁵ | R⁶ | properties |
|---|---|---|---|---|---|---|---|
| 809 | 5-F | C₂H₅ | H | CH₃ | CH₃ | CH₃ | |
| 810 | 5-F | n-C₃H₇ | H | CH₃ | CH₃ | CH₃ | |
| 811 | 5-F | i-C₃H₇ | H | CH₃ | CH₃ | CH₃ | |
| 812 | 5-F | n-C₄H₉ | H | CH₃ | CH₃ | CH₃ | |
| 813 | 5-F | i-C₄H₉ | H | CH₃ | CH₃ | CH₃ | |
| 814 | 5-F | CH₂CH=CH₃ | H | CH₃ | CH₃ | CH₃ | |
| 815 | 5-F | CH₂C≡CH | H | CH₃ | CH₃ | CH₃ | |
| 816 | 5-F | CH₂Ph | H | CH₃ | CH₃ | CH₃ | |
| 817 | 5-F | CH₂Ph-4-Cl | H | CH₃ | CH₃ | CH₃ | |
| 818 | 5-F | CH₂Ph-4-F | H | CH₃ | CH₃ | CH₃ | |
| 819 | 5-F | CH₂CF₃ | H | CH₃ | CH₃ | CH₃ | |
| 820 | 5-F | CH₂OCH₃ | H | CH₃ | CH₃ | CH₃ | |
| 821 | 5-F | CO₂OH₃ | H | CH₃ | CH₃ | CH₃ | |
| 822 | 5-F | CO₂C₂H₅ | H | CH₃ | CH₃ | CH₃ | |
| 823 | 5-F | CO₂Ph | H | CH₃ | CH₃ | CH₃ | |
| 824 | 5-F | CO₂CH₂CF₃ | H | CH₃ | CH₃ | CH₃ | |
| 825 | 5-F | SO₂CH₃ | H | CH₃ | CH₃ | CH₃ | |
| 826 | 5-F | CONHCH₃ | H | CH₃ | CH₃ | CH₃ | |
| 827 | 5-F | CON(CH₃)₂ | H | CH₃ | CH₃ | CH₃ | |
| 828 | 5-F | CONHPh | H | CH₃ | CH₃ | CH₃ | |
| 829 | 4-F | 4-Cl—Ph | H | CH₃ | CH₃ | CH₃ | |
| 830 | 4-F | 4-F—Ph | H | CH₃ | CH₃ | CH₃ | |
| 831 | 6-F | 4-Cl—Ph | H | CH₃ | CH₃ | CH₃ | |
| 832 | 6-F | 4-F—Ph | H | CH₃ | CH₃ | CH₃ | |
| 833 | 5-Br | 4-Cl—Ph | H | CH₃ | CH₃ | CH₃ | |
| 834 | 5-Br | 4-F—Ph | H | CH₃ | CH₃ | CH₃ | |
| 835 | 5-CH₃ | 4-Cl—Ph | H | CH₃ | CH₃ | CH₃ | |
| 836 | 5-CH₃ | 4-F—Ph | H | CH₃ | CH₃ | CH₃ | |
| 837 | 5-OCH₃ | 4-Cl—Ph | H | CH₃ | CH₃ | CH₃ | |
| 838 | 5-SCH₃ | 4-Cl—Ph | H | CH₃ | CH₃ | CH₃ | |
| 839 | 5-CF₃ | 4-Cl—Ph | H | CH₃ | CH₃ | CH₃ | |
| 840 | 5-CF₃ | 4-F—Ph | H | CH₃ | CH₃ | CH₃ | |
| 841 | 5-OCF₃ | 4-Cl—Ph | H | CH₃ | CH₃ | CH₃ | |
| 842 | 5-OCF₃ | 4-F—Ph | H | CH₃ | CH₃ | CH₃ | |
| 843 | 5-OCF₂H | 4-Cl—Ph | H | CH₃ | CH₃ | CH₃ | |
| 844 | 5-OCF₂H | 4-F—Ph | H | CH₃ | CH₃ | CH₃ | |
| 845 | 5-NO₂ | 4-Cl—Ph | H | CH₃ | CH₃ | CH₃ | |
| 846 | 5-CN | 4-Cl—Ph | H | CH₃ | CH₃ | CH₃ | |
| 847 | 5-Cl | 4-OCF₂H | H | CH₃ | CH₃ | CH₃ | |
| 848 | 5-F | 4-OCF₂H | H | CH₃ | CH₃ | CH₃ | |
| 849 | 5-CF₃ | 4-OCF₂H | H | CH₃ | CH₃ | CH₃ | |
| 850 | 5-OCF₃ | 4-OCF₂H | H | CH₃ | CH₃ | CH₃ | |
| 851 | H | CH₃ | H | CH₃ | CH₃ | CH₃ | m.p., 54.6° C. |

TABLE 6

(A=CH₂)

| Compound No. | R¹ | R² | R³ | R⁴ | R⁵ | R⁶ | Physical properties |
|---|---|---|---|---|---|---|---|
| 852 | 5-Cl | 2-Cl—Ph | H | CH₃ | CH₃ | CH₃ | m.p., 172.9° C. |
| 853 | 5-Cl | 2,6-Cl₂—Ph | H | CH₃ | CH₃ | CH₃ | m.p., 146.8° C. |
| 854 | 5-Cl | 3,4-F₂—Ph | H | CH₃ | CH₃ | CH₃ | m.p., 124.6° C. |
| 855 | 5-Cl | 4-OCH₂Ph—Ph | H | CH₃ | CH₃ | CH₃ | $n_D^{24.0}$ 1.5728 |
| 856a | 5-Cl | 4-Cl—Ph | C₂H₅ | CH₃ | CH₃ | CH₃ | m.p., 116.9° C. |
| 856b | 5-Cl | 4-Cl—Ph | C₂H₅ | CH₃ | CH₃ | CH₃ | $n_D^{25.5}$ 1.6137 |
| 857a | 5-Cl | 4-Cl—Ph | n-C₃H₇ | CH₃ | CH₃ | CH₃ | m.p., 156.1° C. |
| 857b | 5-Cl | 4-Cl—Ph | n-C₃H₇ | CH₃ | CH₃ | CH₃ | $n_D^{25.5}$ 1.6060 |
| 858a | 5-Cl | 4-Cl—Ph | n-C₄H₉ | CH₃ | CH₃ | CH₃ | m.p., 146.3° C. |
| 858b | 5-Cl | 4-Cl—Ph | n-C₄H₉ | CH₃ | CH₃ | CH₃ | $n_D^{24.0}$ 1.6067 |
| 859 | 5-Cl | -(CH₂)₄- | | CH₃ | CH₃ | CH₃ | $n_D^{24.5}$ 1.6271 |
| 860 | 5-Cl | -(CH₂)₅- | CH₃ | CH₃ | CH₃ | CH₃ | $n_D^{24.0}$ 1.6249 |
| 861 | 5-F | -(CH₂)₅- | | CH₃ | CH₃ | CH₃ | $n_D^{24.5}$ 1.5952 |
| 862 | 5-Cl | CH₂CH=CH₂ | CH₃ | CH₃ | CH₃ | CH₃ | $n_D^{24.0}$ 1.5950 |
| 863 | 5-Cl | CH₂CH=CH₂ | CH₂CH=CH₂ | CH₃ | CH₃ | CH₃ | $n_D^{20.5}$ 1.6040 |
| 864 | 5-Cl | CH₂CH=CH₂ | H | CH₃ | CH₃ | CH₃ | m.p., 111.6° C. |
| 865 | 5-Cl | CH₂C≡CH | H | CH₃ | CH₃ | CH₃ | $n_D^{25.0}$ 1.6107 |
| 866 | 5-Cl | CH₂C≡CH | CH₂C≡CH | CH₃ | CH₃ | CH₃ | $n_D^{24.0}$ 1.6103 |
| 867 | 5-OCF₂H | CH₃ | CH₃ | CH₃ | CH₃ | CH₃ | m.p., 58.6° C. |
| 868 | 5-Cl | CH₂CF₃ | CH₃ | CH₃ | CH₃ | CH₃ | m.p., 85.8° C. |
| 869 | 5-F | CH₂CF₃ | CH₃ | CH₃ | CH₃ | CH₃ | |
| 870 | 5-Cl | t-C₄H₉ | H | CH₃ | CH₃ | CH₃ | |
| 871 | 5-F | t-C₄H₉ | H | CH₃ | CH₃ | CH₃ | |

TABLE 7

(A=O)

| Compound No. | $R^1$ | $R^2$ | $R^3$ | $R^4$ | $R^5$ | $R^6$ | Physical properties |
|---|---|---|---|---|---|---|---|
| 872 mix | 5-Cl | $CH_3$ | H | $CH_3$ | $CH_3$ | $CH_3$ | m.p., 72.5° C. |
| 873 mix | 5-Cl | $C_2H_5$ | H | $CH_3$ | $CH_3$ | $CH_3$ | m.p., 88.3° C. |
| 874 | 5-Cl | n-$C_3H_7$ | H | $CH_3$ | $CH_3$ | $CH_3$ | |
| 875 | 5-Cl | i-$C_3H_7$ | H | $CH_3$ | $CH_3$ | $CH_3$ | |
| 876 | 5-Cl | $CH_3$ | $CH_3$ | $CH_3$ | $CH_3$ | $CH_3$ | |
| 877 | 5-Cl | $C_2H_5$ | $CH_3$ | $CH_3$ | $CH_3$ | $CH_3$ | |
| 878 | 5-Cl | $CH_2CH=CH_2$ | $CH_3$ | $CH_3$ | $CH_3$ | $CH_3$ | m.p., 81.7° C. |
| 879 | 5-Cl | $CH_2C\equiv CH$ | $CH_3$ | $CH_3$ | $CH_3$ | $CH_3$ | m.p., 86.5° C. |
| 880 | 5-F | $CH_2CH=CH_2$ | H | $CH_3$ | $CH_3$ | $CH_3$ | |
| 881 | 5-F | $CH_2C\equiv CH$ | H | $CH_3$ | $CH_3$ | $CH_3$ | |
| 882 | 5-F | $CH_2C=CH_2$ | $CH_3$ | $CH_3$ | $CH_3$ | $CH_3$ | |
| 883 | 5-$OCF_2H$ | $CH_2CH=CH_2$ | $CH_3$ | $CH_3$ | $CH_3$ | $CH_3$ | |
| 884 | 5-$OCF_2H$ | $CH_2C\equiv CH$ | H | $CH_3$ | $CH_3$ | $CH_3$ | |
| 885 | 5-$OCF_2H$ | 4-Cl—Ph | H | $CH_3$ | $CH_3$ | $CH_3$ | |
| 886 | 5-$OCF_2H$ | 4-F—Ph | H | $CH_3$ | $CH_3$ | $CH_3$ | |
| 887 | 5-Cl | 4-Cl—Ph | $CH_3$ | $CH_3$ | $CH_3$ | $CH_3$ | |
| 888 | 5-Cl | 4-Cl—Ph | $C_2H_5$ | $CH_3$ | $CH_3$ | $CH_3$ | |
| 889 | 5-Cl | 4-F—Ph | $CH_3$ | $CH_3$ | $CH_3$ | $CH_3$ | |
| 890 | 5-Cl | 4-$CF_3$—Ph | $CH_3$ | $CH_3$ | $CH_3$ | $CH_3$ | |
| 891 | 5-F | 4-Cl—Ph | $CH_3$ | $CH_3$ | $CH_3$ | $CH_3$ | |
| 892 | 5-F | 4-F—Ph | $CH_3$ | $CH_3$ | $CH_3$ | $CH_3$ | |
| 893 | 5-$CF_3$ | 4-Cl—Ph | $CH_3$ | $CH_3$ | $CH_3$ | $CH_3$ | |
| 894 | 5-Cl | 4-Cl—Ph | $CH_2CH=CH_2$ | $CH_3$ | $CH_3$ | $CH_3$ | |

TABLE 8

(A=$NR^{10}$)

| Compound No. | $R^1$ | $R^2$ | $R^3$ | $R^4$ | $R^5$ | $R^6$ | $R^{10}$ | Physical properties |
|---|---|---|---|---|---|---|---|---|
| 895 | H | $CH_3$ | $CH_3$ | $CH_3$ | $CH_3$ | $CH_3$ | $CH_3$ | $n_D^{25.0}$ 1.6431 |
| 896 | 5-Cl | $CH_3$ | $CH_3$ | $CH_3$ | $CH_3$ | $CH_3$ | $CH_3$ | |
| 897 | 5-Cl | $C_2H_5$ | $C_2H_5$ | $CH_3$ | $CH_3$ | $CH_3$ | $CH_3$ | |
| 898 | 5-Cl | $CH_3$ | $CH_3$ | $C_2H_5$ | $CH_3$ | $CH_3$ | $CH_3$ | |
| 899 | 5-Cl | $CH_3$ | $CH_3$ | i-$C_3H_7$ | $CH_3$ | $CH_3$ | $CH_3$ | |
| 900 | 5-Cl | $CH_3$ | $CH_3$ | $CF_3$ | $CH_3$ | $CH_3$ | $CH_3$ | |
| 901 | 5-Cl | $CH_3$ | $CH_3$ | $CH_3$ | $CH_3$ | $CH_3$ | $C_2H_5$ | |
| 902 | 5-Cl | 4-Cl—Ph | H | $CH_3$ | $CH_3$ | $CH_3$ | $CH_3$ | |
| 903 | 5-F | 4-Cl—Ph | H | $CH_3$ | $CH_3$ | $CH_3$ | $CH_3$ | |
| 904 | 5-F | 4-F—Ph | H | $CH_3$ | $CH_3$ | $CH_3$ | $CH_3$ | |
| 905 | 5-$OCF_2H$ | 4-Cl—Ph | H | $CH_3$ | $CH_3$ | $CH_3$ | $CH_3$ | |
| 906 | 5-$OCF_2CF_2H$ | 4-Cl—Ph | H | $CH_3$ | $CH_3$ | $CH_3$ | $CH_3$ | |
| 907 | 5-Cl | 4-F—Ph | H | $CH_3$ | $CH_3$ | $CH_3$ | $CH_3$ | |
| 908 | 5-Cl | $CH_3$ | $CH_3$ | $CH_3$ | $CH_3$ | $CH_3$ | $CH_2CF_3$ | |
| 909 | 5-Cl | $CH_3$ | $CH_3$ | $CH_3$ | $CH_3$ | $CH_3$ | $COCH_3$ | |
| 910 | 5-Cl | $CH_3$ | $CH_3$ | $CH_3$ | $C_2H_5$ | $CH_3$ | $CH_3$ | |
| 911 | 5-Cl | $CH_3$ | $CH_3$ | $CH_3$ | n-$C_3H_7$ | $CH_3$ | $CH_3$ | |
| 912 | 5-Cl | $CH_3$ | $CH_3$ | $CH_3$ | $C_2H_5$ | $C_2H_5$ | $CH_3$ | |
| 913 | 5-F | $CH_3$ | $CH_3$ | $CF_3$ | $CH_3$ | $CH_3$ | $CH_3$ | |
| 914 | 5-F | $CH_3$ | $CH_3$ | i-$C_3H_7$ | $CH_3$ | $CH_3$ | $CH_3$ | |

TABLE 9

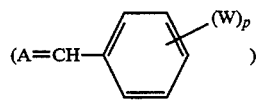

| Compound No. | $R^1$ | $R^2$ | $R^3$ | $R^4$ | $R^5$ | $R^6$ | $(W)_p$ | Physical properties |
|---|---|---|---|---|---|---|---|---|
| 915 | 5-Cl | H | H | $CH_3$ | $CH_3$ | $CH_3$ | 4-F | m.p., 117.2° C. |
| 916 | 5-Cl | H | H | $CH_3$ | $CH_3$ | $CH_3$ | 4-Cl | m.p., 125.1° C. |
| 917 | 5-Cl | H | H | $CH_3$ | $CH_3$ | $CH_3$ | 4-$CF_3$ | |
| 918 | 5-Cl | H | H | $C_2H_5$ | $CH_3$ | $CH_3$ | 4-Cl | |
| 919 | 5-Cl | H | H | i-$C_3H_7$ | $CH_3$ | $CH_3$ | 4-Cl | |
| 920 | 5-Cl | H | H | $CF_3$ | $CH_3$ | $CH_3$ | 4-Cl | |
| 921 | 5-Cl | H | H | $CH_3$ | $CH_3$ | $C_2H_5$ | 4-Cl | |
| 922 | 5-Cl | H | H | $CH_3$ | $CH_3$ | n-$C_3H_7$ | 4-Cl | |
| 923 | 5-Cl | H | H | $CH_3$ | $C_2H_5$ | $C_2H_5$ | 4-Cl | |
| 924 | 5-Cl | H | H | $CH_3$ | $CH_3$ | $CH_3$ | 4-$OCF_3$ | |
| 925 | 5-F | H | H | $CH_3$ | $CH_3$ | $CH_3$ | 4-Cl | |
| 926 | 5-F | H | H | $CH_3$ | $CH_3$ | $CH_3$ | 4-F | m.p., 107.4° C. |
| 927 | 5-F | H | H | $CH_3$ | $CH_3$ | $CH_3$ | 4-$CF_3$ | |
| 928 | 5-$OCF_3$ | H | H | $CH_3$ | $CH_3$ | $CH_3$ | 4-Cl | |
| 929 | 5-$OCF_2H$ | H | H | $CH_3$ | $CH_3$ | $CH_3$ | 4-Cl | |

TABLE 9-continued

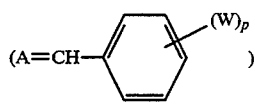

| Compound No. | $R^1$ | $R^2$ | $R^3$ | $R^4$ | $R^5$ | $R^6$ | $(W)_p$ | Physical properties |
|---|---|---|---|---|---|---|---|---|
| 930 | 5-F | H | H | $CF_3$ | $CH_3$ | $CH_3$ | 4-F | |
| 931 | 5-F | H | H | $i-C_3H_7$ | $CH_3$ | $CH_3$ | 4-F | |
| 932 | $5-CF_3$ | H | H | $CH_3$ | $CH_3$ | $CH_3$ | 4-Cl | |
| 933 | $5-CF_3$ | H | H | $CH_3$ | $CH_3$ | $CH_3$ | 4-F | |
| 934 | 5-Br | H | H | $CH_3$ | $CH_3$ | $CH_3$ | 4-Cl | |
| 935 | 5-Br | H | H | $CH_3$ | $CH_3$ | $CH_3$ | 4-F | |
| 936 | $5-CH_3$ | H | H | $CH_3$ | $CH_3$ | $CH_3$ | 4-Cl | |
| 937 | $5-CH_3$ | H | H | $CH_3$ | $CH_3$ | $CH_3$ | 4-F | |

TABLE 10

(A=S)

| Compound No. | $R^1$ | $R^2$ | $R^3$ | $R^4$ | $R^5$ | $R^6$ | Physical properties |
|---|---|---|---|---|---|---|---|
| 938 | 5-Cl | $CH_3$ | H | $CH_3$ | $CH_3$ | $CH_3$ | |
| 939 | 5-Cl | $C_2H_5$ | H | $CH_3$ | $CH_3$ | $CH_3$ | |
| 940 | 5-Cl | $n-C_3H_7$ | H | $CH_3$ | $CH_3$ | $CH_3$ | |
| 941 | 5-Cl | $i-C_3H_7$ | H | $CH_3$ | $CH_3$ | $CH_3$ | |
| 942 | 5-Cl | $CH_3$ | $CH_3$ | $CH_3$ | $CH_3$ | $CH_3$ | $n_D^{23.4}$ 1.6591 |
| 943 | 5-F | $CH_3$ | $CH_3$ | $CH_3$ | $CH_3$ | $CH_3$ | |
| 944 | 5-F | $CH_3$ | $CH_3$ | $C_2H_5$ | $CH_3$ | $CH_3$ | |
| 945 | 5-F | $CH_3$ | $CH_3$ | $i-C_3H_7$ | $CH_3$ | $CH_3$ | |
| 946 | 5-F | $CH_3$ | $CH_3$ | $CF_3$ | $CH_3$ | $CH_3$ | |
| 947 | 5-Cl | $CH_3$ | $CH_3$ | $CF_3$ | $CH_3$ | $CH_3$ | |
| 948 | 5-Cl | $CH_3$ | $CH_3$ | $i-C_3H_7$ | $CH_3$ | $CH_3$ | |
| 949 | 5-Cl | $CH_3$ | $CH_3$ | $CH_3$ | $CH_3$ | $C_2H_5$ | |
| 950 | 5-Cl | $CH_3$ | $CH_3$ | $CH_3$ | $CH_3$ | $n-C_3H_7$ | |
| 951 | 5-Cl | $CH_3$ | $CH_3$ | $CH_3$ | $C_2H_5$ | $C_2H_5$ | |
| 952 | 5-Br | $CH_3$ | $CH_3$ | $CH_3$ | $CH_3$ | $CH_3$ | |
| 953 | $5-OCF_2H$ | $CH_3$ | $CH_3$ | $CH_3$ | $CH_3$ | $CH_3$ | |

TABLE 11

(A=$SCH_2$)

| Compound No. | $R^1$ | $R^2$ | $R^3$ | $R^4$ | $R^5$ | $R^6$ | Physical properties |
|---|---|---|---|---|---|---|---|
| 954 | 5-Cl | Ph | H | $CH_3$ | $CH_3$ | $CH_3$ | |
| 955 | 5-Cl | 4-Cl—Ph | H | $CH_3$ | $CH_3$ | $CH_3$ | m.p., 130.5° C. |
| 956 | 5-Cl | 4-F—Ph | H | $CH_3$ | $CH_3$ | $CH_3$ | m.p., 176.5° C. |
| 957 | 5-Cl | 4-Br—Ph | H | $CH_3$ | $CH_3$ | $CH_3$ | |
| 958 | 5-Cl | 4-Cl—Ph | H | $C_2H_5$ | $CH_3$ | $CH_3$ | |
| 959 | 5-Cl | 4-Cl—Ph | H | $n-C_3H_7$ | $CH_3$ | $CH_3$ | |
| 960 | 5-Cl | 4-Cl—Ph | H | $i-C_3H_7$ | $CH_3$ | $CH_3$ | |
| 961 | 5-Cl | 4-Cl—Ph | H | $CF_3$ | $CH_3$ | $CH_3$ | |
| 962 | 5-Cl | 4-Cl—Ph | H | $CH_3$ | $CH_3$ | $C_2H_5$ | |
| 963 | 5-Cl | 4-Cl—Ph | H | $CH_3$ | $CH_3$ | $n-C_3H_7$ | |
| 964 | 5-Cl | 4-Cl—Ph | H | $CH_3$ | $C_2H_5$ | $C_2H_5$ | |
| 965 | 5-F | 4-Cl—Ph | H | $CH_3$ | $CH_3$ | $CH_3$ | |
| 966 | 5-F | 4-F—Ph | H | $CH_3$ | $CH_3$ | $CH_3$ | |
| 967 | 5-F | 4-Br—Ph | H | $CH_3$ | $CH_3$ | $CH_3$ | |
| 968 | 5-F | 4-Cl—Ph | H | $CF_3$ | $CH_3$ | $CH_3$ | |
| 969 | 5-F | 4-Cl—Ph | H | $i-C_3H_7$ | $CH_3$ | $CH_3$ | |
| 970 | 5-F | 4-F—Ph | H | $CF_3$ | $CH_3$ | $CH_3$ | |
| 971 | 5-F | 4-F—Ph | H | $i-C_3H_7$ | $CH_3$ | $CH_3$ | |
| 972 | 5-F | 4-F—Ph | H | $CH_3$ | $CH_3$ | $C_2H_5$ | |
| 973 | 5-Cl | 4-F—Ph | H | $CF_3$ | $CH_3$ | $CH_3$ | |
| 974 | 5-Cl | 4-F—Ph | H | $i-C_3H_7$ | $CH_3$ | $CH_3$ | |
| 975 | 5-Br | 4-Cl—Ph | H | $CH_3$ | $CH_3$ | $CH_3$ | |
| 976 | 5-Br | 4-F—Ph | H | $CH_3$ | $CH_3$ | $CH_3$ | |
| 977 | 5-Br | 4-Br—Ph | H | $CH_3$ | $CH_3$ | $CH_3$ | |
| 978 | H | 4-Cl—Ph | H | $CH_3$ | $CH_3$ | $CH_3$ | |
| 979 | 5-Cl | 4-Cl—Ph | H | H | $CH_3$ | $CH_3$ | |
| 980 | 5-Cl | 4-F—Ph | H | H | $CH_3$ | $CH_3$ | |
| 981 | 5-Cl | $CH_3$ | $CO_2CH_3$ | H | $CH_3$ | $CH_3$ | |
| 982 | 5-F | $CH_3$ | $CO_2CH_3$ | H | $CH_3$ | $CH_3$ | |

TABLE 12

(A=NR$^{10}$)

| Compound No. | R$^1$ | R$^2$ | R$^3$ | R$^4$ | R$^5$ | R$^6$ | R$^{10}$ | Physical properties |
|---|---|---|---|---|---|---|---|---|
| 983 | 5-Cl | 4-Br—Ph | H | CH$_3$ | CH$_3$ | CH$_3$ | CH$_3$ | |
| 984 | 5-Br | 4-Cl—Ph | H | CH$_3$ | CH$_3$ | CH$_3$ | CH$_3$ | |
| 985 | 5-Br | 4-F—Ph | H | CH$_3$ | CH$_3$ | CH$_3$ | CH$_3$ | |
| 986 | 6-Cl | 4-Cl—Ph | H | CH$_3$ | CH$_3$ | CH$_3$ | CH$_3$ | |
| 987 | 4-Cl | 4-Cl—Ph | H | CH$_3$ | CH$_3$ | CH$_3$ | CH$_3$ | |
| 988 | 6-F | 4-Cl—Ph | H | CH$_3$ | CH$_3$ | CH$_3$ | CH$_3$ | |
| 989 | 4-F | 4-Cl—Ph | H | CH$_3$ | CH$_3$ | CH$_3$ | CH$_3$ | |
| 990 | 5-Cl | CH$_2$CF$_3$ | CH$_2$CF$_3$ | CH$_3$ | CH$_3$ | CH$_3$ | CH$_3$ | |
| 991 | 5-F | CH$_2$CF$_3$ | CH$_2$CF$_3$ | CH$_3$ | CH$_3$ | CH$_3$ | CH$_3$ | |
| 992 | H | CH$_2$CF$_3$ | CH$_2$CF$_3$ | CH$_3$ | CH$_3$ | CH$_3$ | CH$_3$ | |

TABLE 13

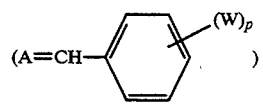

| Compound No. | R$^1$ | R$^2$ | R$^3$ | R$^4$ | R$^5$ | R$^6$ | (W)$_p$ | Physical properties |
|---|---|---|---|---|---|---|---|---|
| 993 mix | 5-F | CH$_3$ | CH$_3$ | CH$_3$ | CH$_3$ | CH$_3$ | 4-F | n$_D^{23.1}$ 1.5890 |
| 994 | 5-F | CH$_3$ | CH$_3$ | CH$_3$ | CH$_3$ | CH$_3$ | 4-Cl | |
| 995 | 5-F | CH$_3$ | CH$_3$ | CH$_3$ | CH$_3$ | CH$_3$ | 4-CF$_3$ | |
| 996 | 5-F | CH$_3$ | CH$_3$ | CH$_3$ | CH$_3$ | CH$_3$ | 4-OCF$_3$ | |
| 997 | 5-F | CH$_3$ | CH$_3$ | CH$_3$ | CH$_3$ | CH$_3$ | 4-OCF$_2$H | |
| 998 | 5-Cl | CH$_3$ | CH$_3$ | CH$_3$ | CH$_3$ | CH$_3$ | 4-F | |
| 999 | 5-Cl | CH$_3$ | CH$_3$ | CH$_3$ | CH$_3$ | CH$_3$ | 4-Cl | |
| 1000 | 5-Cl | CH$_3$ | CH$_3$ | CH$_3$ | CH$_3$ | CH$_3$ | 4-CF$_3$ | |
| 1001 | 5-Cl | CH$_3$ | CH$_3$ | CH$_3$ | CH$_3$ | CH$_3$ | 4-OCF$_3$ | |
| 1002 | 5-Cl | CH$_3$ | CH$_3$ | CH$_3$ | CH$_3$ | CH$_3$ | 4-OCF$_2$H | |
| 1003 | 5-CF$_3$ | CH$_3$ | CH$_3$ | CH$_3$ | CH$_3$ | CH$_3$ | 4-Cl | |
| 1004 | 5-CF$_3$ | CH$_3$ | CH$_3$ | CH$_3$ | CH$_3$ | CH$_3$ | 4-F | |
| 1005 | 5-OCF$_3$ | CH$_3$ | CH$_3$ | CH$_3$ | CH$_3$ | CH$_3$ | 4-Cl | |
| 1006 | 5-OCF$_3$ | CH$_3$ | CH$_3$ | CH$_3$ | CH$_3$ | CH$_3$ | 4-F | |
| 1007 | 5-OCF$_2$H | CH$_3$ | CH$_3$ | CH$_3$ | CH$_3$ | CH$_3$ | 4-Cl | |
| 1008 | 5-OCF$_2$H | CH$_3$ | CH$_3$ | CH$_3$ | CH$_3$ | CH$_3$ | 4-F | |
| 1009 | 5-Cl | C$_2$H$_5$ | C$_2$H$_5$ | CH$_3$ | CH$_3$ | CH$_3$ | 4-Cl | |
| 1010 | 5-OCH$_3$ | H | H | CH$_3$ | CH$_3$ | CH$_3$ | 4-Cl | |
| 1011 | 5-SCH$_3$ | H | H | CH$_3$ | CH$_3$ | CH$_3$ | 4-Cl | |
| 1012 | 6-Cl | H | H | CH$_3$ | CH$_3$ | CH$_3$ | 4-Cl | m.p., 139.0° C. |
| 1013 | 6-Cl | H | H | CH$_3$ | CH$_3$ | CH$_3$ | 4-F | m.p., 159.2° C. |
| 1014 | 6-F | H | H | CH$_3$ | CH$_3$ | CH$_3$ | 4-Cl | |
| 1015 | 6-F | H | H | CH$_3$ | CH$_3$ | CH$_3$ | 4-F | |
| 1016 | 6-CF$_3$ | H | H | CH$_3$ | CH$_3$ | CH$_3$ | 4-Cl | n$_D^{22.5}$ 1.5887 |
| 1017 | 4-F | H | H | CH$_3$ | CH$_3$ | CH$_3$ | 4-F | |
| 1018 | 4-Cl | H | H | CH$_3$ | CH$_3$ | CH$_3$ | 4-Cl | m.p., 132.2° C. |
| 1019 | 4-Cl | H | H | CH$_3$ | CH$_3$ | CH$_3$ | 4-F | m.p., 120.7° C. |
| 1020 | 4-CF$_3$ | H | H | CH$_3$ | CH$_3$ | CH$_3$ | 4-Cl | n$_D^{22.0}$ 1.6119 |
| 1021 | 5-Cl | H | H | CH$_3$ | CH$_3$ | CH$_3$ | 3-Cl | |
| 1022 | 5-Cl | H | H | CH$_3$ | CH$_3$ | CH$_3$ | 3-F | |
| 1023 | 5-Cl | H | H | CH$_3$ | CH$_3$ | CH$_3$ | 2-Cl | |
| 1024 | 5-Cl | H | H | CH$_3$ | CH$_3$ | CH$_3$ | 2-F | |
| 1025 | 5-Cl | H | H | CH$_3$ | CH$_2$CH=CH$_2$ | CH$_3$ | 4-Cl | |
| 1026 | 5-Cl | H | H | CH$_3$ | CH$_2$C CH | CH$_3$ | 4-Cl | |
| 1027 | 5-Cl | H | H | n-C$_3$H$_7$ | CH$_3$ | CH$_3$ | 4-Cl | |
| 1028 | 5-F | H | H | CH$_3$ | C$_2$H$_5$ | CH$_3$ | 4-Cl | |
| 1029 | 5-F | H | H | CH$_3$ | C$_2$H$_5$ | C$_2$H$_5$ | 4-Cl | |
| 1030 | 5-F | H | H | CH$_3$ | n-C$_3$H$_7$ | CH$_3$ | 4-Cl | |
| 1031 | 5-F | H | H | H | CH$_3$ | CH$_3$ | 4-Cl | |
| 1032 | 5-Cl | H | H | H | CH$_3$ | CH$_3$ | 4-Cl | |

TABLE 14

(A=CH$_2$)

| Compound No. | R$^1$ | R$^2$ | R$^3$ | R$^4$ | R$^5$ | R$^6$ | Physical properties |
|---|---|---|---|---|---|---|---|
| 1033 | 5-Cl | 4-Cl—Ph | H | CH$_3$ | CH$_2$CH$_2$OH | C$_2$H$_5$ | oily solid |
| 1034 | 5-Cl | 4-Cl—Ph | H | CH$_3$ | CH$_2$CH$_2$OCH$_3$ | H | |
| 1035 | 5-Cl | 4-Cl—Ph | H | CH$_3$ | CH$_2$CH$_2$CH$_2$OCH$_3$ | H | |
| 1036 | 5-Cl | 4-Cl—Ph | H | CH$_3$ | CH$_2$CH$_2$OCH$_3$ | CH$_2$CH$_2$OCH$_3$ | n$_D^{23.0}$ 1.6127 |
| 1037 | 5-Cl | 4-Cl—Ph | H | CH$_3$ | CH$_2$CH$_2$NHCH$_3$ | CH$_3$ | |
| 1038 | 5-Cl | 4-Cl—Ph | H | CH$_3$ | CH$_2$CH$_2$N(CH$_3$)$_2$ | CH$_3$ | |
| 1039 | 5-Cl | 4-Cl—Ph | H | CH$_3$ | CH$_2$CN | CH$_2$CN | |
| 1040 | 5-Cl | 4-Cl—Ph | H | CH$_3$ | CH$_2$CH$_2$CN | CH$_2$CH$_2$CN | |

TABLE 14-continued (A=CH$_2$)

| Compound No. | R$^1$ | R$^2$ | R$^3$ | R$^4$ | R$^5$ | R$^6$ | Physical properties |
|---|---|---|---|---|---|---|---|
| 1041 | 5-Cl | 4-Cl—Ph | H | CH$_3$ | CH$_2$C CH | CH$_2$C CH | n$_D^{23.5}$ 1.5765 |
| 1042 | 5-Cl | CH$_2$CH$_2$CN | H | CH$_3$ | CH$_3$ | CH$_3$ | |
| 1043 | 5-Cl | CH$_2$CH$_2$CN | CH$_3$ | CH$_3$ | CH$_3$ | CH$_3$ | n$_D^{19.0}$ 1.6094 |
| 1044 | 5-Cl | CH$_2$CH$_2$CN | CH$_2$CH$_3$ | CH$_3$ | CH$_3$ | CH$_3$ | |
| 1045 | 5-Cl | 4-Cl—Ph | H | CH$_3$ | CH$_2$CH$_2$OCH$_3$ | H | |
| 1046 | 5-Cl | 4-Cl—Ph | H | CH$_3$ | CH$_2$CH$_2$CH$_2$OCH$_3$ | H | |
| 1047 | 5-Cl | 4-Cl—Ph | H | CH$_3$ | CH$_2$CH$_2$OCH$_3$ | CH$_3$ | |

TABLE 15

(A=CH$_2$CH$_2$)

| Compound No. | R$^1$ | R$^2$ | R$^3$ | R$^4$ | R$^5$ | R$^6$ | Physical properties |
|---|---|---|---|---|---|---|---|
| 1048 | 5-Cl | 3-Cl—Ph | H | CH$_3$ | CH$_3$ | CH$_3$ | m.p., 103.1° C. |
| 1049 | 5-Cl | 3-F—Ph | H | CH$_3$ | CH$_3$ | CH$_3$ | |
| 1050 | 5-Cl | 3-Br—Ph | H | CH$_3$ | CH$_3$ | CH$_3$ | |
| 1051 | 5-Cl | 4-F—Ph | CH$_3$ | CH$_3$ | CH$_3$ | CH$_3$ | |
| 1052 | 5-Cl | 4-Cl—Ph | CH$_3$ | CH$_3$ | CH$_3$ | CH$_3$ | resinous solid |
| 1053 | 5-Cl | 4-Cl—Ph | H | CH$_2$CH$_3$ | CH$_3$ | CH$_3$ | |
| 1054 | 5-Cl | 4-Cl—Ph | H | i-C$_3$H$_7$ | CH$_3$ | CH$_3$ | |
| 1055 | 5-Cl | 4-Cl—Ph | H | CH$_3$ | C$_2$H$_5$ | CH$_3$ | |
| 1056 | 5-Cl | 4-Cl—Ph | H | CH$_3$ | n-C$_3$H$_7$ | CH$_3$ | |
| 1057 | 5-Cl | 4-Cl—Ph | H | CH$_3$ | C$_2$H$_5$ | C$_2$H$_5$ | |
| 1058 | 6-Cl | 3-Cl—Ph | H | CH$_3$ | CH$_3$ | CH$_3$ | m.p., 133.2° C. |

TABLE 16

(A=CR$^a$R$^b$)

| Compound No. | R$^1$ | R$^2$ | R$^3$ | R$^4$ | R$^5$ | R$^6$ | R$^a$ | R$^b$ | Physical properties |
|---|---|---|---|---|---|---|---|---|---|
| 1059 | H | H | H | CH$_3$ | CH$_3$ | CH$_3$ | CH$_3$ | CH$_3$ | n$_D^{20.0}$ 1.6220 |
| 1060 | 5-Cl | H | H | CH$_3$ | CH$_3$ | CH$_3$ | CH$_3$ | CH$_3$ | |
| 1061 | 5-F | H | H | CH$_3$ | CH$_3$ | CH$_3$ | CH$_3$ | CH$_3$ | |
| 1062 | H | CH$_3$ | CH$_3$ | CH$_3$ | CH$_3$ | CH$_3$ | CH$_3$ | CH$_3$ | n$_D^{23.5}$ 1.5927 |
| 1063 | 5-Cl | CH$_3$ | CH$_3$ | CH$_3$ | CH$_3$ | CH$_3$ | CH$_3$ | CH$_3$ | |
| 1064 | 5-F | CH$_3$ | CH$_3$ | CH$_3$ | CH$_3$ | CH$_3$ | CH$_3$ | CH$_3$ | |
| 1065 | 5-Cl | CH$_3$ | CH$_3$ | CH$_3$ | CH$_3$ | CH$_3$ | CH$_3$ | H | |
| 1066 | 5-Cl | 4-Cl—Ph | H | CH$_3$ | CH$_3$ | CH$_3$ | CH$_3$ | H | |
| 1067 | 5-Cl | 4-F—Ph | H | CH$_3$ | CH$_3$ | CH$_3$ | CH$_3$ | H | |
| 1068 | 5-Cl | 4-Br—Ph | H | CH$_3$ | CH$_3$ | CH$_3$ | CH$_3$ | H | |
| 1069 | 5-F | 4-Cl—Ph | H | CH$_3$ | CH$_3$ | CH$_3$ | CH$_3$ | H | |
| 1070 | 5-F | 4-F—Ph | H | CH$_3$ | CH$_3$ | CH$_3$ | CH$_3$ | H | |
| 1071 | 5-Br | 4-Cl—Ph | H | CH$_3$ | CH$_3$ | CH$_3$ | CH$_3$ | H | |
| 1072 | 5-Br | 4-F—Ph | H | CH$_3$ | CH$_3$ | CH$_3$ | CH$_3$ | H | |
| 1073 | 5-Cl | 4-Cl—Ph | CH$_3$ | CH$_3$ | CH$_3$ | CH$_3$ | CH$_3$ | H | |
| 1074 | 5-Cl | 4-Cl—Ph | H | C$_2$H$_5$ | CH$_3$ | CH$_3$ | CH$_3$ | H | |
| 1075 | 5-Cl | 4-Cl—Ph | H | n-C$_3$H$_7$ | CH$_3$ | CH$_3$ | CH$_3$ | H | |
| 1076 | 5-Cl | 4-Cl—Ph | H | CH$_3$ | C$_2$H$_5$ | CH$_3$ | CH$_3$ | H | |
| 1077 | 5-Cl | 4-Cl—Ph | H | CH$_3$ | n-C$_3$H$_7$ | CH$_3$ | CH$_3$ | H | |
| 1078 | 5-Cl | 4-Cl—Ph | H | CH$_3$ | C$_2$H$_5$ | C$_2$H$_5$ | CH$_3$ | H | |

TABLE 17

(A=CR$^a$R$^b$CH$_2$)

| Compound No. | R$^1$ | R$^2$ | R$^3$ | R$^4$ | R$^5$ | R$^6$ | R$^a$ | R$^b$ | Physical properties |
|---|---|---|---|---|---|---|---|---|---|
| 1079 | H | CH$_3$ | CH$_3$ | CH$_3$ | CH$_3$ | CH$_3$ | CH$_3$ | H | n$_D^{23.5}$ 1.5765 |
| 1080 | 5-Cl | CH$_3$ | CH$_3$ | CH$_3$ | CH$_3$ | CH$_3$ | CH$_3$ | H | |
| 1081 | 5-Cl | 4-Cl—Ph | H | CH$_3$ | CH$_3$ | CH$_3$ | CH$_3$ | H | |
| 1082 | 5-Cl | 4-Cl—Ph | CH$_3$ | CH$_3$ | CH$_3$ | CH$_3$ | CH$_3$ | H | |
| 1083 | 5-Cl | 4-Cl—Ph | H | CH$_3$ | CH$_3$ | CH$_3$ | CH$_3$ | CH$_3$ | |
| 1084 | 5-Cl | 4-Cl—Ph | H | C$_2$H$_5$ | CH$_3$ | CH$_3$ | CH$_3$ | H | |
| 1085 | 5-Cl | 4-Cl—Ph | H | CH$_3$ | C$_2$H$_5$ | CH$_3$ | CH$_3$ | H | |
| 1086 | 5-Cl | 4-Cl—Ph | H | CH$_3$ | n-C$_3$H$_7$ | CH$_3$ | CH$_3$ | H | |
| 1087 | 5-Cl | 4-F—Ph | H | CH$_3$ | CH$_3$ | CH$_3$ | CH$_3$ | H | |

The following will describe production examples for the compounds of the general formula [IX].

Reference Example 1

To a solution of 2-(4-chlorophenyl)-5-fluoro-2,3-dihydro-1H-inden-1-ylidene hydrazone (2.00 g) and triethylamine (0.17 g) in dichloromethane (75 ml) was added dropwise acetylchloride (0.66 g) under ice-cooling, followed by stirring at room temperature for 1 hour. The reaction mixture was diluted with dichloromethane (15 ml), poured into ice-water and extracted.

The organic layer was dried over anhydrous magnesium sulfate and concentrated under reduced pressure. The resulting crystals were subjected to chromatography on silica gel to give the desired compound, 2-(4-chlorophenyl)-5-fluoro-2,3-dihydro-1H-inden-1-yliden-N'-acetylhydrazone (yield, 2.23 g) as white crystals, m.p., 114.2° C.

According to these procedures, the following several compounds of the general formula [IX] can be produced.

5-Chloro-2-phenyl-2,3-dihydro-1H-inden-1-ylidene-N'-trifluoroacetylhydrazone, m.p., 123°–125° C.

5-Chloro-2-phenyl-2,3-dihydro-1H-inden-1-ylidene-N'-chloroacetylhydrazone, m.p., 173°–175° C.

5-Chloro-2,3-dihydro-2,2-dimethyl-1H-inden-1-ylidene-N'-acetylhydrazone, m.p., 147°–148° C.

5-Chloro-2-(4-fluorophenyl)-2,3-dihydro-1H-inden-1-ylidene-N'-acetylhydrazone, m.p., 149.4° C The following will describe production examples for the ketone compounds of the general formula [VIII].

Reference Example 2

1) To a solution of lithium diisopropylamide (LDA) in THF (1 liter), which had been prepared from diisopropylamine (52 g) and a 1.6 M solution of n-butyl lithium in hexane (319 ml), was added dropwise a solution of ethyl 4-chlorophenylacetate (97.3 g) in THF (100 ml) at a temperature of −45° to −40° C. under an atmosphere of nitrogen gas. At the same temperature, the reaction mixture was stirred for 0.5 hours, and methyl iodide (73 g) was added dropwise thereto, followed by allowing the temperature to gradually increase to room temperature. The reaction mixture was poured into ice-water and extracted with ether. The organic layer was washed with water, dried over anhydrous magnesium sulfate, and concentrated under reduced pressure. The resulting residue was distilled under reduced pressure to give ethyl 2-(4-chlorophenyl)propionate (yield, 89.4 g), b.p., 108°–114° C. at 1.0 mmHg.

$^1$H-NMR (CDCl$_3$, TMS) δ(ppm): 7.30 (d, 2H), 7.23 (d, 2H), 4.12 (q, 2H), 3.69 (q, 1H), 1.48 (d, 3H), 1.20 (t, 3H).

2) To a solution of LDA in THF (1 liter), which had been prepared from diisopropylamine (35 g) and a 1.6M solution of n-butyl lithium in hexane (216 ml), was added dropwise a solution of ethyl 2-(4-chlorophenyl)-propionate (70 g) in THF (100 ml) which had been obtained in paragraph 1), at a temperature of −45° to −40° C. under an atmosphere of nitrogen gas. At the same temperature, the reaction mixture was stirred for 0.5 hours, and m-chlorobenzyl chloride (55.7 g) was added dropwise thereto. The mixture was subjected to the same post-treatment as described in paragraph 1), and the residue was dissolved in ethanol (700 ml). To this solution was added dropwise 40% aqueous sodium hydroxide (40 ml), followed by heating under reflux for 5 hours. After cooling to room temperature, the reaction mixture was concentrated under reduced pressure. The resulting residue was added dropwise to 10% aqueous hydrochloric acid under ice-cooling, and extracted several times with dichloromethane. The extract was dried over anhydrous magnesium sulfate, and concentrated under reduced pressure. The resulting crystalline residue was washed with hexane to give 2-(3-chlorobenzyl)-2-(4-chlorophenyl)propionic acid (yield, 93 g) as white crystals, m.p., 154.8° C.

$^1$H-NMR (CDCl$_3$-DMSO-d$_6$, TMS) δ(ppm): 9.7 (m, 1H), 6.6–7.3 (m, 8H), 3.13 (q, 2H), 1.37 (s, 3H).

3) A solution of 2-(3-chlorobenzyl)-2-(4-chlorophenyl)propionic acid (10 g) which had been prepared in paragraph 2), and thionyl chloride (14 g) in hexane (100 ml) was heated under reflux for 5 hours. After cooling to room temperature, the reaction mixture was concentrated under reduced pressure. The resulting residue was dissolved in carbon disulfide (100 ml), and the solution was cooled with ice, to which anhydrous aluminum chloride (4.2 g) was added in three portions at intervals of 15 minutes. After allowing the temperature to gradual increase to room temperature, the reaction mixture was diluted with dichloromethane (100 ml), poured into 20% hydrochloric acid and ice-water, followed by stirring for 2 hours. The organic layer was dried over anhydrous magnesium sulfate, and reduced under reduced pressure. The resulting residue was subjected to chromatography on silica gel to give 5-chloro-2-(4-chlorophenyl)-2-methyl-2,3-dihydro-1H-inden-1-one (yield, 7.2 g) as white crystals, m.p., 92.2° C,.

Reference Example 3

1) To a solution of 5-chloroindanone (10 g) and dimethyl carbonate (6.0 ml) in THF (80 ml) was added a 60% oil dispersion (5.0 g) of sodium hydride at room temperature, followed by heating at reflux for 12 hours. After cooling to room temperature, methyl iodide (5.0 ml) was added thereto, and the mixture was heated again at reflux for 12 hours. The reaction mixture was poured into ice-water and extracted with dichloromethane (300 ml × 3). The extract was dried over anhydrous magnesium sulfate, and concentrated under reduced pressure. The resulting residue was subjected to chromatography on silica gel to give methyl 5-chloro-2,3-dihydro-2-mehtyl-1-oxo-1H-indene-2-carboxylate (yield, 5.3 g).

$^1$H-NMR (CDCl$_3$, TMS) δ(ppm): 1.52 (s, 3H), 2.96 (d, 1H), 3.68 (s, 3H), 3.69 (d, 1H), 7.40 (d, 1H), 7.47 (s, 1H), 7.71 (d, 1H).

2) To a solution of the methyl 5-chloro-2,3-dihydro-2-methyl-1-oxo-1H-indene-2-carboxylate (1.5 g) and molecular sieve 4A in xylene (25 ml) was added p-toluenesulfonic acid monohydrate (0.05 g), followed by heating at reflux for 50 hours. The reaction mixture was concentrated under reduced pressure and subjected to chromatography on silica gel to give methyl 5-chloro-2,3-dihydro-2-methyl-1-acetylhydrazine-1H-indene-2-carboxylate (yield, 0.27 g).

$^1$H-NMR (CDCl$_3$, TMS) δ(ppm): 1.53 (d,1H), 1.65 (s, 3H), 1.71 (d, 1H), 2.35 (s, 3H), 3.80 (s, 3H), 7.29 (m, 2H), 7.60 (d, 1H).

Reference Example 4

1) m-Chlorothiophenol (11.65 g) was added to 33% aqueous solution (50 ml) of sodium hydroxide and disloved therein by heating to 100° C. Then, chloroacetic acid (15.0 g) was added dropwise thereto and the reaction was allowed to proceed at 100° C. After allowing to stand for cooling to room temperature, diluted sulfuric acid was added thereto, followed by extracted three times with diethyl ether (150 ml, 100 ml and 50 ml). The combined ether layer was extracted with 5% aqueous sodium carbonate (200 ml). The combined alkaline aqueous layer was made strongly acidic by addition of concentrated sulfuric acid, thereby obtaining m-chlorothiophenoxyacetic acid (yield, 15.3 g), m.p., 75.7° C.

2) To a solution of m-chlorothiophenoxyacetic acid (5.00 g, 24.7 mmol) in chlorobenzene (25 ml) was added phosphorous trichloride (2.90 ml) at room temperature, and the reaction was allowed to proceed with vigorous stirring at 100° C. for 2 hours. After cooling to room temperature, anhydrous aluminum chloride (3.70 g, 27.7 mmol) was added thereto, and the reaction was allowed to proceed at room temperature for 30 minutes, followed by stirring at 100° C. for 1.5 hours. After cooling to room temperature, the reaction mixture was poured into ice-water and separated with a separatory funnel. The aqueous layer was extracted with toluene (150 ml×2). The combined organic layer was dried over anhydrous magnesium sulfate and concentrated under reduced pressure. The resulting residue was subjected to chromatography on silica gel to give 6-chloro-2,3-dihydro-benzothiofuran-3-one (2.83 g, 15.3 mmol; yield, 62%), m.p., 123.8° C.

3) A solution of 6-chloro-2,3-dihydro-benzothiofuran-3-one (0.75 g), potassium tert-butoxide (3.0 g) an iodomethane (5.0 ml) in benzene (10 ml) was heated at reflux for 4 hours. After cooling to room temperature, the reaction mixture was poured into ice-water and extracted with toluene (100 ml). The organic layer was washed with water, dried over anhydrous magnesium sulfate, and concentrated under reduced pressure. The resulting residue was subjected to chromatography on silica gel to give 6-chloro-2,3-dihydro-2,2-dimethylbenzothiofuran-3-one (yield, 0.64 g)

$^1$H-NMR (CDCl$_3$, TMS) δ(ppm): 1.56 (s, 6H), 6.57 (d, 1H), 6.83 (d, 1H), 7.37 (t, 1H).

Reference Example 5

1) Metal sodium (1.5 g) was gradually added to ethanol (50 ml) at room temperature, followed by stirring for 5 minutes, and diethyl carbonate (8.9 ml, 73 mmol) was added thereto at room temperature. Further, a solution of ethyl 4-chlorophenylacetate (10 g) in ethanol (10 ml) was added dropwise thereto with stirring, and the stirring was continued for 2 hours. The reaction mixture was concentreated, and diethyl ether (150 ml) and 10% aqueous acetic acid (150 ml) were added to the residue for extraction. The aqueous layer was further washed with diethyl ether (50 ml). The combined organic layer was dried over magnesium sulfate and concentrated under reduced pressure. To the resulting residue were added water (25 ml) and 37% aqueous formaldehyde (8 ml) at room temperature, followed by vigorous stirring at room temperature. After addition of an aqueous solution (36 ml) of potassium carbonate (6.5 g) over 5 minutes, the mixture reaction was stirred for 4 hours and extracted with diethyl ether (100 ml×2). The extract was dried over anhydrous magnesium sulfate and concentrated under reduced pressure to give a crude product of ethyl 4-chlorophenyl-α-methyleneacetate (yield, 10 g).

2) A solution of the ethyl 4-chlorophenyl-α-methyleneacetate (4.2 g), m-chlorothiophenol (2.9 g) and sodium ethoxide (0.05 g) in ethanol (20 ml) was stirred at room temperature for 12 hours. The reaction mixture was concentrated under reduced pressure, followed by addition of water (150 ml) to the residue, and the mixture was extracted with ether (150 ml). The extract was washed two times with 15% aqueous sodium hydroxide, dried over anhydrous magnesium sulfate, and concentrated under reduced pressure. To the resulting residue were added 88% formic acid (20 ml) and methanesulfonic acid (2.1 ml), followed by heating at reflux for 8 hours. After cooling to room temperature, the mixture was poured into water (100 ml) and extracted with dichloromethane (150 ml). The aqueous layer was further washed with dichloromethane (50 ml), and the combined organic layer was dried over anhydrous magnesium sulfate and concentrated. The resulting residue was subjected to chromatography on silica gel to give 4-chlorophenyl-α-[(3-chlorophenyl)thiomethyl]-acetic acid (yield, 5.3 g), n$_D^{23.6}$, 1.5627

3) A solution of 4-chlorophenyl-α-[(3-chlorophenyl)-thiomethyl]acetic acid (2.0 g), thionyl chloride (5 ml) and N,N-dimethylformamide (one drop) in hexane (10 ml) was heated at reflux for 1 hour. The reaction mixture was concentrated under reduced pressure. To the resulting residue, dichloroethane (13 ml) was added under a stream of nitrogen gas and anhydrous aluminum chloride (1.0 g) was added in small portions at a temperature below 0° C. The reaction was allowed to proceed at 0° C. for 1 hour, and the reaction mixture was poured into ice-water and extracted with methylene chloride (100 ml, 50 ml×2). The extract was dried over anhydrous magnesium sulfate and concentrated to give 7-chloro-3-(4-chlorophenyl)-2,3-dihydro-4H-1-benzothiopyran-4-one.

Reference Example 6

1) To a solution of ethyl 4-chlorosalicylate (9.45 g) and potassium carbonate (10.3 g) in N,N-dimethylformamide (100 ml) was added methyl 2-chloropropionate (6.9 g), followed by stirring overnight at room temperature. The reaction mixture was poured into water (200 ml) and extracted with ether (200 ml×2). The extract was dried over anhydrous magnesium sulfate and concentrated under reduced pressure. The resulting residue was subjected to chromatography on silica gel to give ethyl 4-chloro-2-(1(methoxycarbonyl)ethoxy)benzoate (yield, 8.4 g).

$^1$H-NMR (CDCl$_3$, TMS) δ(ppm): 7.65 (d, 1H), 7.26 (dd, 1H), 6.70 (d, 1H), 4.68 (q, 1H), 4.27 (q, 2H), 3.66 (s, 3H), 1.55 (d, 3H), 1.30 (t, 3H).

2) A solution of ethyl 4-chloro-2-(1-(methoxycarbonyl)ethoxy)benzoate (7.3 g) and 60% oil dispersion (1.5 g) of sodium hydride in tetrahydrofuran (70 ml) was heated at reflux for 30 minutes, and slowly cooled to room temperature. The reaction mixture was poured into ice-aqueous ammonium chloride and extracted with ether. The extract was dried over anhydrous magnesium sulfate and concentrated under reduced pressure. The resulting residue was subjected to chromatography on silica gel to give 6-chloro-2-methyl-3(2H)-benzofuranone (yield, 1.8 g).

$^1$H-NMR (CDCl$_3$, TMS) δ(ppm): 7.42 (d, 1H), 6.75–7.05 (m, 2H), 4.52 (q, 1H), 1.35 (d, 3H).

Reference Example 7

1) To a solution of N-(2-carboxyphenyl)glycine (25 g) in acetic anhydride (50 ml) was added sodium acetate (4.8 g), followed by heating at reflux for 1 hour. The mixture was concentrated under reduced pressure, poured into ice-water, and extracted with ethyl acetate. The extract was dried over anhydrous magnesium sulfate and concentrated under reduced pressure. The resulting residue was subjected to chromatography on silica gel to give N,O-diacetylindoxyl (yield, 3.6 g).

$^1$H-NMR (CDCl$_3$, TMS) δ(ppm): 8.50 (m, 1H), 7.20–7.70 (m, 3H), 2.51 (s, 3H), 2.30 (s, 3H).

2) To a solution of N,O-diacetylindoxyl (3.6 g) in ethanol (20 ml) was added a solution of sodium sulfite (3.6 g) in water (10 ml), followed by heating at reflux for 1 hour. After the solvent (about 10 ml) was distilled off under reduced pressure, the residue was poured into ice-water and extracted with ethyl acetate. The extract was dried over anhydrous magnesium sulfate and concentrated under reduced pressure. The resulting residue was subjected to chromatography on silica gel to give N-acetylindoxyl (1.8 g).

$^1$H-NMR (CDCl$_3$, TMS) δ(ppm): 8.45 (br d, 1H), 7.01–7.75 (m, 3H), 4.24 (s, 2H), 2.30 (s, 3H).

3) In the same manner as described in paragraph 3) of Reference Example 4, N-acetyl-2,2-dimethylindoxyl (yield, 1.1 g) was obtained using N-acetylindoxyl (1.8 g).

$^1$H-NMR (CDCl$_3$, TMS) δ(ppm): 7.0–8.15 (m, 4H), 2.49 (s, 3H), 1.60 (s, 6H).

4) To a solution of N-acetyl-2,2-dimethylindoxyl (1.1 g) in methanol (5 ml) was added a solution of sodium hydroxide (0.25 g) in water (5 ml), followed by heating at reflux for 1 hour. After cooling to room temperature, the mixture was poured into ice-water and extracted with ethyl acetate. The extract was dried over anhydrous magnesium sulfate and concentrated under reduced pressure. The resulting residue was subjected to chromatography on silica gel to give 2,2-dimethylindoxyl (0.75 g).

$^1$H-NMR (CDCl$_3$, TMS) δ(ppm): 7.36–7.62 (m, 2H), 6.58–6.80 (m, 2H), 4.81 (m, 1H), 1.31 (s, 6H).

5) To a solution of sodium hydride (0.2 g) in N,N-dimethylformamide (5 ml) was added dropwise a solution of 2,2-dimethylindoxyl (0.75 g) in N,N-dimethylformamide (1 ml) under ice-cooling. The mixture was stirred at the same temperature for 5 minutes and then at room temperature for 15 minutes. At room temperature, methyl iodide (0.5 g) was added dropwise thereto, and after stirring for 2 hours, the mixture was poured into ice-water and extracted with ethyl acetate. The extract was dried over anhydrous magnesium sulfate and concentrated under reduced pressure. The resulting residue was subjected to chromatography on silica gel to give 2,2,N-trimethylindoxyl (yield, 0.7 g).

$^1$H-NMR (CDCl$_3$, TMS) δ(ppm): 7.0–7.5 (m, 2H), 6.35–6.70 (m, 2H), 2.75 (s, 3H), 1.06 (s, 6H).

The following will describe formulation examples for the compounds of the present invention where parts are all by weight and the compounds are designated by the corresponding compound numbers as shown in Tables 1 to 17.

Formulation Example 1 (Emulsifiable concentrate)

Any one of compounds Nos. 1 to 1087 (10 parts) is dissolved in xylene (35 parts) and dimethylformamide (35 parts), to which polyoxyethylene styrylphenyl ether (14 parts) and calcium dodecylbenzenesulfonate (6 parts) are added, and the resulting mixture is well stirred to give an 10% emulsifiable concentrate.

Formulation Example 2 (Wettable powder)

Any one of compounds Nos. 1 to 1087 (20 parts) is added to a mixture of sodium laurylsulfate (4 parts), calcium ligninsulfate (2 parts), fine powders of synthetic hydrous silica (20 parts) and diatomaceous earth (54 parts), and the resulting mixture is stirred in a mixer to give a 20% wettable powder.

Formulation Example 3 (Granules)

To any one of compounds Nos. 1 to 1087 (5 parts) are added synthetic hydrous silica (5 parts), sodium dodecylbenzenesulfonate (5 parts), bentonite (30 parts) and clay (55 parts), and the resulting mixture is well stirred. This mixture is then kneaded with a suitable amount of water, and granulated in a granulator and air-dried to give 5% granules.

Formulation Example 4 (Dusts)

Any one of compounds Nos. 1 to 1087 (1 part) is dissolved in a suitable amount of acetone, to which fine powders of synthetic hydrous silica (5 parts), PAP (0.3 parts) and clay (93.7 parts) are added, and the resulting mixture is stirred in a mixer, followed by evaporation of acetone to give 1% dusts.

Formulation Example 5 (Flowable concentrate)

Any one of compounds Nos. 1 to 1087 (20 parts) and sorbitan trioleate (1.5 parts) are mixed with an aqueous solution (28.5 parts) containing polyvinyl alcohol (2 parts), and the resulting mixture is pulverized in a sand mill (until the particle size thereof becomes not greater than 3 μm). To this mixture is added an aqueous solution (40 parts) containing xanthane gum (0.05 parts) and aluminum magnesium silicate (0.1 parts), followed by addition of propylene glycol (10 parts). The mixture is stirred to give a 20 % flowable concentrate in water.

Formulation Example 6 (Oil spray)

Any one of compounds Nos. 1 to 1087 (0.1 parts) is dissolved in xylene (0.1 parts) and trichloroethane (5 parts), and the resulting solution is mixed with deodorized kerosene (89.9 parts) to give a 0.1% oil spray.

Formulation Example 7 (Oil-based aerosol)

Any one of compounds Nos. 1 to 1087 (0.1 parts), tetramethrin (0.2 parts), d-phenothrin (0.1 parts), trichloroethane (10 parts) and deodorized kerosene (59.6 parts) are mixed to form a solution, which is then filled in an aerosol container. After the container is provided with a valve, a propellant (liquefied petroleum gas; 30 parts) is filled through the valve under compression to give an oil-based aerosol.

Formulation Example 8 (Water-based aerosol)

A solution of any one of compounds Nos. 1 to 1087 (0.2 parts), d-allethrin (0.2 parts), d-phenothrin (0.2 parts), xylene (5 parts), deodorized kerosene (3.4 parts) and an emulsifier (registered trade name, "ATMOS 300", Atlas Chemical Co., Ltd.; 1 part), is filled, together with pure water (50 parts), in an aerosol container. After the container is provided with a valve, a propellant (liquefied petroleum gas; 40 parts) is filled through the valve under compression to give a water-based aerosol.

Formulation Example 9 (Mosquito coil)

To any one of compounds Nos. 1 to 1087 (0.3 g) is added d-allethrin (0.3 g), and the resulting mixture is dissolved in acetone (20 ml). The solution is uniformly mixed with a carrier for mosquito coils (i.e., a mixture of Tabu power, rice bran powder and wood powder in a ratio of 4:3:3;99.4 g). The mixture is well kneaded with water (120 ml) and formed into a coil, followed by drying to give a mosquito coil.

Formulation Example 10 (Electric mosquito mat)

Any one of compounds Nos. 1 to 1087 (0.4 g), d-allethrin (0.4 g) and piperonyl butoxide (0.4 g) are dissolved in acetone to form a solution (10 ml). This solution (0.5 ml) is uniformly incorporated in a base for electric mosquito mats (i.e., a plate-shaped material composed of cotton linters and pulp as a fibril mixture; size,.2.5 cm x 1.5 cm×0.3 cm) to give an electric mosquito mat.

Formulation Example 11 (Fumigant)

Any one of Compounds Nos. 1 to 1087 (100 mg) is dissolved in an appropriate amount of acetone, and the resultant solution is impregnated into a porous ceramic plate (4.0×4.0×1.2 cm) to give a fumigant.

Formulation Example 12 (Poison bait)

Any one of compounds Nos. 1 to 1087 (10 mg) is dissolved in acetone (0.5 ml), and the solution is uniformly mixed with feed powder for animals (trade name, solid feed powder CE-2 for breeding and propagation, Nihon Kurea K.K.; 5 g), followed by removal of acetone by air-drying to give a 0.5% poison bait.

The following will describe test examples showing that the compounds of the present invention are useful as an active ingredient of insecticides and/or acaricides, where the compounds are designated by the corresponding compound numbers as shown in Tables 1 to 17.

Test Example 1 (Insecticidal activity against tabacco cutworm)

On the bottom of a polyethylene cup of 9 cm in diameter was placed a piece of filter paper having the same size as the bottom size. An emulsifiable concentrate prepared from any one of the test compounds according to Formulation Example 1 was diluted with water into a concentration of 500 ppm, and the dilution (2 ml) was incorporated in an artificial diet for tabacco cutworm (13 g). The artificial diet was placed on the filter paper, and the cup was inoculated with ten 4-instar larvae of tabacco cutworm (*Spodoptera litura*). After six days, it was examined whether the larvae were still alive or dead, and mortality (%) of the larvae was determined. The results are shown in Table 18.

TABLE 18

| Test compound | Mortality (%) |
| --- | --- |
| 1 | 100 |
| 8 | 100 |
| 9 | 100 |
| 10 | 100 |
| 12 | 100 |
| 14 | 100 |
| 26 | 100 |
| 30 | 100 |
| 45 | 100 |
| 46 | 100 |
| 60 | 100 |
| 64 | 100 |
| 89 | 100 |
| 91 | 100 |
| 95 | 100 |
| 132 | 100 |
| 145 | 100 |
| 146 | 100 |
| 270a | 100 |
| 270b | 100 |
| 271a | 100 |
| 271b | 100 |
| 318 | 100 |
| 322 | 100 |
| 326 | 100 |
| 330 | 100 |
| 346 | 100 |
| 347 | 100 |
| 348 | 100 |
| 372 | 100 |
| 441 | 100 |

TABLE 18-continued

| Test compound | Mortality (%) |
| --- | --- |
| 436 | 100 |
| 438 | 100 |
| 439 | 100 |
| 447 | 100 |
| 448 | 100 |
| 449 | 100 |
| 450 | 100 |
| 451 | 100 |
| 479 | 100 |
| 480 | 100 |
| 481 | 100 |
| 482 | 100 |
| 487 | 100 |
| 506 | 100 |
| 551 mix | 100 |
| 552 | 100 |
| 553 | 100 |
| 555 | 100 |
| 560 mix | 100 |
| 607 | 100 |
| 608 | 100 |
| 780 | 100 |
| 783 | 100 |
| 785 | 100 |
| 853 | 100 |
| 856a | 100 |
| 856b | 100 |
| 857a | 100 |
| 857b | 100 |
| 858a | 100 |
| 858b | 100 |
| 860 | 100 |
| 867 | 100 |
| 868 | 100 |
| 926 | 100 |
| 955 | 100 |
| 993 mix | 100 |
| 1018 | 100 |
| 1036 | 100 |
| 1041 | 100 |
| 1043 | 100 |
| 1048 | 100 |
| 1052 | 100 |
| 1079 | 100 |
| Untreated | 0 |

Test example 2 (Ovicidal and larvicidal activity against diamondback moth)

Several sprouted seeds of radish on the fifth to sixth day after seeding were put into a gauge in which 1- to 3-days adults of diamondback moth (*Plutella xylostella*) had been left. At the time when 15 to 20 eggs of diamondback moth were laid on each of the sprouted seeds, the test plants were removed from the gauge. An emulsifiable concentrate prepared from any one of the test compounds according to Formulation Example 1 was diluted with water into a concentration of 50 ppm. In the dilution, two sprouted seeds of radish with laid eggs and two sprouted seeds of radish without laid eggs were immersed for 30 seconds, followed by air-drying, and put into a polyethylene cup of 5.5 cm in diameter. After 6 days, mortality of the eggs or larvae hatched from the eggs was determined on the following criteria:
A: 100%;
B: from 90% inclusive to 100% inclusive; and
C: less than 90%.
The results are shown in Table 19.

TABLE 19

| Test compound | Egg-mortality |
| --- | --- |
| 1 | A |
| 8 | A |
| 9 | A |

TABLE 19-continued

| Test compound | Egg-mortality |
| --- | --- |
| 10 | A |
| 12 | A |
| 14 | A |
| 26 | A |
| 30 | A |
| 45 | A |
| 46 | A |
| 60 | A |
| 64 | A |
| 89 | A |
| 91 | A |
| 95 | A |
| 132 | A |
| 145 | A |
| 270a | A |
| 270b | A |
| 271a | A |
| 271b | A |
| 322 | A |
| 326 | A |
| 330 | A |
| 347 | A |
| 348 | A |
| 436 | A |
| 437 | A |
| 438 | A |
| 439 | A |
| 441 | A |
| 447 | A |
| 448 | A |
| 449 | A |
| 450 | A |
| 451 | A |
| 481 | A |
| 482 | A |
| 506 | A |
| 552 | A |
| 553 | A |
| 608 | A |
| 780 | A |
| 783 | A |
| 785 | A |
| 856a | A |
| 856b | A |
| 857b | A |
| 1048 | A |
| Untreated | C |

Test Example 3 (Insecticidal activity against common mosquito)

An emulsifiable concentrate prepared from any one of the test compounds according to Formulation Example 1 was diluted with water. The dilution (0.7 ml) was added to ion-exchanged water (100 ml) to make an active ingredient concentration of 3.5 ppm, which was then inoculated with Twenty final-instar larvae of common mosquito (*Culex pipiens pallens*). After eight days, the inhibition of eclosion was determined on the following criteria:

A: not less than 90%;
B: from 80% inclusive to 90% exclusive; and
C: less than 80%.

The results are shown in Table 20.

TABLE 20

| Test compound | Inhibition |
| --- | --- |
| 1 | A |
| 4 | A |
| 6 | A |
| 8 | A |
| 9 | A |
| 10 | A |
| 12 | A |
| 14 | A |
| 26 | A |
| 30 | A |
| 45 | A |
| 46 | A |
| 60 | A |
| 64 | A |
| 89 | A |
| 91 | A |
| 92 | A |
| 95 | A |
| 132 | A |
| 145 | A |
| 146 | A |
| 263 | A |
| 270a | A |
| 270b | A |
| 271a | A |
| 271b | A |
| 318 | A |
| 322 | A |
| 326 | A |
| 330 | A |
| 340 | A |
| 347 | A |
| 372 | A |
| 436 | A |
| 438 | A |
| 439 | A |
| 441 | A |
| 448 | A |
| 449 | A |
| 450 | A |
| 451 | A |
| 479 | A |
| 480 | A |
| 481 | A |
| 482 | A |
| 487 | A |
| 505 | A |
| 506 | A |
| 553 | A |
| 555 | A |
| 560 mix | A |
| 608 | A |
| 780 | A |
| 783 | A |
| 785 | A |
| 856a | A |
| 856b | A |
| 857b | A |
| 859 | A |
| 860 | A |
| 879 | A |
| 955 | A |
| 993 mix | A |
| 1041 | A |
| 1048 | A |
| 1052 | A |
| 1062 | A |
| 1079 | A |
| Untreated | C |

Test Example 4 (Insecticidal activity against southern corn rootworm)

On the bottom of a polyethylene cup of 5.5 cm in diameter was placed a piece of filter paper having the same size as the bottom size. An emulsifiable concentrate prepared from any one of the test compounds according to Formulation Example 1 was diluted with water into a concentration of 50 ppm, and the dilution (1 ml) was dripped on the filter paper. A sprouted seed of corn was put into the cup as a bait. About 30 eggs of southern corn rootworm were also put into the cup, and then sealed. After eight days, it was examined whether larvae hatched from the eggs were still alive or dead, and mortality (%) of the larvae was determined. The results are shown in Table 21.

TABLE 21

| Test compound | Mortality (%) |
|---|---|
| 1 | 100 |
| 89 | 100 |
| 95 | 100 |
| 132 | 100 |
| 271b | 100 |
| 322 | 100 |
| 447 | 100 |
| 448 | 100 |
| 481 | 100 |
| 482 | 100 |
| 485 | 100 |
| 506 | 100 |
| 552 | 100 |
| 553 | 100 |
| 555 | 100 |
| 560 | 100 |
| 867 | 100 |
| 993 mix | 100 |
| 1059 | 100 |
| 1062 | 100 |
| 1079 | 100 |
| Untreated | 0 |

Test Example 5 (Insecticidal activity against *Heliothis virescens*)

An emulsifiable concentrate prepared from any one of the test compounds according to Formulation Example 1 was diluted with water into a concentration of 50 ppm. The dilution (400 μl) was incorporated into an artificial diet for *H. virescens* (2.0 g) which had been prepared in a polyethylene cup of 5.5 cm in diameter. A 3-instar larva of *H. virescens* was put into the cup. Ten larvae were used for each of the test compounds. After 6 days, it was examined whether the larvae were still alive or dead, and mortality (%) of the larvae was determined. The results are shown in Table 22.

TABLE 22

| Test compound | Concentration (ppm) | Mortality (%) |
|---|---|---|
| 8 | 50 | 100 |
| 60 | 50 | 100 |
| 64 | 50 | 100 |
| 95 | 50 | 100 |
| 270a | 50 | 100 |
| 447 | 50 | 100 |
| 482 | 50 | 100 |
| Untreated | — | 0 |

Test Example 6 (Acaricidal activity against carmine spider mite)

A potted bush bean (*Phaseolus vulgaris*) of first-leaf stage on the seventh day after seeding was inoculated with ten adults of female carmine spider mite (*Tetranychus cinnabarinus*) per leaf, and placed in a thermostatic room at 25° C. After six days, an emulsifiable concentrate prepared from any one of the test compounds according to Formulation Example 1 was diluted with water into an active ingredient concentration of 500 ppm. The dilution was sprayed on the potted test plants on a turntable at a volume of 15 ml per pot, and simultaneously injected into the soil at a volume of 2 ml per pot. After eight days, the respective test plants were examined for the degree of damage caused by the spider mites on the following criteria:

—: almost no damage;
+: small damage; and
++: similar damage to that of untreated test plants.
The results are shown in Table 23.

TABLE 23

| Test compound | Effect |
|---|---|
| 271b | — |
| 340 | — |
| 553 | — |
| 859 | — |
| 860 | — |
| 878 | — |
| 879 | — |
| Untreated | ++ |

Test Example 7 (Insecticidal activity against *Nilaparvata lugens*)

On the bottom of a polyethylene cup of 5.5 cm in diameter was placed a piece of filter paper having the same size as the bottom size and ion-exchanged water was dropwise added thereto. An emulsifiable concentrate prepared from any one of the test compounds according to Formulation Example 1 was 200-fold diluted with water into a concentration of 500 ppm, and a stem of rice plant having a length of about 5 cm was immersed in this dilution for 1 minute. After air-drying, the stem of rice plant was put into the cup, which was then inoculated with thirty to forty larvae of brown rice planthopper (*Nilaparvata lugens*). After six days, it was examined whether the larvae were still alive or dead, and mortality of the larvae was determined on the following criteria:

A: more than 90%;
B: from 80% inclusive to 90% inclusive; and
C: less than 80%.

The results are shown in Table 24.

TABLE 24

| Test compound | Effect |
|---|---|
| 95 | A |
| 863 | A |
| 895 | A |
| Untreated | C |

What is claimed is:
1. A hydrazone derivative of the general formula [I]:

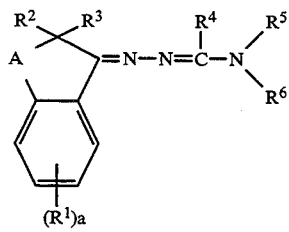

wherein $R^1$ is $R^7$, halogen, cyano, nitro, azide, $OR^7$, $S(O)_nR^7$, $NR^7R^8$, $C(O)R^7$, $CO_2R^7$, $C(O)NR^7R^8$, $OC(O)R^7$, $OCO_2R^7$, $OC(O)NR^7R^8$, $NR^8C(O)R^7$, $NR^8C(O)NR^7R^8$, $OSO_2R^7$ or $NR^8SO_2R^7$; or when a is equal to 2 the two $R^1$ groups are combined to form a 5- or 6-membered ring from $OCH_2O$, $OCH_2CH_2O$ or $CH_2CH_2O$, each of which may be optionally substituted with halogen or methyl;

$R^2$ is hydrogen, $C_1$-$C_6$ alkyl, $C_1$-$C_6$ haloalkyl, $C_3$-$C_6$ cycloalkyl, $C_3$-$C_6$ cycloalkyl($C_1$-$C_4$)alkyl, $C_2$-$C_6$ alkenyl, $C_2$-$C_6$ haloalkenyl, $C_2$-$C_6$ alkynyl, $C_2$-$C_6$ haloalkynyl, $C_1$–$C_6$ alkoxy($C_1$–$C_4$)alkyl, $C_1$–$C_6$ alkylthio($C_1$–$C_4$)alkyl, $C_2$–$C_6$ cyanoalkyl, $C_1$–$C_6$ alkoxycarbonyl($C_1$–$C_4$)alkyl, $OR^7$, $S(O)R^7 NR^7R^8$, cyano $CO_2R^7$, $C(O)R^7$, $C(O)NR^7R^8$, $C(S)NR^7R^8$, $C(S)R^7$, $C(S)SR^7$,

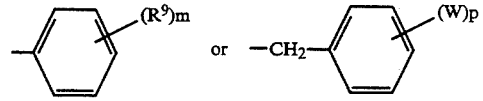

or $C_3$–$C_7$ cycloalkyl optionally substituted with halogen, methyl or trifluoromethyl;

$R^3$ is hydrogen, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ haloalkynyl, $C_1$–$C_6$ alkoxy($C_1$–$C_4$)alkyl, $C_1$–$C_6$ alkylthio($C_1$–$C_4$)alkyl, $C_2$–$C_6$ cyanoalkyl,

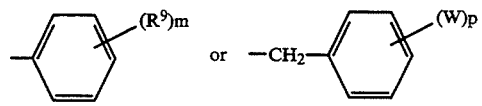

or $C_1$–$C_5$ alkylene optionally substituted with halogen or methyl, with the proviso that the $R^2$ and $R^3$ groups are combined at both ends to form a 3- to 6-membered ring containing 0 to 2 oxygen or sulfur atoms in the ring;

$R^4$ is hydrogen, $C_1$–$C_6$ alkyl or $C_1$–$C_6$ haloalkyl;

$R^5$ is $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ haloalkynyl, $C_1$–$C_6$ alkoxy($C_1$–$C_4$)alkyl, $C_1$–$C_6$ alkylthio($C_1$–$C_4$)alkyl, $C_1$–$C_6$ haloalkoxy($C_1$–$C_4$)alkyl, $C_1$–$C_6$ haloalkylthio($C_1$–$C_4$)alkyl, $C_2$–$C_6$ cyanoalkyl, $C_2$–$C_6$ hydroxyalkyl, $C_1$–$C_4$ alkylamino($C_1$–$C_4$)alkyl, di($C_1$–$C_4$)alkylamino($C_1$–$C_4$)alkyl, $C_1$–$C_6$ alkylcarbonyl, $C_1$–$C_6$ haloalkylcarbonyl or

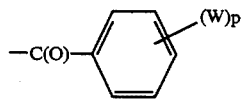

$R^6$ is hydrogen, $C_1$–$C_6$ alkyl, $C_2$–$C_6$ haloalkyl, $C_2$–$C_6$ alkenyl, $C_1$–$C_6$ alkoxy($C_1$–$C_4$)alkyl, $C_2$–$C_6$ cyanoalkyl or $C_2$–$C_6$ alkynyl; or $C_2$–$C_5$ alkylene optionally substituted with halogen or methyl, with the proviso that the $R^5$ and $R^6$ groups are combined at both ends to form a 3- to 6-membered ring containing 0 to 2 oxygen or sulfur atoms in the ring;

$R^7$ is hydrogen, $C_1$–$C_6$ alkyl, $C_1$–$C_6$ haloalkyl, $C_3$–$C_6$ cycloalkyl($C_1$–$C_4$)alkyl, $C_3$–$C_6$ halocycloalkyl($C_1$–$C_4$)alkyl, $C_2$–$C_6$ alkenyl, $C_2$–$C_6$ haloalkenyl, $C_2$–$C_6$ alkynyl, $C_2$–$C_6$ haloalkynyl, $C_1$–$C_6$ alkoxy($C_1$–$C_4$)alkyl, $C_1$–$C_6$ alkylthio($C_1$–$C_4$)alkyl, $C_1$–$C_6$ nitroalkyl, $C_2$–$C_6$ cyanoalkyl, $C_1$–$C_6$ alkoxycarbonyl($C_1$–$C_4$)alkyl, $C_3$–$C_6$ cycloalkyl, $C_3$–$C_6$ halocycloalkyl,

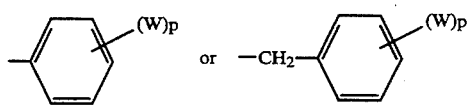

$R^8$ is hydrogen, $C_1$–$C_4$ alkyl, $C_2$–$C_6$ alkenyl or $C_2$–$C_6$ alkynyl; or $C_2$–$C_5$ alkylene optionally substituted with halogen or methyl, with the proviso that the $R^7$ and $R^8$ groups are combined at both ends to form a 3- to 6-membered ring containing 0 to 2 oxygen or sulfur atoms in the ring;

$R^9$ is $R^7$, halogen, cyano, nitro, azide, $OR^7$, $S(O)_nR^7$, $NR^7R^8$, $C(O)R^7$, $CO_2R^7$, $C(O)NR^7R^8$, $SO_2NR^7R^8$, $OC(O)R^7$, $OCO_2R^7$, $OC(O)NR^7R^8$, $NR^8C(O)R^7$, $NR^8C(O)NR^7R^8$, $OSO_2R^7$ or $NR^8SO_2R^7$; or when m is equal to 2 the two $R^9$ groups are combined to form a 5- or 6-membered ring from $OCH_2O$, $OCH_2CH_2O$ or $CH_2CH_2O$, each of which may be optionally substituted with halogen or methyl;

$R^{10}$ is hydrogen, $C_1$–$C_4$ alkyl,

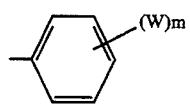

$S(O)_nR^7$, $C(O)R^7$, $CO_2R^7$, $C(O)NR^7R^8$, $C(S)NR^7R^8$, $C(S)R^7$, $P(O)(OR^7)_2$, $P(S)(OR^7)_2$ or $P(O)(R^7)(OR^7)$, with the proviso that when the $R^{10}$ group is any one other than $C(O)R^7$, $C(O)NR^7R^8$ and $C(S)NR^7R^8$ the $R^7$ group is not hydrogen;

A is $(CH_2)_t$, oxygen, $S(O)_n$, $NR^{10}$, $OCH_2$ or $S(O)_nCH_2$, wherein a hydrogen atom(s) attached to each carbon atom may be optionally substituted with halogen, $C_1$–$C_6$ alkyl, $C_3$–$C_6$ cycloalkyl, $C_3$–$C_6$ halocycloalkyl, $C_3$–$C_6$ cycloalkyl($C_1$–$C_4$)alkyl, $C_2$–$C_4$ alkoxycarbonyl or

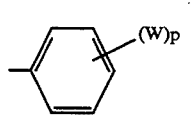

W is halogen, cyano, nitro, $C_1$–$C_2$ alkyl, $C_1$–$C_2$ haloalkyl, $C_1$–$C_2$ alkoxy, $C_1$–$C_2$ haloalkoxy, $C_1$–$C_2$ alkylthio, $C_1$–$C_2$ haloalkylthio, $C_1$–$C_2$ alkylsulfonyl or $C_1$–$C_2$ haloalkylsulfonyl;

a is an integer of 1 to 4; m is an integer of 0 to 3; t is an integer of 1 to 3; n is an integer of 0 to 2; and p is an integer of 0 to 5.

2. A hydrazone derivative according to claim 1, wherein A ms $CH_2$, $CH_2CH_2$, oxygen, sulfur, $NR^{10}$, $OCH_2$ or $SCH_2$, wherein a hydrogen atom(s) attached to each carbon atom may be optionally substituted with $C_1$–$C_6$ alkyl or

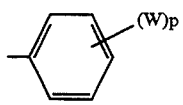

3. A hydrazone derivative according to claim 2, wherein each of $R^1$ and $R^9$ is independently $R^7$, halogen, cyano, nitro, $OR^7$, $SR^7$ or $NR^7R^8$; or when a or m is equal to 2 the two $R^1$ or $R^9$ groups are combined to form a 5- or 6-membered ring from $OCH_2O$, $OCH_2CH_2O$ or $CH_2CH_2O$, each of which may be optionally substituted with halogen or methyl;

$R^2$ is hydrogen, $C_1$–$C_6$ alkyl, $C_1$–$C_6$ haloalkyl, $C_3$–$C_6$ cycloalkyl, $C_3$–$C_6$ cycloalkyl($C_1$–$C_4$)alkyl, $C_3$–$C_6$ alkenyl, $C_3$–$C_6$ haloalkenyl, $C_3$–$C_6$ alkynyl, $C_3$–$C_6$ haloalkynyl, $C_1$–$C_6$ alkoxy($C_1$–$C_4$)alkyl, $C_1$–$C_6$ alkylthio($C_1$-$C_4$)alkyl, $C_2$-$C_6$ cyanoalkyl, $CO_2R^7$, $C(O)NR^7R^8$,

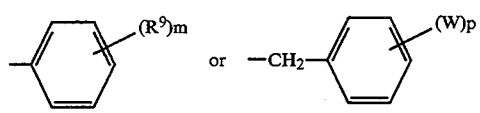

or $C_3$-$C_6$ cycloalkyl optionally substituted with halogen, methyl or trifluoromethyl;

$R^3$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, $C_3$-$C_6$ haloalkynyl, $C_1$-$C_6$ alkoxy($C_1$-$C_4$)alkyl, $C_1$-$C_6$ alkylthio($C_1$-$C_4$)alkyl, $C_2$-$C_6$ cyanoalkyl,

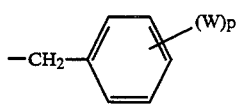

or $C_1$-$C_5$ alkylene optionally substituted with halogen or methyl, with the proviso that the $R^2$ and $R^3$ groups are combined at both ends to form a 3- to 6-membered ring containing 0 to 1 oxygen or sulfur atom in the ring;

$R^4$ is hydrogen, $C_1$-$C_6$ alkyl or $C_1$-$C_6$ haloalkyl;

$R^5$ is $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, $C_3$-$C_6$ haloalkynyl, $C_1$-$C_6$ alkoxy($C_1$-$C_4$)alkyl, $C_1$-$C_6$ alkylthio($C_1$-$C_4$)alkyl, $C_1$-$C_6$ haloalkoxy($C_1$-$C_4$)alkyl, $C_1$-$C_6$ haloalkylthio($C_1$-$C_4$)alkyl, $C_2$-$C_6$ cyanoalkyl, $C_2$-$C_6$ hydroxyalkyl, $C_1$-$C_4$ alkylamino($C_1$-$C_4$)alkyl or di($C_1$-$C_4$)alkylamino($C_1$-$C_4$)alkyl;

$R^6$ is hydrogen, $C_1$-$C_6$ alkyl, $C_2$-$C_6$ haloalkyl, $C_3$-$C_6$ alkenyl or $C_3$-$C_6$ alkynyl, $C_1$-$C_6$ alkoxy($C_1$-$C_4$)alkyl or $C_2$-$C_5$ alkylene optionally substituted with methyl, with the proviso that the $R^5$ and $R^6$ groups are combined at both ends to form a 3- to 6-membered ring containing 0 to 2 oxygen or sulfur atoms in the ring;

$R^7$ is hydrogen, $C_1$-$C_6$ alkyl, $C_1$-$C_6$ haloalkyl, $C_3$-$C_4$ alkenyl, $C_3$-$C_4$ alkynyl, $C_1$-$C_6$ alkoxy($C_1$-$C_4$)alkyl, $C_1$-$C_6$ alkylthio($C_1$-$C_4$)alkyl,

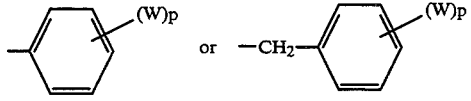

$R^8$ is hydrogen, $C_1$-$C_4$ alkyl, $C_3$-$C_4$ alkenyl or $C_3$-$C_4$ alkynyl; or $C_1$-$C_5$ alkylene optionally substituted with halogen or methyl, with the proviso that the $R^7$ and $R^8$ groups are combined at both ends to form a 3- to 6-membered ring containing 0 to 1 oxygen or sulfur atoms in the ring;

$R^{10}$ is hydrogen, $C_1$-$C_4$ alkyl,

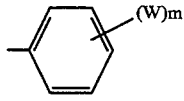

$C(O)R^7$, $CO_2R^7$ or $C(O)NR^7R^8$, with the proviso that when the $R^{10}$ group is $CO_2R^7$ the $R^7$ group is not hydrogen;

W is halogen, cyano, nitro, $C_1$-$C_2$ alkyl, $C_1$-$C_2$ haloalkyl, $C_1$-$C_2$ alkoxy, $C_1$-$C_2$ haloalkoxy or $C_1$-$C_2$ alkylthio;

a is an integer of 1 to 2; m is an integer of 0 to 2; n is an integer of 0 to 2; and p is an integer of 0 to 2.

4. A hydrazone derivative according to claim 3, wherein each of $R^1$ and $R^9$ is independently $R^7$ halogen cyano, nitro or $OR^7$; or when a or m is equal to 2 the two $R^1$ or $R^9$ groups are combined to form a 5-membered ring from $OCH_2O$ which may be optionally substituted with halogen or methyl;

$R^2$ is hydrogen, $C_1$-$C_6$ alkyl, $C_1$-$C_6$ haloalkyl, $C_3$-$C_4$ alkenyl, $C_3$-$C_4$ alkynyl $C_2$-$C_6$ cyanoalkyl, $CO2R^7$,

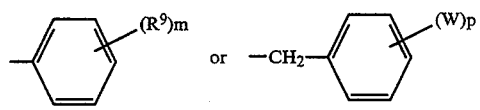

$R^3$ is hydrogen, $C_1$-$C_6$ alkyl, $C_1$-$C_6$ haloalkyl, $C_3$-$C_6$ alkenyl, $C_3$-$C_6$ alkynyl or $C_2$-$C_6$ cyanoalkyl; or $C_1$-$C_5$ alkylene optionally substituted with methyl, with the proviso that the $R^2$ and $R^3$ groups are combined at both ends to form a 3- to 6-membered ring containing 0 to 1 oxygen or sulfur atom in the ring;

$R^4$ is hydrogen or $C_1$-$C_6$ alkyl;

$R^5$ is $C_1$-$C_6$ alkyl, $C_1$-$C_6$ haloalkyl, $C_3$-$C_6$ alkenyl, $C_3$-$C_6$ alkynyl, $C_1$-$C_6$ alkoxy($C_1$-$C_4$)alkyl, $C_2$-$C_6$ cyanoalkyl, $C_2$-$C_6$ hydroxyalkyl, $C_1$-$C_4$ alkylamino($C_1$-$C_4$)alkyl or di($C_1$-$C_4$)alkylamino($C_1$-$C_4$)alkyl;

$R^6$ is hydrogen, $C_1$-$C_6$ alkyl, $C_2$-$C_6$ haloalkyl, $C_3$-$C_6$ alkenyl, $C_3$-$C_6$ alkynyl or $C_1$-$C_6$ alkoxy($C_1$-$C_4$)alkyl; or $C_2$-$C_5$ alkylene optionally substituted with methyl, with the proviso that the $R^5$ and $R^6$ groups are combined at both ends to form a 3- to 6-membered ring containing 0 to 1 oxygen or sulfur atoms in the ring;

$R^7$ is hydrogen, $C_1$-$C_3$ alkyl or $C_1$-$C_3$ haloalkyl; and $R^{10}$ is hydrogen, $C_1$-$C_4$ alkyl or ($C_1$-$C_4$ alkoxy)carbonyl.

5. A hydrazone derivative according to claim 4, wherein A is $CH_2$, $CH_2CH_2$, oxygen, sulfur, $NR^{10}$or $SCH_2$, wherein a hydrogen atom(s) attached to each carbon atom of $CH_2$ and $CH_2CH_2$ may be optionally substituted with methyl or

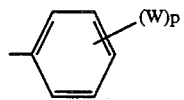

with the proviso that when A is oxygen, sulfur or $NR^{10}$ each of $R^2$ and $R^3$ is any one other than

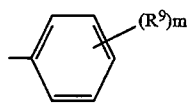

6. A hydrazone derivative according to claim 5, wherein each of $R^1$, $R^9$ and W is independently hydrogen, methyl, trifluoromethyl, fluorine, chlorine, bromine, cyano, methoxy, trifluoromethoxy or difluoromethoxy; or when a or m is equal to 2 the two $R^1$ or $R^9$ groups are methylenedioxy or difluoromethylenedioxy;

$R^2$ is hydrogen, $C_1$-$C_6$ alkyl, $C_1$-$C_6$ haloalkyl, $C_3$-$C_4$ alkenyl, $C_3$-$C_4$ alkynyl,

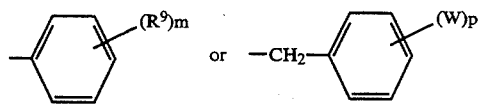

$R^3$ is hydrogen, $C_1$-$C_3$ alkyl, $C_3$-$C_4$ alkenyl or $C_3$-$C_4$ alkynyl; or $C_4$-$C_5$ alkylene, with the proviso that the $R^2$ and $R^3$ groups are combined at both ends to form a 5- to 6-membered ring;

$R^4$ is hydrogen or $C_1$-$C_6$ alkyl;

$R^5$ is $C_1$-$C_6$ alkyl, $C_3$-$C_4$ alkenyl, $C_3$-$C_4$ alkynyl or $C_1$-$C_3$ alkoxy($C_1$-$C_3$)alkyl.

7. A hydrazone derivative according to 6, wherein A is $CH_2$ or $CH_2CH_2$, wherein a hydrogen atom(s) attached to each carbon atom may be optionally substituted with methyl or

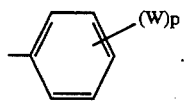

8. A hydrazone derivative according to claim 6, wherein A is oxygen, sulfur or $NR^{10}$, and each of $R^2$ and $R^3$ is any one other than

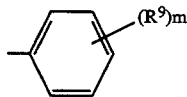

9. A hydrazone derivative according to claim 6, wherein A is $SCH_2$.

10. A hydrazone derivative according to claim 6, wherein A is $CH_2$.

11. A hydrazone derivative according to claim 6, wherein A is

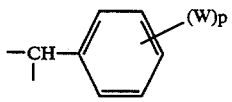

12. A hydrazone derivative according to claim 10, wherein $R^2$ is $C_1$-$C_6$ alkyl, allyl, propargyl or

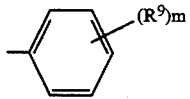

$R^3$ is hydrogen or $C_1$-$C_3$ alkyl; or $C_4$-$C_5$ alkylene, with the proviso that the $R^2$ and $R^3$ groups are combined at both ends to form a 5- or 6-membered ring;

$R^4$ is hydrogen or $C_1$-$C_4$ alkyl;

$R^5$ is $C_1$-$C_6$ alkyl, allyl or propargyl; and $R^6$ is $C_1$-$C_6$ alkyl.

13. A hydrazone derivative according to claim 12, wherein each of $R^1$ $R^9$ and W is independently hydrogen, methyl, fluorine, chlorine, bromine, methoxy or difluoromethoxy.

14. A hydrazone derivative according to claim 11, wherein each of $R^2$ and $R^3$ is independently hydrogen or $C_1$-$C_3$ alkyl;

$R^4$ is hydrogen or $C_1$-$C_4$ alkyl;

$R^5$ is $C_1$-$C_6$ alkyl, allyl or propargyl; and $R^6$ is $C_1$-$C_6$ alkyl.

15. A hydrozone derivative according to claim 14, wherein each of $R^1$ and W is independently hydrogen, methyl, fluorine, chlorine, bromine, methoxy or difluoromethoxy.

16. A compound of the formula:

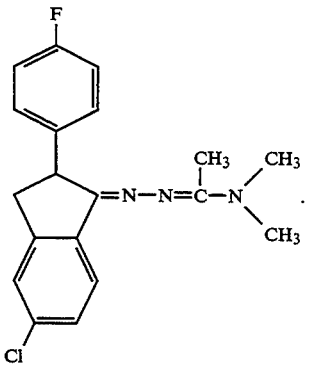

17. A compound of the formula:

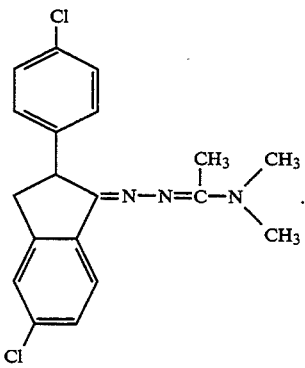

18. A compound of the formula:

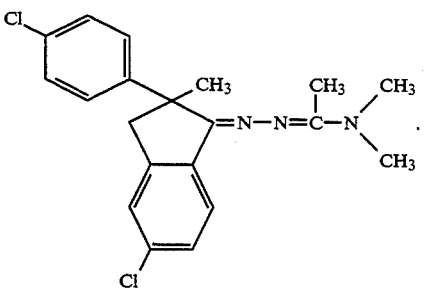

19. An insecticidal and/or acaricidal composition which comprises as an active ingredient a hydrazone derivative according to claim 1 and an inert carrier.

20. A method for controlling insect pests and/or acarine pests, which method comprises applying an insecticidally or acaricidally effective amount of a hydrazone derivative according to claim 1 to a locus where insect pests and/or acarine pests inhabit.

* * * * *